United States Patent
Ivashchenko et al.

(10) Patent No.: US 8,481,587 B2
(45) Date of Patent: Jul. 9, 2013

(54) SUBSTITUTED 2-(5-HYDROXY-2-METHYL-1H-INDOLE-3-YL)ACETIC ACIDS AND ETHERS THEREOF AND THE USE OF SAME TO TREAT VIRAL DISEASES

(76) Inventors: Andrey Alexandrovich Ivashchenko, Moscow (RU); Nikolay Filippovich Savchuk, Rancho Santa Fe, CA (US); Alexander Vasilievich Ivashchenko, Encinitas, CA (US); Pavel Mikhailovich Yamanushkin, Moscow (RU); Oleg Dmitrievich Mitkin, Moscow (RU); Vladimir Yurievich Vvedensky, Irkutsk (RU); Vadim Vasilievich Bichko, San Diego, CA (US)

( * ) Notice: Subject to any disclaimer, the term of this patent is extended or adjusted under 35 U.S.C. 154(b) by 153 days.

(21) Appl. No.: 13/130,311

(22) PCT Filed: Nov. 27, 2009

(86) PCT No.: PCT/RU2009/000655
§ 371 (c)(1),
(2), (4) Date: May 20, 2011

(87) PCT Pub. No.: WO2010/062221
PCT Pub. Date: Jun. 3, 2010

(65) Prior Publication Data
US 2011/0230524 A1 Sep. 22, 2011

(30) Foreign Application Priority Data

Nov. 27, 2008 (RU) ................. 2008146873

(51) Int. Cl.
*A61K 31/405* (2006.01)
*C07D 209/12* (2006.01)
(52) U.S. Cl.
USPC .......................... 514/419; 548/494
(58) Field of Classification Search
USPC ...................................... 548/494
See application file for complete search history.

(56) References Cited

U.S. PATENT DOCUMENTS

2010/0197708 A1* 8/2010 Talley et al. ................ 514/269

OTHER PUBLICATIONS

Chronic Hepatitis C: Current Disease Management. [online], [retrieved on Nov. 8, 2007]. Retrieved from the internet, URL; http:IIdigestive.niddk.nih.govIddiseasesIpubsIchronichepcIindex.htm>.*

* cited by examiner

Primary Examiner — Shawquia Young

(57) ABSTRACT

The present invention relates to novel substituted 2-(5-hydroxy-2-methyl-1H-indol-3-yl)acetic acids, to novel antiviral active ingredients, pharmaceutical compositions, antiviral medicaments, methods for prophylaxis and treatment of viral diseases particularly caused by influenza viruses and infectious hepatisis C (HCV) viruses.

Novel substituted 2-(5-hydroxy-2-methyl-1H-indol-3-yl) acetic acids, their esters of the general formula 1 and pharmaceutically acceptable salts and/or hydrates thereof have been disclosed

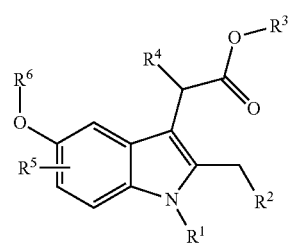

wherein: $R^1$ represents amino group substituent selected from hydrogen, optionally substituted $C_1$-$C_5$ alkyl, acyl or sulfonyl; $R^2$ and $R^4$ independently of each other represent alkyl substituent selected from hydrogen, halogen, optionally substituted $C_1$-$C_3$ alkyl, optionally substituted hydroxyl, optionally substituted amino group, optionally substituted aminomethyl, substituted mercapto group; $R^3$ represents hydrogen, optionally substituted lower $C_1$-$C_5$ alkyl; $R^5$ represents cyclic system substituent selected from hydrogen, fluorine, trifluoromethyl, carboxy group, alkyloxycarbonyl, possibly substituted aryl, heterocyclyl, optionally substituted aminomethyl, cyano group; $R^6$ represents hydroxyl group substituent selected from hydrogen, optionally substituted $C_1$-$C_5$ alkyl, acyl.

19 Claims, No Drawings

SUBSTITUTED 2-(5-HYDROXY-2-METHYL-1H-INDOLE-3-YL)ACETIC ACIDS AND ETHERS THEREOF AND THE USE OF SAME TO TREAT VIRAL DISEASES

FIELD OF THE INVENTION

The present invention relates to novel substituted 2-(5-hydroxy-2-methyl-1H-indol-3-yl)acetic acids and esters thereof, to novel antiviral active ingredients, pharmaceutical compositions, antiviral medicaments, therapeutic cocktails, methods for prophylaxis and treatment of viral diseases, especially caused by influenza and infectious hepatitis C (HCV) viruses.

BACKGROUND OF THE INVENTION

Virus infections may cause a great number of diseases that creates a serious threat to health and survival of mankind. For the last 20 years no less than 30 entirely new infectious agents have been discovered such as: HIV, viral hepatitises, acute and long-lasting diarrhoea, hemorrhagic fever (Ebola, Venezuelan, Brazilian, Rift valleys) [a) Lednicky J. A., Rayner J. O. Uncommon respiratory pathogens. Curr. Opin. Pulm. Med. 2006, 12(3), 235-239. b) Hayden F. G. Respiratory viral threats. Curr. Opin. Infect. Dis. 2006, 19(2), 169-178]. In particular, special anxiety is caused by the possibility to get sick with named avian influenza [a) Liu J. P. Avian influenza-a pandemic waiting to happen? *J. Microbiol. Immunol. Infect.* 2006, 39(1), 4-10. b) Henter J. I.; Chow C. B.; Leung C. W, Lau Y. L. Cytotoxic therapy for severe avian influenza A (H5N1) infection. *Lancet.* 2006 367(9513), 870-873. Review]. According to statistical data 60-65% of epidemic infections have viral etiology. Because of interaction complexity in triad "virus—host's organism—drug", most of modern antiviral drugs in the course of therapy exhibit side effects and form resistant virus strains [Jain R., Clark N. M., Diaz-Linares M., Grim S. A. Limitations of current antiretroviral agents and opportunities for development. *Curr. Pharm. Des.* 2006, 12(9), 1065-1074.]. At present, the number of antiviral drugs that could be used in clinical practice is extremely limited—only 43 substances of low molecular weight [http://integrity.prous.com/integrity], that is far from satisfying requirements of prophylaxis and treatment of virus diseases. Besides, there are a lot of virus infections causing diseases for treatment of which there are no chemotherapeutic agents. It is referred, for example, to the diseases caused by viruses of papilloma, adenoviruses, herpes-6, variola, syndrome SARS, hemorrhagic fevers, fever of the Western Nile, avian influenza and so on [De Clercq E. Recent highlights in the development of new antiviral drugs. *Curr Opin Microbiol.* 2005, 8(5), 552-560].

Therefore the development of new antiviral drugs, in particular, with new mechanism of antiviral action, high activity, and low toxicity is of great importance now.

Anti-influenza drug Arbidol based on the pharmaceutical composition comprising ethyl 6-bromo-4-[(dimethylamino)methyl]-5-hydroxy-1-methyl-2-(phenylthiomethyl)-1H-indole-3-carboxylate hydrochloride as an active ingredient is well known [Arbidol, PCT Int. Appl. WO 9008135, 1990],

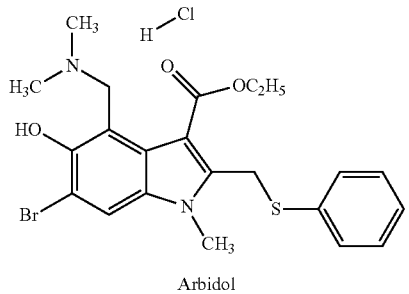

Arbidol

Arbidol is used for prophylaxis and treatment of diseases caused by influenza viruses. It demonstrates the ability to induce interferon and shows immunomodulating effect. [Arbidol. Drugs R. D. 1999, September; 2(3), 171-172. Gluskova, T.; Glushkov, R. Arbidol is Interferon inductor, immunomodulator, antioxidant. *Rev. Esp. Quimioter.* 2000, 13(Suppl. 2), Abstr. M182].

However, the main disadvantage of Arbidol is its high cellular toxicity ($CC_{50}$=10-20 mM) and, as a result of it, small therapeutic window or low selectivity index ($SI_{50}$). For influenza virus, for example, it is equal only to 2.69 (on cellular line MDCK $TC_{50}$=62.5 µg/ml and $IC_{50}$=23.2 mkg/ml) [PCT Int Appl. WO 2005/087729 A1, 2005]. Its toxicity is even higher on some other cellular lines ($CC_{50}$=15-25 µg/ml) [Brooks M J: Studies with the antiviral drug arbidol [PhD thesis]. Melbourne, Australia: RMIT University; 2003].

There are known antiviral pharmaceutical compositions comprising as active ingredients Arbidol analogs of the general formula A. [PCT Int Appl. WO 2004060873, 2004; PCT Int Appl. WO 2005087729 A1, 2005. *Bioorg. Med. Chem.* 2006, 14(4), 911-917],

A

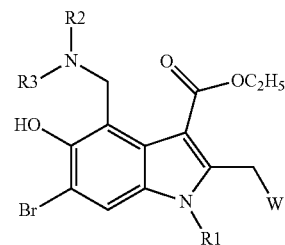

wherein: R1 represents alkyl or cycloalkyl; R2 and R3 independently of each other represent amino group substituent selected from hydrogen, optionally substituted alkyl, optionally substituted cycloalkyl, optionally substituted aryl or optionally substituted heterocyclyl, or R2 and R3 together with the nitrogen atom they are attached to form through R2 and R3 optionally substituted azaheterocyclyl; W represents substituted mercapto group.

Arbidol analoges of the general formula A exhibit also suppressing activity towards influenza A and B viruses, as well as viruses of hepatitis B (HBV) and human immunodeficiency virus (HIV) [*Bioorg. Med. Chem.* 2006, 14(4), 911-

917. PCT Int Appl. WO 2005/087729 A1, 2005]. However, Arbidol analoges of the general formula A, as well as Arbidol itself, show high cellular toxicity and, as a result of it, low selectivity index. Thus, for example, selectivity index for this series of compounds towards hepatitis B is, as a rule, <10 ($SI_{50}$=1.81-10.8) [*Bioorg. Med. Chem.* 2006, 14(4), 911-917].

There are also known more effective Arbidol analoges representing substituted 5-hydroxy-1-methyl-2-((dimethylamino)methyl)-1H-indole-3-carboxylates of the general formulas B1 and B2 [PCT Int Appl. WO 2007/136300 A2, 29 Nov. 2007; PCT Int Appl. WO 2007/136302 A2, 29 Nov. 2007],

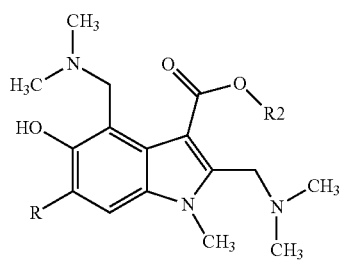

B1

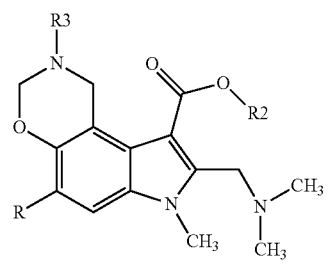

B2 wherein: R represents a cyclic system substituent selected from hydrogen, halogen, cyano group, optionally substituted aryl or optionally substituted heterocyclyl; R2 represents a lower alkyl; R3 represents an amino group substituent selected from hydrogen, optionally substituted alkyl, optionally substituted cycloalkyl, optionally substituted aryl or optionally substituted heterocyclyl.

There are known various substituted 2-(5-hydroxy-2-methyl-1H-indol-3-yl)acetic acids and esters thereof, exhibiting various types of biological activity: antiinflammatory, antiarthritis, anxiolytic, analgestic and so on. In particular, there are known 2-(2-methyl-5-methoxy-1H-indol-3-yl)acetic acid A1(1) [U.S. Pat. No. 3,161,654, DE 1232150], its ester A1(2) [*Arzneim. Forsch.* 37 (7), 806-813, 1987] and substituted 2-(1-benzoyl-2-methyl-5-methoxy-1H-indol-3-yl)acetic acids and esters thereof of the general formula A2 [BE 0858897, DE 3235850, EP 0078765, EP 0237495, CS 194283, CS 194284, FR 1540724, U.S. Pat. No. 4,136,194, U.S. Pat. No. 4,181,740, U.S. Pat. No. 5,436,265, U.S. Pat. No. 4,455,316, JP 1999043467, EP 1510205, JP 2004175723, JP 2005047906, JP 2005047907, JP 2005145931, JP 2005145932, JP 2005213192, JP 2006045099, JP 2006151836, JP 2006241341, JP 2006248922, JP 2007007189, US 2006178347, U.S. Pat. No. 6,051,587, WO 1987002891, WO 1990000545, WO 1998009948, WO 2000004897, WO 2000004897, WO 2000044705, WO 2001062085, WO 2001095913, WO 2002065977, WO 2003097057, WO 2004094409, WO 2004010994, WO 2005002525, WO 2005007650, WO 2005013980, WO 2005039565, WO 2005074992, WO 2005079856, WO 2005094788, WO 2005099674, WO 2006020994, WO 2006051818, WO 2006051819, WO 2006070672, WO 2006070673, WO 2006096955, WO 2006126214, WO 2007000842, WO 2007014476, WO 2007018210, WO 2007046318, WO 2007005941, WO 2007127725, WO 2007014476],

A1(1)

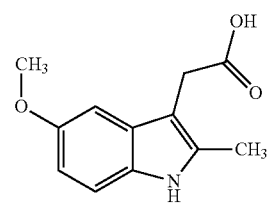

A1(2)

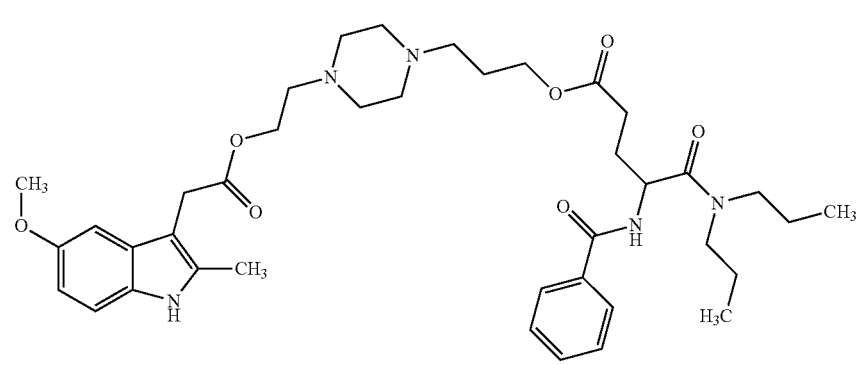

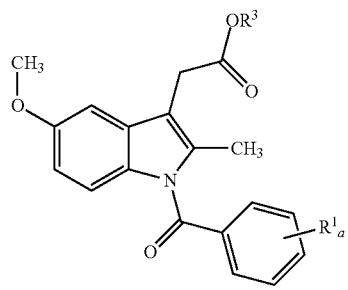

A2 wherein: R³ represents hydrogen, optionally substituted $C_1$-$C_5$-alkyl, optionally substituted aryl; $R^1_a$ represents 4-F, 4-Cl, 4-CF₃, 4-CF₃O, 4-N₃, 2,4,6-Cl₃.

There are also known substituted 2-(1-acyl-2-methyl-5-methoxy-6-fluoro-1H-indol-3-yl)acetic acids A3(1)-A3(7) [WO 2006036994, WO 2005002525], substituted 2-(1-benzyl-2-methyl-5-methoxy-6-chloro-1H-indol-3-yl)acetic acids A4(1), A4(2) [WO 2005002525, WO 2007022501], substituted 2-(1-benzoyl-2-methyl-5-methoxy-6-chloro-1H-indol-3-yl)acetic acids A5(1), A5(2), [WO 2005002525], 2-[1-(3-phenylacryloyl)-2-methyl-5-methoxy-1H-indol-3-yl]acetates A6(1), A6(2), A6(3) [WO 1994006769], 2-(1-benzoyl-5-hydroxy-2-methyl-1H-indol-3-yl)acetic acids A7(1), A7(2), A7(3), A7(4) [WO 2005037227, WO 2005002525, WO 2006036994], [2-(1-methylpiperidin-4-yl)-5-hydroxy-2-methyl-1H-indol-3-yl]acetic acid A8(1), its ethyl ester A8(2) and 2-(1-heterocyclyl-2-methyl-5-methoxy-1H-indol-3-yl)acetic acids A9(1), A9(2), A9(3) [WO 2003066047] and pharmaceutically acceptable salts thereof A10(1)-A10(4) [DE 3036367, WO 1997003678, WO 2006099677, WO 2006099684, WO 2006099685],

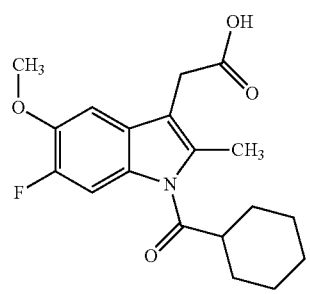

A3(1)

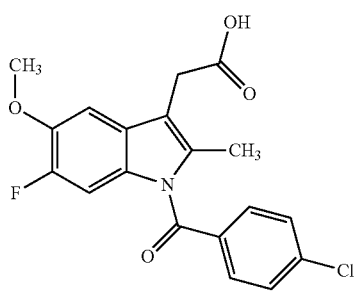

A3(2)

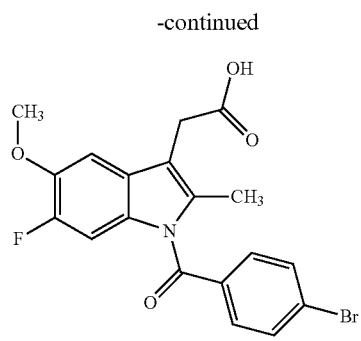

A3(3)

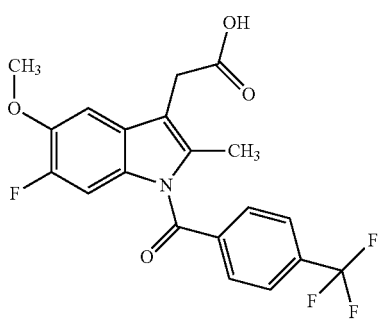

A3(4)

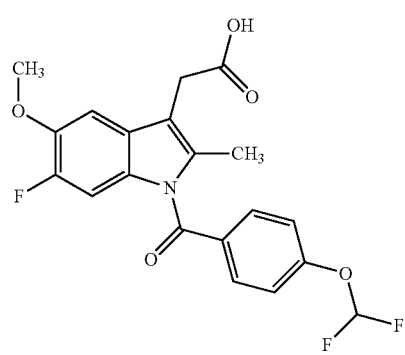

A3(5)

A3(6) 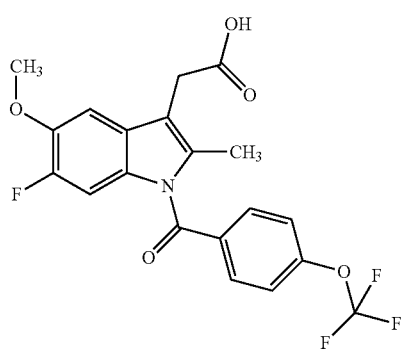
A3(7) 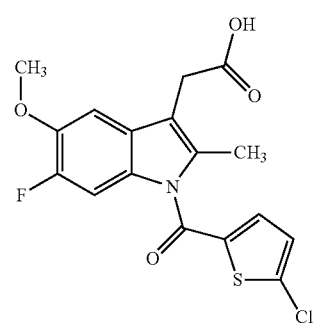
A4(1) 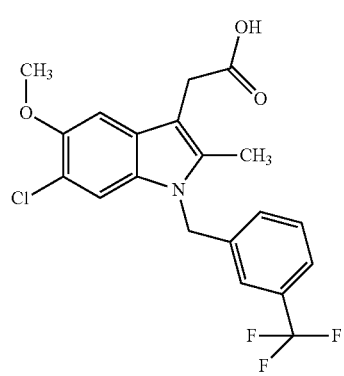
A4(2) 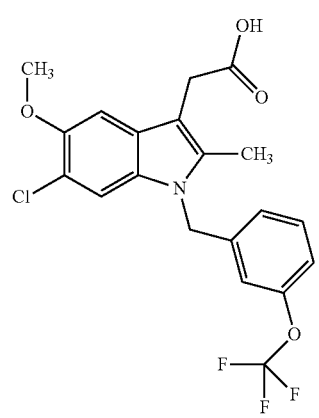
A5(1) 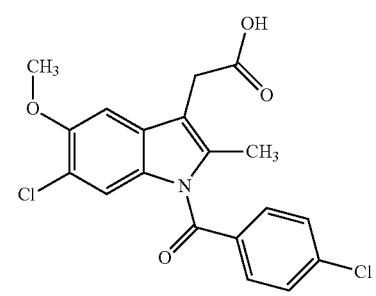
A5(2) 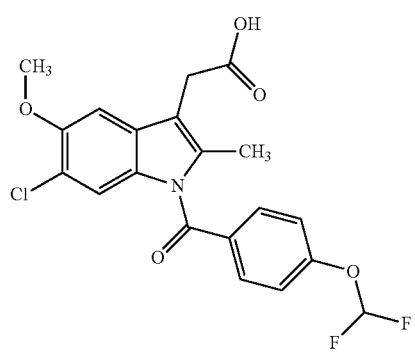
A6(1) 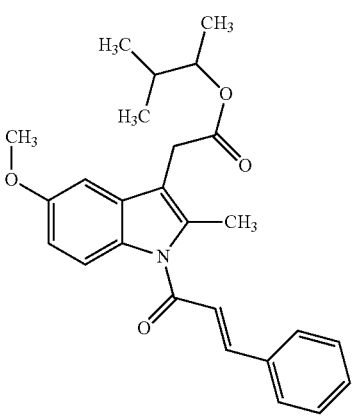
A6(2) 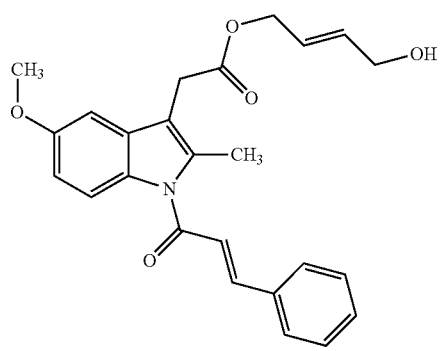

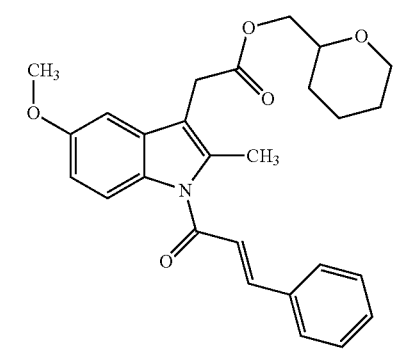
A6(3)
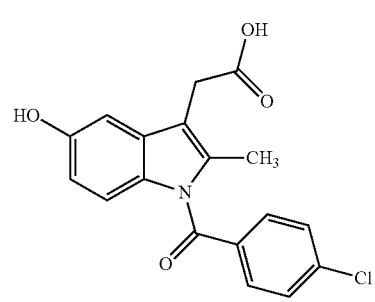
A7(1)
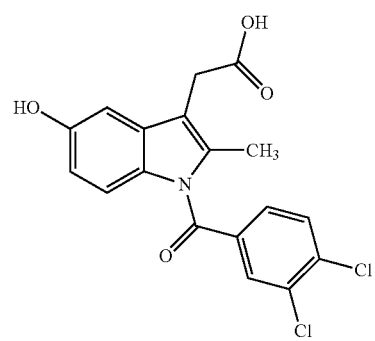
A7(2)
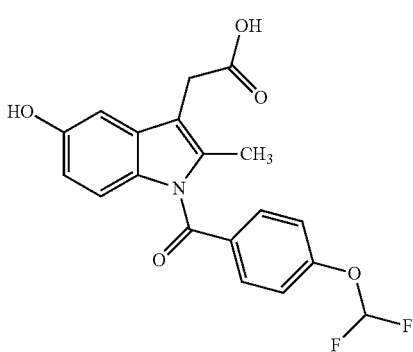
A7(3)
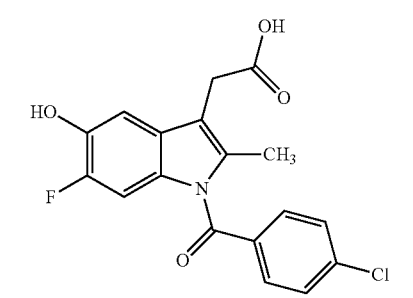
A7(4)
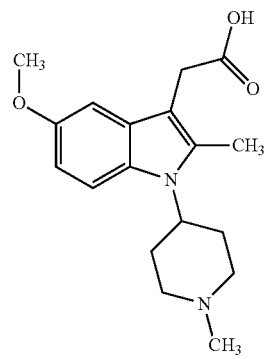
A8(1)
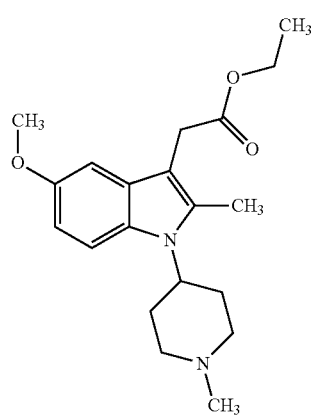
A8(2)
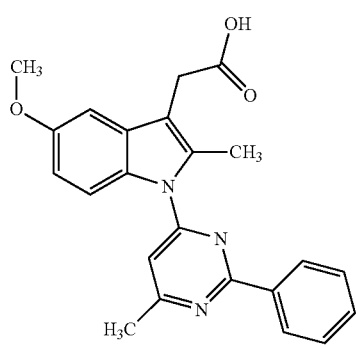
A9(1)
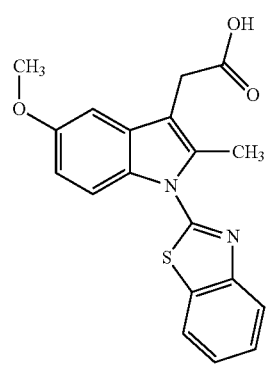
A9(2)

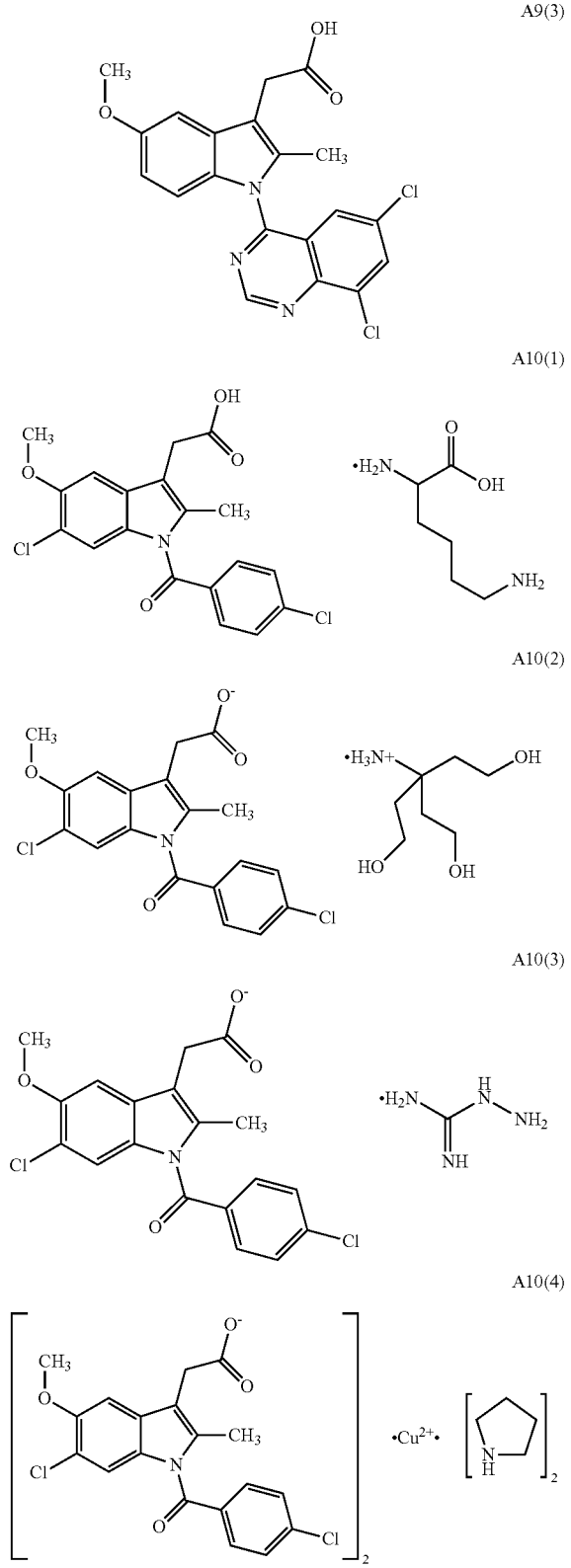

However, substituted 2-(5-hydroxy-2-methyl-1H-indol-3-yl)acetic acids and esters thereof exhibiting antiviral activity, including compounds A1-A10, have not been known up to now.

Searching for highly effective antiviral drugs is one of the main directions for the development of new pharmacological remedies for treatment of wide range of virus infections now. In this context design of new antiviral active ingredients, pharmaceutical compositions and medicaments, methods for their preparation and application are of vital importance.

DISCLOSURE OF THE INVENTION

In the context of the present invention, the terms are generally defined as follows:

"Azaheterocycle" means an aromatic or nonaromatic mono- or poly-cyclic system with, at least, one nitrogen atom in the cycle. Azaheterocycle may have one or more "cyclic system substituents".

"Drug-substance" means physiologically active compounds of synthetic or other (biotechnological, vegetable, animal, microbe and so on) origin exhibiting pharmacological activity and being an active ingredient of pharmaceutical composition employed in preparation and production of medicaments.

"Alkyl" means aliphatic hydrocarbon straight or branched group with 1-12 carbon atoms. Branched means alkyl chain with one or more "lower alkyl" side substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonyl, heteroaralkyloxy and so on.

"Alkoxy" means an alkyl-O-group, in which alkyl is defined herein. The preferred alkoxy groups are methoxy, ethoxy, n-propoxy, iso-propoxy and n-butoxy.

"Alkyloxyalkyl" means an alkyl-O-alkyl group in which alkyl groups are independent of each other and defined herein. The preferred alkyloxyalkyl groups are methoxyethyl, ethoxymethyl, n-butoxymethyl, methoxypropyl, and iso-propyloxyethyl.

"Alkoxycarbonyl" means an alkyl-O—C(=O)-group, in which alkyl is defined herein. Methoxycarbonyl, ethoxycarbonyl, n-butyloxycarbonyl, iso-propyloxycarbonyl, tert-butyloxycarbonyl, benzyloxycarbonyl and phenethyloxycarbonyl are the preferred alkoxycarbonyl groups.

"Amino group" means $R_k^a R_{k+1}^a$N-group substituted or not by "amino-group substituent", the meanings of $R_k^a$ and $R_{k+1}^a$ are defined herein, for example, amino (NH$_2$), methylamino, diethylamino, pyrrolidino, morpholino, benzylamino or phenethylamino.

"Aryl" means aromatic mono- or polycyclic system with 6-14 carbon atoms, preferably from 6 to 10 C-atoms. Aryl may have one or more "cyclic system substituents" of the same or different structure. Phenyl or naphthyl, substituted phenyl or substituted naphthyl are the representatives of aryl groups. Aryl could be annelated with nonaromatic cyclic system or heterocycle.

"Aryloxy" means an aryl-O-group, in which the meaning of aryl is defined herein. Phenoxy- and 2-naphthyloxy- are the representatives of aryloxy group.

"Arylsulfonyl" means an aryl-SO$_2$-group, in which the meaning of aryl is defined herein.

"Aroyl" means an aryl-C(=O)-group, in which the meaning of aryl is defined herein. Benzoyl-, 1- and 2-naphthoyl- are the representatives of aroyl groups.

"Aromatic radical" means a radical derived at removal of hydrogen atom from aromatic C—H bond. "Aromatic" radical implies aryl and heteroaryl cycles, the meaning of which are defined herein. Aryl and heteroaryl cycles may additionally contain substituents, such as aliphatic and aromatic radicals, the meaning of which are defined herein. Aryl, annelated cycloalkenylaryl, annelated cycloalkylaryl, annelated heterocyclylaryl, annelated heterocyclenylaryl, heteroaryl, annelated cycloalkylheteroaryl, annelated cycloalkenylheteroaryl, annelated heterocyclenylheteroaryl and annelated heterocyclylheteroaryl are the representatives of aromatic radicals.

"Acyl" means H—C(=O)—, alkyl-C(=O)—, cycloalkyl-C(=O), heterocyclyl-C(=O)—, heterocyclyl-alkyl-C(=O)—, aryl-C(=O)—, arylalkyl-C(=O)—, heteroaryl-C(=O)—, heteroarylalkyl-C(=O)-groups, in which alkyl-, cycloalkyl-, heterocyclyl-, heterocyclylalkyl-, aryl-, arylalkyl-, heteroaryl-, heteroarylalkyl are defined herein.

"Halogen" means fluorine, chlorine, bromine and iodine. Preference is given to fluorine, chlorine and bromine.

"Heteroaryl" means an aromatic mono- or polycyclic system with 5-14 carbon atoms, preferably from 5 to 10, in which one or more carbon atoms are substituted by one or more heteroatoms, such as N, S or O. Prefix "aza", "oxa" or "thia" before "heteroaryl" means that atoms N, O or S respectively are introduced in the appropriate cyclic fragment. N-Atom of heteroaryl cycle could be oxidized to N-oxide. Heteroaryl may have one or more "cyclic system substituents" of the same or different structure. Pyrrolyl, furanyl, thienyl, pyridyl, pyrazinyl, pyrimidinyl, isooxazolyl, isothiazolyl, tetrazolyl, oxazolyl, thiazolyl, pyrazolyl, furazanyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzoimidazolyl, benzothiazenyl, quinolinyl, imidazolyl, thienopyridyl, quinazolinyl, thienopyrimidinyl, pyrrolopyridinyl, imidazopyridinyl, isoquinolinyl, benzoazaindolyl, 1,2,4-triazinyl, thienopyrrolyl, furopyrrolyl and others are the representatives of heteroaryl radicals.

"Heterocycle" means an aromatic or nonaromatic mono- or polycyclic system comprising in the cycle at least one heteroatom. The preferable heteroatoms are N, O and S. Heterocycle may have one or more "cyclic system substituents".

"Heterocyclyl" means a radical derived from heterocycle.

"Hydrate" means stoichiometric or nonstoichiometric compositions of the compounds or their salts with water.

"Hydroxyalkyl" means an HO-alkyl-group, in which alkyl is defined herein.

"Substituent" means a chemical radical attached to a scaffold (fragment), for example, "alkyl substituent", "amino group substituent", "carbamoyl substituent", and "cyclic system substituent", the meanings of which are defined herein.

"Alkyl group substituent" means a substituent attached to alkyl or alkenyl group, the meanings of which are defined herein. Alkyl group substituent is selected from hydrogen, alkyl, halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonyl, heteroaralkyloxy, annelated heteroarylcycloalkenyl, annelated heteroarylcycloalkyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N$—, $R_k^a R_{k+1}^a NC(=O)$—, $R_k^a R_{k+1}^a NSO_2$—, where $R_k^a$ and $R_{k+1}^a$ independently of each other represent "amino group substituent", the meanings of which are defined herein, for example, hydrogen, alkyl, aryl, aralkyl, heteroaralkyl, heterocyclyl or heteroaryl, or $R_k^a$ and $R_{k+1}^a$ together with the N-atom they are attached to via $R_k^a$ and $R_{k+1}^a$ form 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, and pyridylmethyloxycarbonylmethyl. The preferred "alkyl group substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N$—, $R_k^a R_{k+1}^a NC(=O)$—, annelated arylheterocyclenyl, annelated arylheterocyclyl. The meanings of "alkyl group substituents" are defined herein.

"Amino group substituent" means a substituent attached to amino group. Amino group substituent represents hydrogen, alkyl, cycloalkyl, aryl, heteroaryl, heterocyclyl, acyl, aroyl, alkylsulfonyl, arylsulfonyl, heteroarylsulfonyl, alkylaminocarbonyl, arylaminocarbonyl, hetero arylamino carbonyl, heterocyclylaminocarbonyl, alkylaminothiocarbonyl, arylaminothiocarbonyl, heteroarylaminothiocarbonyl, heterocyclylaminothiocarbonyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonylalkyl, aralkoxycarbonylalkyl, heteroaralkyloxycarbonylalkyl.

"Hydroxy group substituent" means a substituent attached to hydroxyl group including alkyl, aryl, heteroaryl, aralkyl, heteroaralkyl, hydroxyalkyl, acyl, aroyl, alkyloxyalkyl, aryloxyalkyl, heterocyclyloxyalkyl and so on.

"Cyclic system substituent" means a substituent attached to aromatic or nonaromatic cyclic system and selected from hydrogen, alkyl, alkenyl, alkynyl, aryl, heteroaryl, aralkyl, heteroaralkyl, hydroxy, hydroxyalkyl, amino, aminoalkyl, alkoxy, aryloxy, acyl, aroyl, halogen, nitro, cyano, carboxy, alkoxycarbonyl, aryloxycarbonyl, aralkoxycarbonyl, alkyloxyalkyl, aryloxyalkyl, heterocyclyloxyalkyl, arylalkyloxyalkyl, heterocyclylalkyloxyalkyl, alkylsulfonyl, arylsulfonyl, heterocyclylsulfonyl, alkylsulfinyl, arylsulfinyl, heterocyclylsulfinyl, alkylthio, arylthio, heterocyclylthio, alkylsulfonylalkyl, arylsulfonylalkyl, heterocyclylsulfonylalkyl, alkylsulfinylalkyl, arylsulfinylalkyl, heterocyclylsulfinylalkyl, alkylthio alkyl, arylthio alkyl, heterocyclylthio alkyl, arylalkylsulfonylalkyl, heterocyclylalkylsulfonylalkyl, arylalkylthio alkyl, heterocyclylalkylthioalkyl, cycloalkyl, cycloalkenyl, heterocyclyl, heterocyclenyl, amidino, $R_k^a R_{k+1}^a N$—, $R_k^a N=$, $R_k^a R_{k+1}^a N$-alkyl, $R_k^a R_{k+1}^a NC(=O)$— or $R_k^a R_{k+1}^a NSO_2$—, where $R_k^a$ and $R_{k+1}^a$ independently of each other represent "amino group substituents", the meanings of which are defined herein, for example, hydrogen, optionally substituted alkyl, optionally substituted aryl, optionally substituted aralkyl, optionally substituted heteroaralkyl or $R_k^a R_{k+1}^a N$-substituent in which $R_k^a$ could be acyl or aroyl, the meaning of $R_{k+1}^a$ is defined above, or "cyclic system substituents" are $R_k^a R_{k+1}^a NC(=O)$— or $R_k^a R_{k+1}^a NSO_2$—, where $R_k^a$ and $R_{k+1}^a$ together with the N-atom they are attached to via $R_k^a$ and $R_{k+1}^a$ form 4-7-membered heterocyclyl or heterocyclenyl.

"Substituted amino group" means $R_k^a R_{k+1}^a N$-group, in which $R_k^a$ and $R_{k+1}^a$ represent amino group substituents the meanings of which are defined herein.

"Substituted carboxyl" means C(O)OR-group. Substituted carboxyl has a substituent R including alkenyl, alkyl, aryl, heteroaryl, heterocyclyl, the meanings of which are defined in this section.

"Carboxyl" means HOC(=O)— (carboxyl) group.

"Medicament"—is a compound or a mixture of compounds representing pharmaceutical composition in the form of tablets, capsules, injections, ointments and other drug products intended for restoration, improvement or modification of physiological functions at humans and animals, and for prophylaxis and treatment of diseases, diagnostics, anesthesia, contraception, cosmetology and others.

"Optionally substituted radical" means a radical without substituents or including one or more substituents.

"Lower alkyl" means straight or branched alkyl with 1-4 C atoms.

"Substituted mercapto group" means R—S— group in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl.

"Sulfonyl group" means R—SO$_2$— group in which R represents alkyl, cycloalkyl, aryl, heteroaryl, heterocyclyl, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl.

"Therapeutic cocktail" is a simultaneously administered combination of two or more drug substances with different mechanism of pharmacological action and aimed at different biotargets taking part in pathogenesis of the disease.

"Pharmaceutical composition" means a composition comprising, at least, one of the compounds of the general formula 1 and, at least, one of the components selected from pharmaceutically acceptable and pharmacologically compatible fillers, solvents, diluents, auxiliary agents, distributing and sensing agents, delivery agents, such as preservatives, stabilizers, disintegrators, moisteners, emulsifiers, suspending agents, thickeners, sweeteners, flavoring agents, aromatizing agents, antibacterial agents, fungicides, lubricants, and prolonged delivery controllers, the choice and suitable proportions of which depend on the nature and way of administration and dose. Examples of suitable suspending agents are: ethoxylated isostearyl alcohol, polyoxyethene, sorbitol and sorbitol ether, microcrystalline cellulose, aluminum metahydroxide, bentonite, agar-agar and tragacant and their mixtures as well. Protection against the action of microorganisms can be provided by various antibacterial and antifungal agents, such as: parabens, chlorobutanol, sorbic acid, and similar compounds. Composition may also contain isotonic agents, such as: sugar, sodium chloride, and similar compounds. Prolonged effect of the composition may be achieved by agents slowing down absorption of the active ingredient, for example, aluminum monostearate and gelatin. Examples of suitable carriers, solvents, diluents and delivery agents include water, ethanol, polyalcohols and their mixtures, natural oils (such as olive oil) and injection-grade organic esters (such as ethyl oleate). Examples of fillers are: lactose, milk-sugar, sodium citrate, calcium carbonate, calcium phosphate and the like. Examples of disintegrators and distributors are: starch, alginic acid and its salts, and silicates. Examples of suitable lubricants are: magnesium stearate, sodium lauryl sulfate, talc and polyethylene glycol of high molecular weight. Pharmaceutical composition for peroral, sublingual, transdermal, intramuscular, intravenous, subcutaneous, local or rectal administration of active ingredient, alone or in combination with another active compound, may be administered to humans and animals in a standard administration form as a mixture with traditional pharmaceutical carriers. Suitable standard administration forms include peroral forms such as tablets, gelatin capsules, pills, powders, granules, chewing-gums and peroral solutions or suspensions, for example, therapeutic cocktail; sublingual and transbuccal administration forms; aerosols; implants; local, transdermal, subcutaneous, intramuscular, intravenous, intranasal or intraocular forms and rectal administration forms.

"Pharmaceutically acceptable salt" means relatively nontoxic organic or inorganic salts of both acids and bases disclosed in this invention. Salts could be prepared in situ in process of synthesis, isolation or purification of compounds or prepared specially. In particular, salts of bases could be prepared starting from purified bases disclosed in the invention and suitable organic or mineral acid. Examples of salts prepared in this manner include: hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulfonates, malonates, salicylates, propionates, ethane sulfonates, benzene sulfonates, sulfamates and the like (Detailed description of such salts properties is given in: Berge S. M., et al., "Pharmaceutical Salts" J. Pharm. Sci., 1977, 66: 1-19). Salts of the disclosed acids may be prepared by the reaction of purified acids with a suitable base; moreover, metal salts and amine salts may be synthesized too. Metal salts are salts of sodium, potassium, calcium, barium, magnesium, lithium and aluminum; sodium and potassium salts are being preferred. Suitable inorganic compounds from which metal salts can be prepared are: sodium hydroxide, carbonate, bicarbonate and hydride; potassium hydroxide, carbonate and bicarbonate; lithium hydroxide, calcium hydroxide, magnesium hydroxide, zinc hydroxide. Organic bases suitable for preparation of the disclosed acid salts are amines and amino acids the basicity of which is high enough to produce stable salts suitable for medicinal purposes (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as: holine, tetramethylammonium, tetraethylammonium, and the like. Amino acids may be selected from the main amino acids—lysine, ornithine and arginine.

The subject of the present invention is novel substituted 2-(5-hydroxy-2-methyl-1H-indol-3-yl)acetic acids, their esters of the general formula 1 and pharmaceutically acceptable salts and/or hydrates thereof

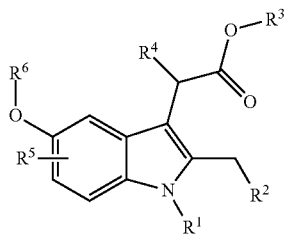

1 wherein:
R[1] represents an amino group substituent selected from hydrogen, optionally substituted $C_1$-$C_5$ alkyl, acyl or sulfonyl;
R[2] and R[4] independently of each other represent an alkyl group substituent selected from hydrogen, halogen, optionally substituted $C_1$-$C_3$ alkyl, optionally substituted hydroxyl, optionally substituted amino group, optionally substituted aminomethyl, substituted mercapto group;
R[3] represents hydrogen, optionally substituted $C_1$-$C_5$ alkyl;
R[5] represents a cyclic system substituent selected from hydrogen, fluoro, trifluoromethyl, carboxyl, alkyloxycarbonyl, conceivably substituted aryl, heterocyclyl, optionally substituted aminomethyl, cyano group;
R[6] represents a hydroxyl group substituent selected from hydrogen, optionally substituted $C_1$-$C_5$ alkyl, acyl,
with the exception of 2-(2-methyl-5-methoxy-1H-indol-3-yl) acetic acid A1(1) and its ester A1(2), substituted 2-(1-acyl-2-methyl-5-methoxy-6-fluoro-1H-indol-3-yl)acetic acids A3(1)-A3(7),

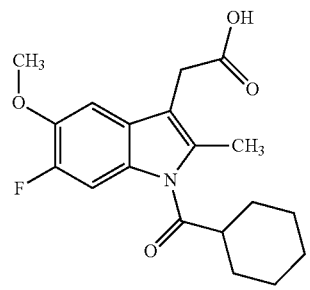

A3(1)

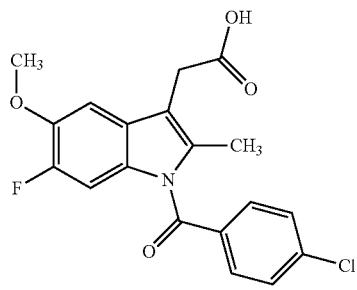

A3(2)

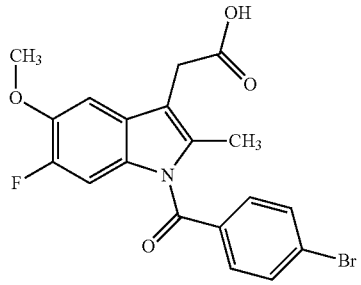

A3(3)

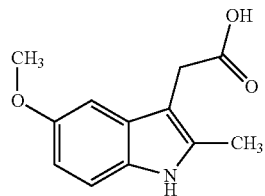

A1(1)

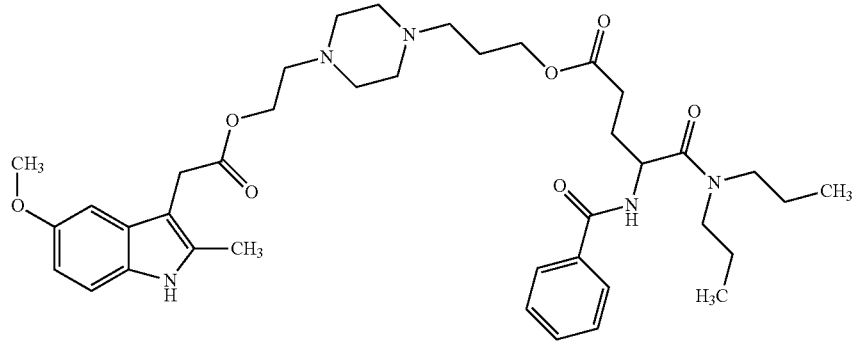

A1(2)

A3(4)
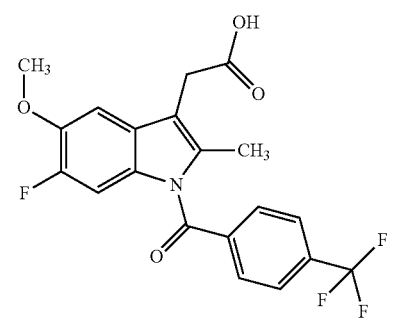
A3(5)
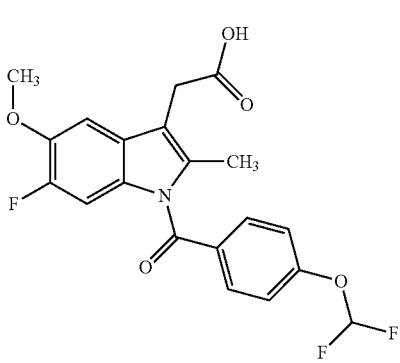
A3(6)
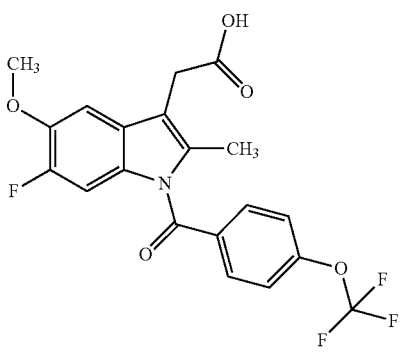
A3(7)
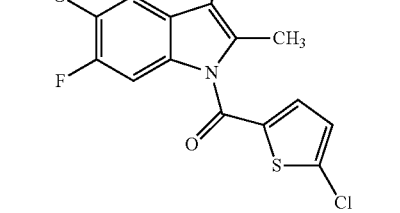
substituted 2-(1-benzyl-2-methyl-5-methoxy-6-chloro-1H-indol-3-yl)acetic acid A4(1), A4(2), substituted 2-(1-benzoyl-2-methyl-5-methoxy-6-chloro-1H-indol-3-yl)acetic acids A5(1), A5(2),
A4(1)
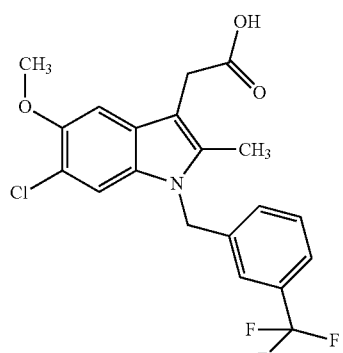
A4(2)
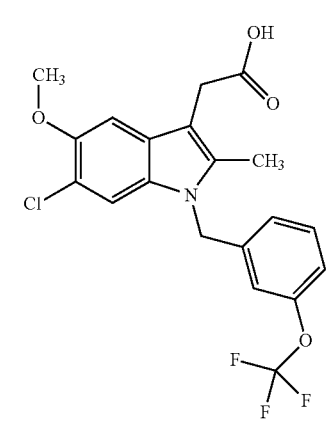
A5(1)
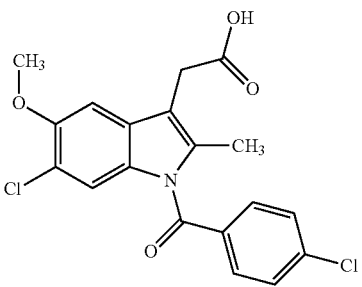
A5(2)
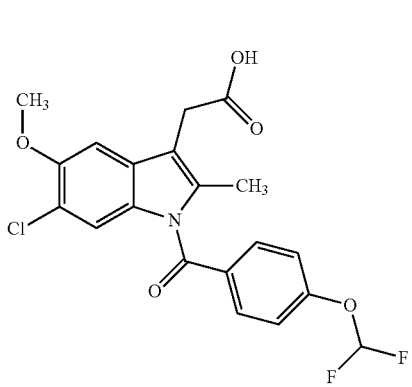
2-[1-(3-phenylacryloyl)-2-methyl-5-methoxy-1H-indol-3-yl]acetic acid esters A6(1), A6(2), A6(3),

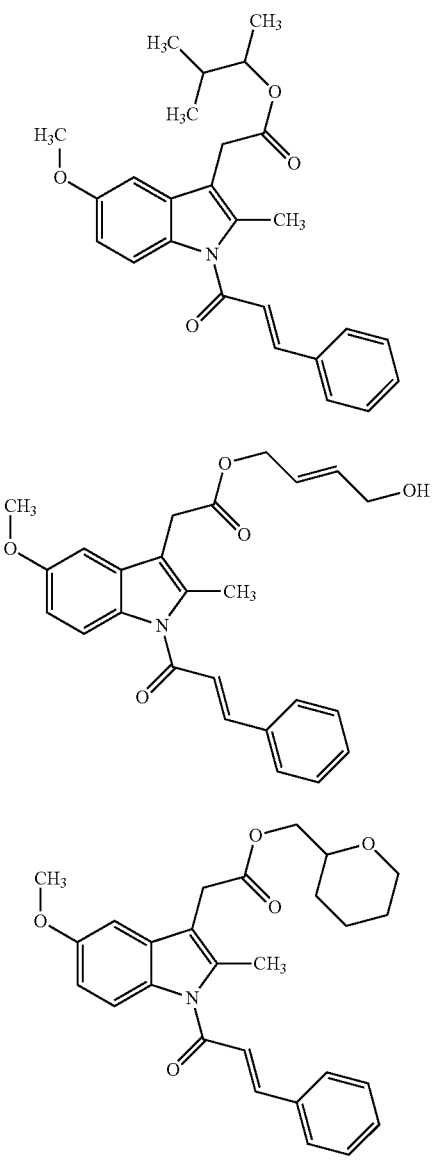
A6(1)
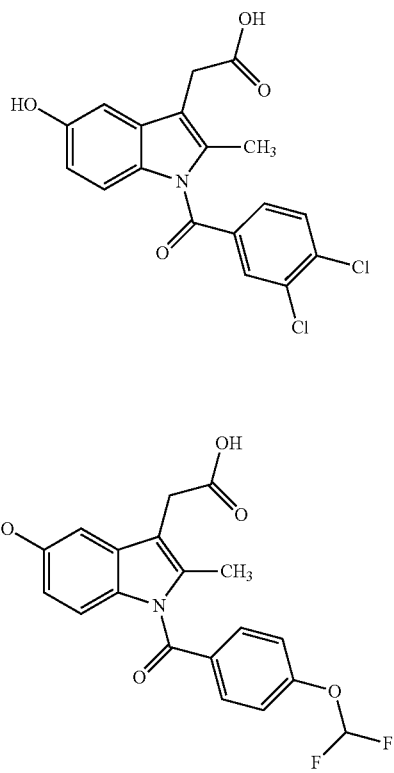
A7(2)
A6(2)
A7(3)
A6(3)
A7(4)
2-(1-benzoyl-5-hydroxy-2-methyl-1H-indol-3-yl)acetic acids A7(1), A7(2), A7(3), A7(4),
salts A10(1)-A10(4),
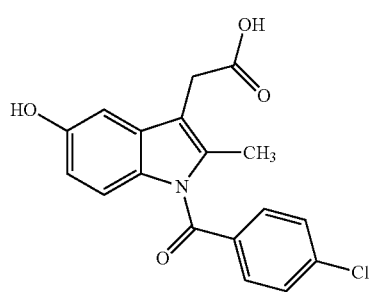
A7(1)
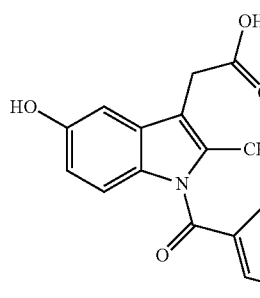
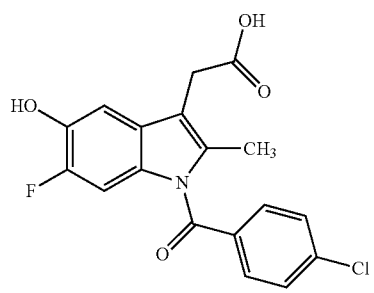
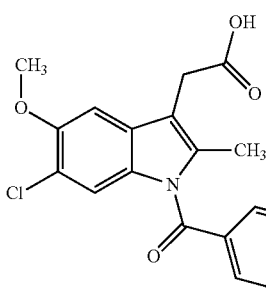
A10(1)

-continued

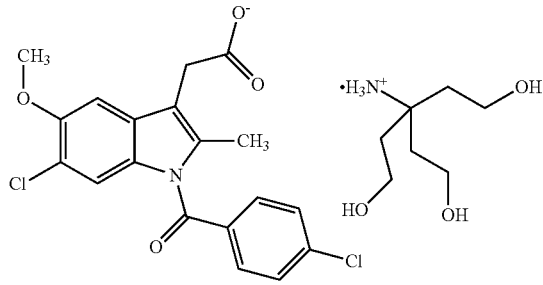
A10(2)

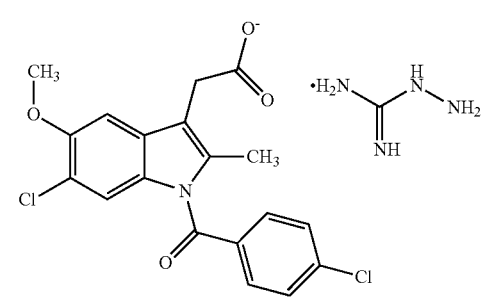
A10(3)

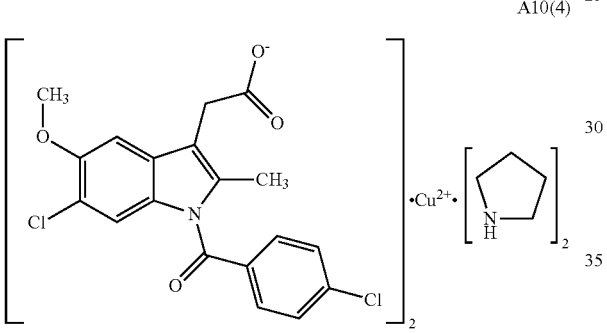
A10(4)

and substituted 2-(1-benzoyl-2-methyl-5-methoxy-1H-indol-3-yl)acetic acids and their esters of the general formula A2,

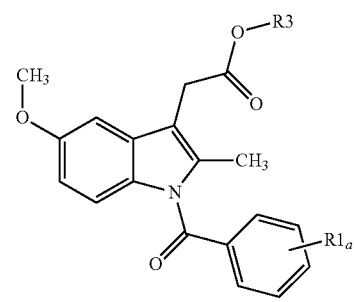
A2 wherein: R³ represents hydrogen, optionally substituted C₁-C₅ alkyl, optionally substituted aryl; R1$_a$ represents 4-F, 4-Cl, 4-CF₃, 4-CF₃O, 4-N₃, 2,4,6-Cl₃.

The preferable substituted 2-(5-hydroxy-2-methyl-1H-indol-3-yl)acetic acids are substituted 2-(5-hydroxy-2-methyl-4-fluoro-1H-indol-3-yl)acetic acids of the general formula 1.1, substituted 2-(5-hydroxy-2-methyl-6-fluoro-1H-indol-3-yl)acetic acids 1.2, substituted 2-(5-hydroxy-2-methyl-4-trifluoromethyl-1H-indol-3-yl)acetic acids 1.3, substituted 2-(5-hydroxy-2-methyl-6-trifluoromethyl-1H-indol-3-yl) acetic acids 1.4, substituted 2-(5-hydroxy-2-methyl-4-cyano-1H-indol-3-yl)acetic acids of the general formula 1.5, substituted 2-(5-hydroxy-2-methyl-6-cyano-1H-indol-3-yl)acetic acids 1.6, their esters and pharmaceutically acceptable salts and/or hydrates thereof,

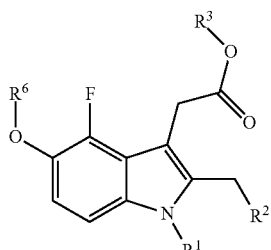
1.1

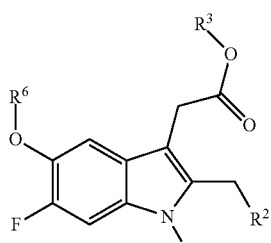
1.2

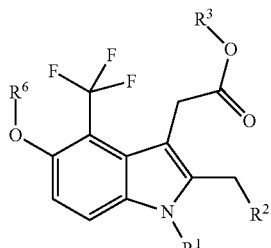
1.3

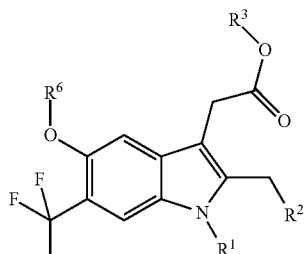
1.4

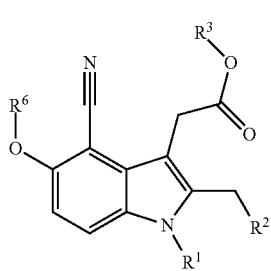
1.5

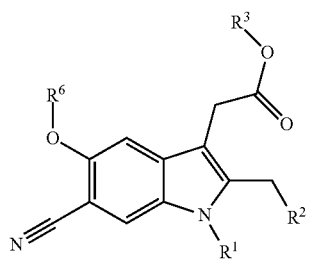

1.6 wherein: $R^1$, $R^2$, $R^3$ and $R^6$ have the above meanings

The more preferable substituted 2-(5-hydroxy-2-methyl-1H-indol-3-yl)acetic acids and esters thereof are compounds of general formulas 1.1, 1.2, 1.3, 1.4, 1.5, 1.6 and pharmaceutically acceptable salts and/or hydrates thereof in which $R^1$ represents hydrogen, methyl, 2-hydroxyethyl, 2-dimethylaminoethyl, 4-chlorobenzoyl, substituted sulfonyl, and $R^2$, $R^3$ and $R^6$ have the above meanings.

The more preferable substituted 2-(5-hydroxy-2-methyl-1H-indol-3-yl)acetic acids and their esters are also compounds of the general formulas 1.1, 1.2, 1.3, 1.4, 1.5, 1.6 and pharmaceutically acceptable salts and/or hydrates thereof in which $R^2$ are hydrogen, methyl, hydroxyl, substituted hydroxyl, dimethylaminomethyl, substituted mercapto group, and $R^1$, $R^3$ and $R^6$ have the above meanings The more preferable substituted 2-(5-hydroxy-2-methyl-1H-indol-3-yl)acetic acids and their esters are also compounds of the general formulas 1.1, 1.2, 1.3, 1.4, 1.5, 1.6 and pharmaceutically acceptable salts and/or hydrates thereof in which $R^3$ represents hydrogen, methyl or ethyl; and $R^1$, $R^2$ and $R^6$ have the above meanings The more preferable substituted 2-(5-hydroxy-2-methyl-1H-indol-3-yl)acetic acids and their esters are also compounds of the general formulas 1.1, 1.2, 1.3, 1.4, 1.5, 1.6 and pharmaceutically acceptable salts and/or hydrates thereof in which $R^6$ represents hydrogen, methyl, acetyl, isopropyl or 3-pentyl, a $R^1$, $R^2$ and $R^3$ have the above meanings.

The more preferable compounds of the general formula 1 are substituted 2-(5-hydroxy-indol-3-yl)acetic acids and their esters of the general formulas 1a and 1b, 4-substituted methyl 2-(2-methyl-6-methoxy-1H-indol-3-yl)acetates of the general formula 1c, 6-substituted methyl 2-(2-methyl-6-methoxy-1H-indol-3-yl)acetates of the general formula 1d, substituted 2-(1-acyl-indol-3-yl)acetic acids of the general formula 1e, substituted 2-(1-sulfonyl-indol-3-yl)acetic acids of the general formula 1f, substituted 2-(1-alkyl-indol-3-yl)acetic acids of the general formula 1g, substituted 2-(2-bromomethyl-1H-indol-3-yl)acetic acids of the general formula 1h, substituted 2-(2-aminomethyl-1H-indol-3-yl)acetic acids of the general formula 1i, substituted 2-(2-hydroxymethyl-1H-indol-3-yl)acetic acids of the general formulas 1k, 1l, substituted 2-(2-sulfanylmethyl-1H-indol-3-yl)acetic acids of the general formula 1m, substituted (2-(2-aminoethyl)-1H-indol-3-yl)acetic acids of the general formula 1n, substituted 2-(1H-indol-3-yl)acetic acids of the general formula 1o, substituted alkyl 2-(1H-indol-3-yl)acetates of the general formula 1p, substituted 2-(4-aminomethyl-5-hydroxy-1H-indol-3-yl) acetic acids of the general formula 1q, substituted 2-(carboxy-1H-indol-3-yl)acetic acids of the general formula 1r, substituted esters of 2-(carboxy-1H-indol-3-yl)acetic acids of the general formula 1s, substituted 2-[aryl(or hetaryl)-1H-indol-3-yl]acetic acids of the general formula 1t, substituted 2-(5-hydroxy-1H-indol-3-yl)acetic acids of the general formulas 1u, 1v, substituted 2-(5-acyloxy-1H-indol-3-yl)acetic acids of the general formulas 1w, 1x, their esters and pharmaceutically acceptable salts and/or hydrates thereof,

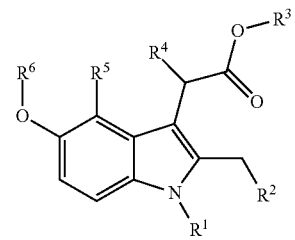

1a

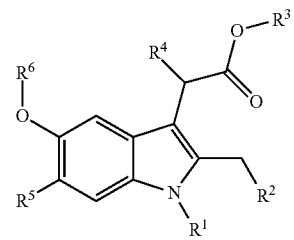

1b

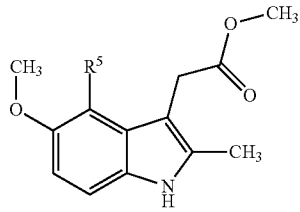

1c

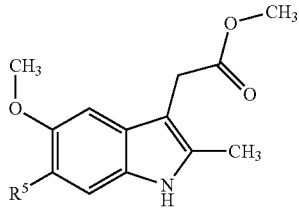

1d

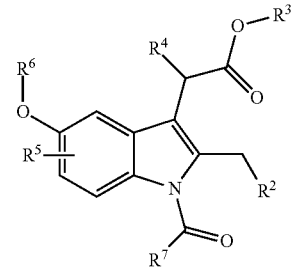

1e

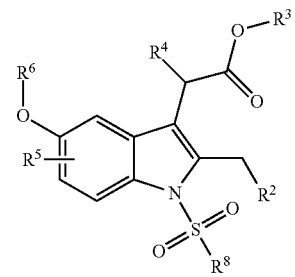

1f

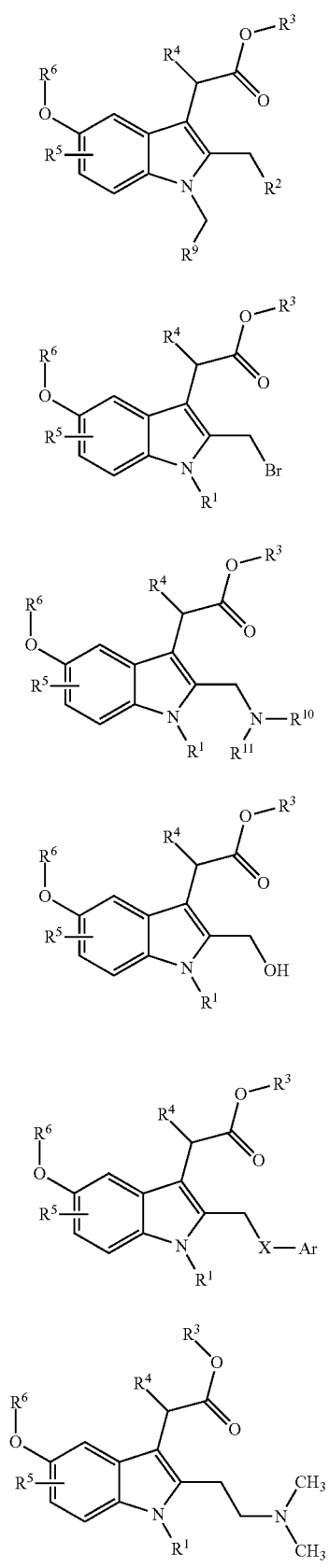
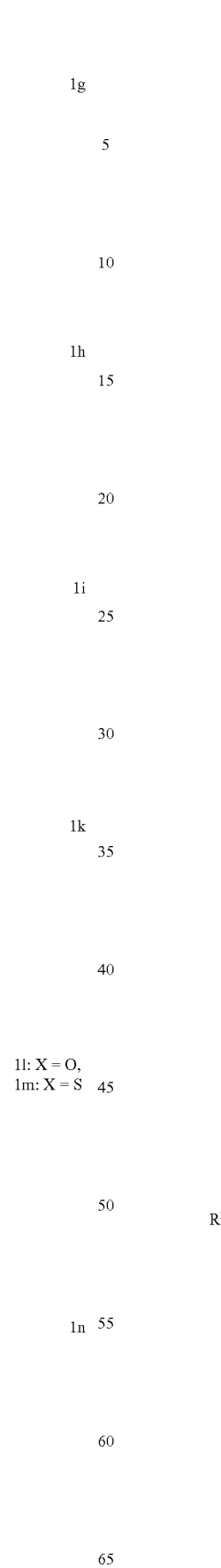

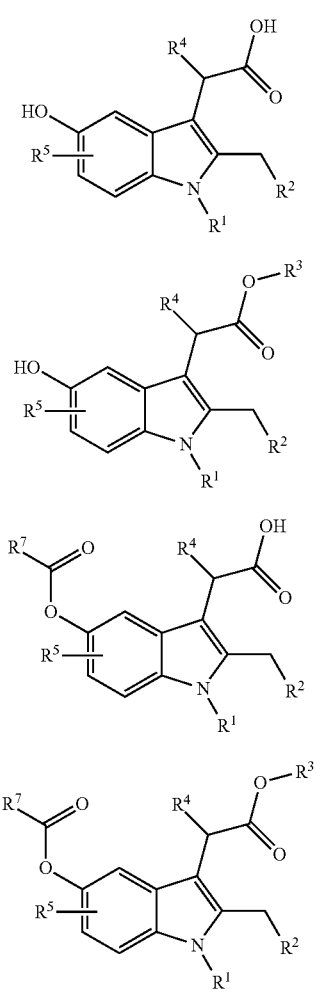

wherein: $R^1$, $R^2$, $R^3$, $R^4$, $R^5$ and $R^7$ have the above meanings, $R^8$ represents optionally substituted $C_1$-$C_3$ alkyl, aryl or heterocyclyl, $R^9$ represents hydrogen, optionally substituted $C_1$-$C_3$ alkyl, $R^{10}$ and $R^{11}$ independently of each other represent hydrogen, optionally substituted $C_1$-$C_3$ alkyl, aryl, heterocyclyl or $R^{10}$ and $R^{11}$ together with the nitrogen atom they are attached to form azaheterocyclyl.

The more preferable compounds of the general formula 1 are methyl 2-(2-methyl-5-methoxy-4-fluoro-1H-indol-3-yl)acetate 1.1(1), methyl 2-(2-methyl-5-methoxy-6-fluoro-1H-indol-3-yl)acetate 1.2(1), methyl 2-(2-methyl-5-methoxy-4-(trifluoromethyl)-1H-indol-3-yl)acetate 1.3(1), methyl 2-(2-methyl-5-methoxy-6-(trifluoromethyl)-1H-indol-3-yl) acetate 1.4(1), methyl 2-(2-methyl-5-methoxy-4-cyano-1H-indol-3-yl)acetate 1.5(1), methyl 2-(2-methyl-5-methoxy-6-cyano-1H-indol-3-y)acetate 1.6(1), methyl 2-[2-methyl-5-methoxy-4-fluoro-1-(4-chlorobenzoyl)-1H-indol-3-yl]acetate 1e(1), methyl 2-[2-methyl-5-methoxy-6-fluoro-1-(4-chlorobenzoyl)-1H-indol-3-yl]acetate 1e(2), methyl 2-[2-methyl-5-methoxy-4-(trifluoromethyl)-1-(4-chlorobenzoyl)-1H-indol-3-yl]acetate 1e(3), methyl 2-[2-methyl-5-methoxy-6-(trifluoromethyl)-1-(4-chlorobenzoyl)-1H-indol-3-yl]acetate 1e(4), 2-[2-methyl-5-methoxy-4-(trifluoromethyl)-1-(4-chlorobenzoyl)-1H-indol-3-yl]acetic acid 1e(5), 2-[2-methyl-5-methoxy-6-(trifluoromethyl)-1-(4-chlorobenzoyl)-1H-indol-3-yl]acetic acid 1e(6), methyl 2-[2-methyl-5-methoxy-1-(4-chlorobenzoyl)-4-cyano-1H-indol-3-yl]acetate 1e(7), methyl 2-[2-methyl-5-methoxy-1-(4-chlorobenzoyl)-6-cyano-1H-indol-3-yl]acetate 1e(8), methyl 2-[2-methyl-5-methoxy-6-fluoro-1-(p-tolylsulfonyl)-1H-indol-3-yl]acetate 1f(1), methyl 2-(2-methyl-5-methoxy-6-(trifluoromethyl)-1-phenylsulfonyl-1H-indol-3-yl)acetate 1f(2), methyl 2-[2-methyl-5-methoxy-6-(trifluoromethyl)-1-(pyridin-3-ylsulfonyl)-1H-indol-3-yl] acetate 1f(3), methyl 2-(2-methyl-5-methoxy-1-(methylsulfonyl)-6-(trifluoromethyl)-1H-indol-3-yl)acetate 1f(4), methyl 2-(1-(benzolsulfonyl)-2-methyl-5-methoxy-6-(trifluoromethyl)-1H-indol-3-yl)acetate 1f(5), methyl 2-(1,2-dimethyl-5-methoxy-4-fluoro-1H-indol-3-yl)acetate 1g(1), methyl 2-(1,2-dimethyl-5-methoxy-6-fluoro-1H-indol-3-yl)acetate 1g(2), methyl 2-(1,2-dimethyl-5-methoxy-4-(trifluoromethyl)-1H-indol-3-yl)acetate 1g(3), methyl 2-(1,2-dimethyl-5-methoxy-6-(trifluoromethyl)-1H-indol-3-yl)acetate 1g(4), ethyl 2-(1-ethyl-5-methoxy-2-methyl-6-(trifluoromethyl)-1H-indol-3-yl)butanoate 1g(5), methyl 2-(1,2-dimethyl-5-methoxy-4-cyano-1H-indol-3-yl)acetate 1g(6), methyl 2-(1,2-dimethyl-5-methoxy-6-cyano-1H-indol-3-yl) acetate 1g(7), methyl 2-[1-(2-hydroxyethyl)-2-methyl-5-methoxy-4-fluoro-1H-indol-3-yl]acetate 1g(8), methyl 2-[1-(2-hydroxyethyl)-2-methyl-5-methoxy-6-fluoro-1H-indol-3-yl]acetate 1g(9), methyl 2-[1-(2-hydroxyethyl)-2-methyl-5-methoxy-4-(trifluoromethyl)-1H-indol-3-yl]acetate 1g(10), methyl 2-[1-(2-hydroxyethyl)-2-methyl-5-methoxy-6-(trifluoromethyl)-1H-indol-3-yl]acetate 1g(11), methyl 2-[1-(2-(dimethylamino)ethyl)-2-methyl-5-methoxy-4-fluoro-1H-indol-3-yl]acetate 1g(12), methyl 2-[1-(2-(dimethylamino)ethyl)-2-methyl-5-methoxy-6-fluoro-1H-indol-3-yl]acetate 1g(13), methyl 2-[1-(2-(dimethylamino)ethyl)-2-methyl-5-methoxy-4-(trifluoromethyl)-1H-indol-3-yl] acetate 1g(14), methyl 2-[1-(2-(dimethylamino)ethyl)-2-methyl-5-methoxy-6-(trifluoromethyl)-1H-indol-3-yl] acetate 1g(15), methyl 2-[1-(2-(dimethylamino)ethyl)-2-methyl-5-methoxy-4-cyano-1H-indol-3-yl]acetate 1g(16), methyl 2-[1-(2-(dimethylamino)ethyl)-2-methyl-5-methoxy-6-cyano-1H-indol-3-yl]acetate 1g(17), 2-[1-(2-hydroxyethyl)-2-methyl-5-methoxy-6-(trifluoromethyl)-1H-indol-3-yl]acetic acid 1g(18), 2-[1-(2-(dimethylamino)ethyl)-2-methyl-5-methoxy-6-(trifluoromethyl)-1H-indol-3-yl]acetic acid 1g(19), 2-[2-(dimethylamino)methyl-5-methoxy-1-(4-chlorobenzoyl)-1H-indol-3-yl]acetic acid 1i(1), methyl 2-[2-(dimethylamino)methyl-5-methoxy-6-fluoro-1-(4-chlorobenzoyl)-1H-indol-3-yl]acetate 1i(2), 2-[2-(dimethylamino)methyl-5-methoxy-6-fluoro-1-(4-chlorobenzoyl)-1H-indol-3-yl]acetic acid 1i(3), methyl 2-[2-(dimethylamino)methyl-5-methoxy-6-(trifluoromethyl)-1-(4-chlorobenzoyl)-1H-indol-3-yl]acetate 1i(4), 2-[2-(dimethylamino)methyl-5-methoxy-6-(trifluoromethyl)-1-(4-chlorobenzoyl)-1H-indol-3-yl]acetic acid 1i(5), methyl 2-[2-(dimethylamino)methyl-5-methoxy-4-(trifluoromethyl)-1-(4-chlorobenzoyl)-1H-indol-3-yl]acetate 1i(6), 2-[2-(dimethylamino)methyl-5-methoxy-4-(trifluoromethyl)-1-(4-chlorobenzoyl)-1H-indol-3-yl]acetic acid 1i(7), methyl 2-(2-(dimethylamino)methyl-5-methoxy-4-fluoro-1H-indol-3-yl)acetate 1i(8), 2-(2-(dimethylamino)methyl-5-methoxy-4-fluoro-1H-indol-3-yl)acetic acid 1i(9), methyl 2-(2-(dimethylamino)methyl-5-methoxy-4-(trifluoromethyl)-1H-indol-3-yl)acetate 1i(10), 2-(2-(dimethylamino)methyl-5-methoxy-4-(trifluoromethyl)-1H-indol-3-yl)acetic acid 1i(11), methyl 2-(2-(dimethylamino)methyl-1-methyl-5-methoxy-4-fluoro-indol-3-yl)acetate 1i(12), 2-(2-(dimethylamino)methyl-1-methyl-5-methoxy-4-fluoro-1H-indol-3-yl)acetic acid 1i(13), methyl 2-(2-(dimethylamino)methyl-1-methyl-5-methoxy-4-(trifluoromethyl)-1H-indol-3-yl)acetate 1i(14), 2-(2-(dimethylamino)methyl-1-methyl- 5-methoxy-4-(trifluoromethyl)-1H-indol-3-yl)acetic acid 1i(15), methyl 2-(2-(dimethylamino)methyl-5-methoxy-6-fluoro-1H-indol-3-yl)acetate 1i(16), methyl 2-(2-(dimethylamino)methyl-5-methoxy-6-(trifluoromethyl)-1H-indol-3-yl)acetate 1i(17), 2-(2-(dimethylamino)methyl-5-methoxy-6-(trifluoromethyl)-1H-indol-3-yl)acetic acid 1i(18), 2-(2-(dimethylamino)methyl-5-methoxy-6-fluoro-1H-indol-3-yl)acetic acid 1i(19), methyl 2-(2-(dimethylamino)methyl-1-methyl-5-methoxy-6-fluoro-1H-indol-3-yl)acetate 1i(20), methyl 2-(2-(dimethylamino)methyl-1-methyl-5-methoxy-6-(trifluoromethyl)-1H-indol-3-yl)acetate 1i(21), 2-(2-(dimethylamino)methyl-1-methyl-5-methoxy-6-fluoro-1H-indol-3-yl)acetic acid 1i(22), 2-(2-(dimethylamino)methyl-1-methyl-5-methoxy-6-(trifluoromethyl)-1H-indol-3-yl)acetic acid 1i(23), 2-(5-acetyloxy-2-(dimethylamino)methyl-1-methyl-6-phenyl-1H-indol-3-yl)acetic acid 1i(24), 2-(5-acetyloxy)-2-(dimethylamino)methyl-1-methyl-6-(pyridin-3-yl)-1H-indol-3-yl)acetic acid 1i(25), 2-[2-(hydroxymethyl)-5-methoxy-1-(4-chlorobenzoyl)-1H-indol-3-yl]acetic acid 1k(1), 2-[5-methoxy-2-(phenyloxymethyl)-1-(4-chlorobenzoyl)-1H-indol-3-yl]acetic acid 1l(1), methyl 2-[1-methyl-5-methoxy-2-((4-chlorophenyloxy)methyl)-1H-indol-3-yl]acetate 1l(2), methyl 2-(1-methyl-5-methoxy-6-fluoro-2-(phenylsulfanylmethyl)-1H-indol-3-yl)acetate 1m(1), methyl 2-[1-methyl-5-methoxy-6-fluoro-2-(pyridin-3-ylsulfanylmethyl)-1H-indol-3-yl]acetate 1m(2), methyl 2-[2-(2-dimethylamino)ethyl-1-methyl-5-methoxy-6-fluoro-1H-indol-3-yl]acetate 1n(1), methyl 2-[2-(2-dimethylamino)ethyl-1-methyl-5-methoxy-6-(trifluoromethyl)-1H-indol-3-yl]acetate 1n(2), 2-(2-methyl-5-methoxy-4-fluoro-1H-indol-3-yl)acetic acid 1o(1), 2-(2-methyl-5-methoxy-6-fluoro-1H-indol-3-yl)acetic acid 1o(2), 2-(2-methyl-5-methoxy-4-(trifluoromethyl)-1H-indol-3-yl)acetic acid 1o(3), 2-(2-methyl-5-methoxy-6-(trifluoromethyl)-1H-indol-3-yl)acetic acid 1o(4), 2-(1,2-dimethyl-5-methoxy-6-(trifluoromethyl)-1H-indol-3-yl)acetic acid 1o(5), 2-(1,2-dimethyl-5-methoxy-6-fluoro-1H-indol-3-yl)acetic acid 1o(6), 2-(1,2-dimethyl-5-methoxy-4-(trifluoromethyl)-1H-indol-3-yl)acetic acid 1o(7), methyl [2-(1,2-dimethyl-5-methoxy-6-(trifluoromethyl)-1H-indol-3-yl]propionate 1p(1), methyl 2-(1,2-dimethyl-5-methoxy-6-(trifluoromethyl)-1H-indol-3-yl)-4-dimethylaminobutyrate 1p(2), methyl 2-(1,2-dimethyl-5-methoxy-6-(trifluoromethyl)-1H-indol-3-yl)-3-phenylpropionate 1p(3), methyl 2-(1,2-dimethyl-5-methoxy-6-fluoro-1H-indol-3-yl)-3-(pyridin-3-yl)propionate 1p(4), methyl 2-(5-hydroxy-4-(dimethylamino)methyl-2-methyl-6-fluoro-1H-indol-3-yl)acetate 1q(1), methyl 2-(5-hydroxy-1,2-dimethyl-4-(dimethylamino)methyl-6-fluoro-1H-indol-3-yl)acetate 1q(2), 2-[2,4-bis(dimethylaminomethyl)-1-methyl-5-hydroxy-6-(pyridin-3-yl)-1H-indol-3-yl]acetic acid 1q(3), 2-(1,2-dimethyl-5-hydroxy-6-carboxy-1H-indol-3-yl)acetic acid 1r(1), methyl 2-(1,2-dimethyl-5-hydroxy-6-(methyloxycarbonyl)-1H-indol-3-yl)acetate 1s(1), 2-(1,2-dimethyl-5-methoxy-4-(pyridin-4-yl)-1H-indol-3-yl)acetic acid 1 t(1), 2-(1,2-dimethyl-5-methoxy-4-phenyl-1H-indol-3-yl)acetic acid 1t(2), methyl 2-[1,2-dimethyl-5-methoxy-6-(4-fluorophenyl)-1H-indol-3-yl]acetate 1t(3), methyl 2-(1,2-dimethyl-5-methoxy-6-(pyridin-3-yl)-1H-indol-3-yl)acetate 1t(4), 2-(5-hydroxy-2-(dimethylamino)methyl-1-methyl-6-(pyridin-3-yl)-1H-indol-3-yl)acetic acid 1t(5), 2-[1,2-dimethyl-5-hydroxy-6-(4-fluorophenyl)-1H-indol-3-yl]acetic acid 1u(1), 2-(1,2-dimethyl-5-hydroxy-6-(pyridin-3-yl)-1H-indol-3-yl)acetic acid 1u(2), 2-(5-hydroxy-2-methyl-4-fluoro-1H-indol-3-yl)acetic acid 1u(3), 2-(5-hydroxy-2-methyl-6-fluoro-1H-indol-3-yl)acetic acid 1u(4), 2-(5-hydroxy-1,2-dimethyl-4-fluoro-1H-indol-3-yl)acetic acid 1u(5), 2-(5-hydroxy-1,2-dimethyl-6-fluoro-1H-indol-3-yl)acetic acid 1u(6), 2-[5-hydroxy-1-(2-hydroxyethyl)-2-methyl-4-fluoro-1H-indol-3-yl]acetic acid 1u(7), 2-[5-hydroxy-1-(2-hydroxyethyl)-2-methyl-6-fluoro-1H-indol-3-yl]acetic acid 1u(8), 2-[5-hydroxy-1-(2-dimethylamino ethyl)-2-methyl-4-fluoro-1H-indol-3-yl]acetic acid 1u(9), 2-[5-hydroxy-1-(2-dimethylaminoethyl)-2-methyl-6-fluoro-1H-indol-3-yl]acetic acid 1u(10), methyl 2-(5-hydroxy-1,2-dimethyl-6-fluoro-1H-indol-3-yl)acetate 1v(1), methyl 2-(5-hydroxy-2-methyl-4-fluoro-1H-indol-3-yl)acetate 1v(2), methyl 2-(5-hydroxy-2-methyl-6-fluoro-1H-indol-3-yl)acetate 1v(3), methyl 2-(5-hydroxy-1,2-dimethyl-4-fluoro-1H-indol-3-yl)acetate 1v(4), methyl 2-[5-hydroxy-1-(2-hydroxyethyl)-2-methyl-4-fluoro-1H-indol-3-yl]acetate 1v(5), methyl 2-[5-hydroxy-1-(2-hydroxyethyl)-2-methyl-6-fluoro-1H-indol-3-yl]acetate 1v(6), methyl 2-[5-hydroxy-1-(2-dimethylamino)ethyl-2-methyl-4-fluoro-1H-indol-3-yl]acetate 1v(7), methyl 2-[5-hydroxy-1-(2-dimethylamino)ethyl-2-methyl-6-fluoro-1H-indol-3-yl]acetate 1v(8), 2-(5-acetyloxy-1,2-dimethyl-6-fluoro-1H-indol-3-yl)acetic acid 1w(1), methyl 2-(5-acetyloxy-1,2-dimethyl-4-fluoro-1H-indol-3-yl)acetate 1x(1), methyl 2-(5-acetyloxy-2-methyl-4-(trifluoromethyl)-1H-indol-3-yl)acetate 1x(2) and pharmaceutically acceptable salts and/or hydrates thereof,

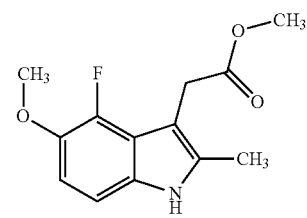

1.1(1)

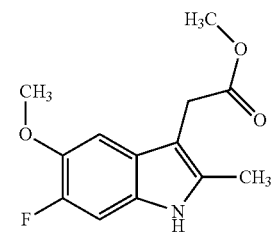

1.2(1)

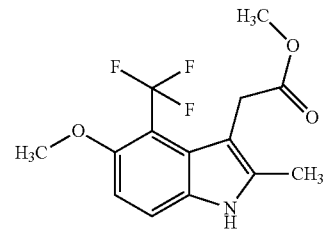

1.3(1)

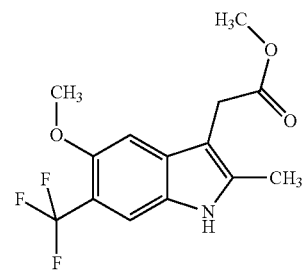

1.4(1)

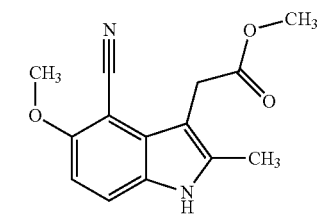
1.5(1)
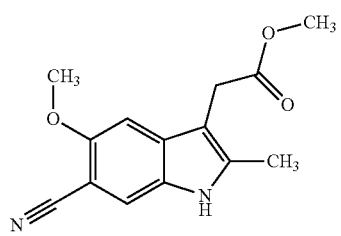
1.6(1)
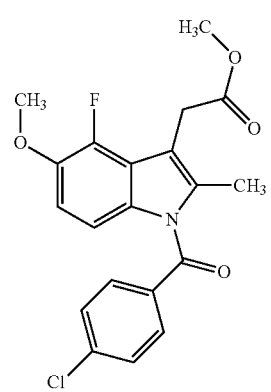
1e(1)
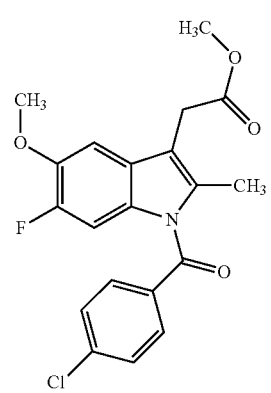
1e(2)
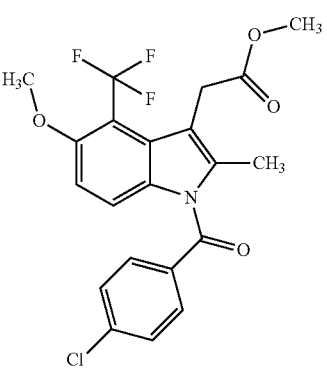
1e(3)
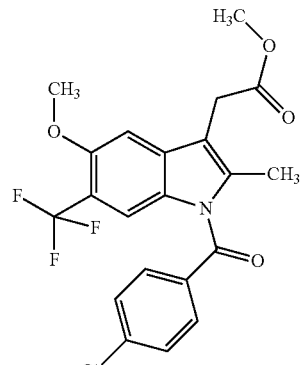
1e(4)
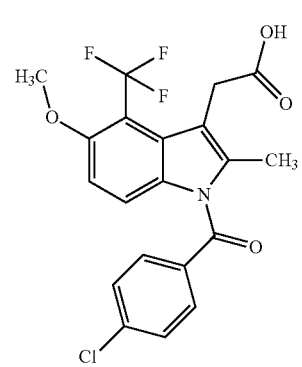
1e(5)
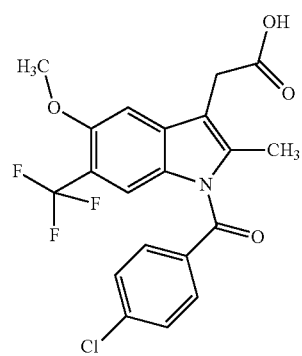
1e(6)
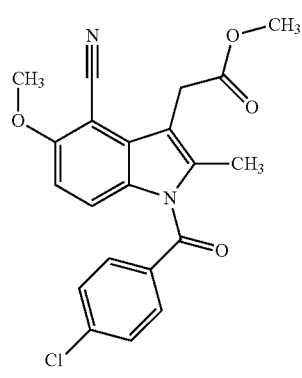
1e(7)

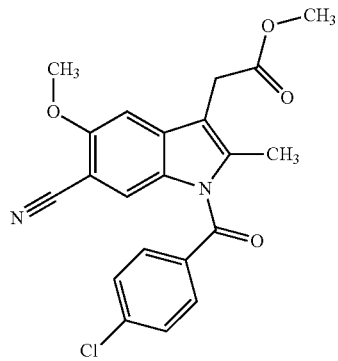
1e(8)
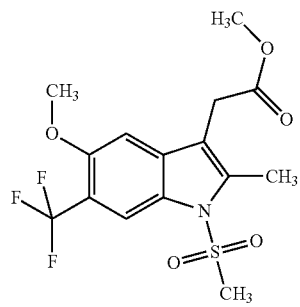
1f(4)
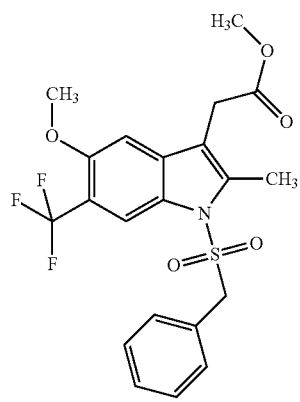
1f(1)
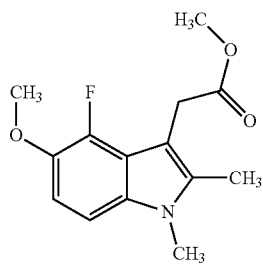
1f(5)
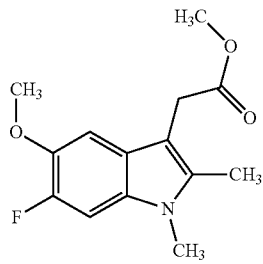
1f(2)
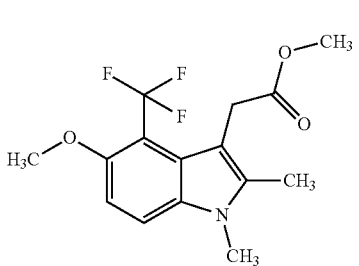
1g(1)
1f(3)
1g(2)
1g(3)

1g(4)
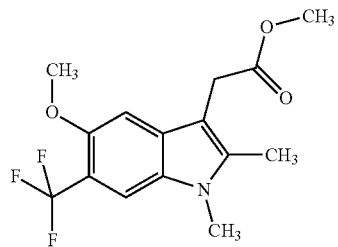
1g(5)
1g(6)
1g(7)
1g(8)
1g(9)
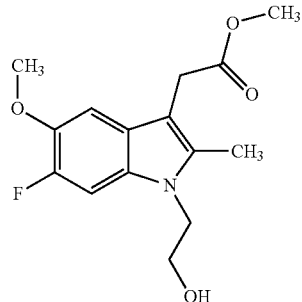
1g(10)
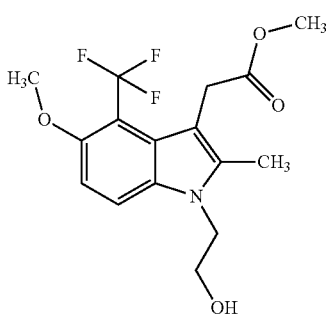
1g(11)
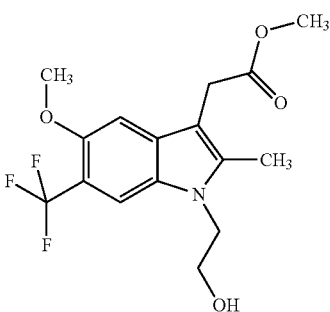
1g(12)
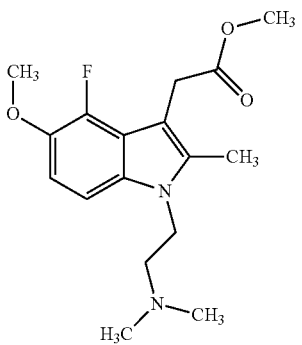
1g(13)
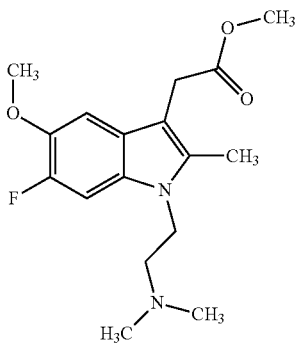

-continued
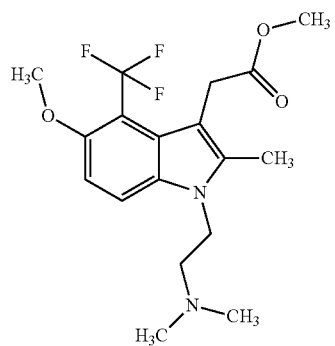
1g(14)
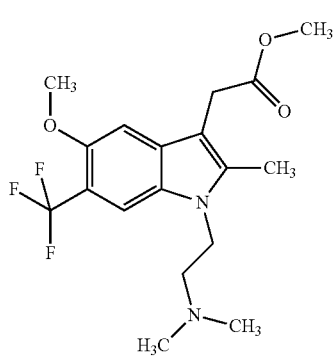
1g(15)
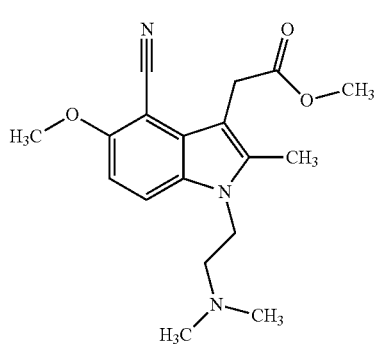
1g(16)
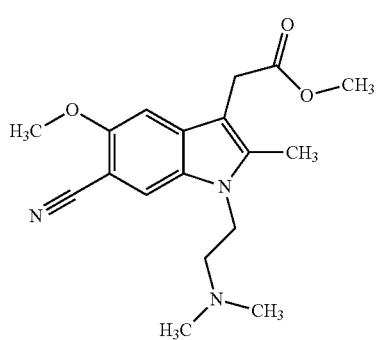
1g(17)
-continued
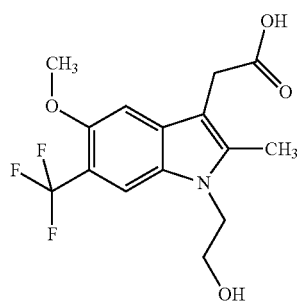
1g(18)
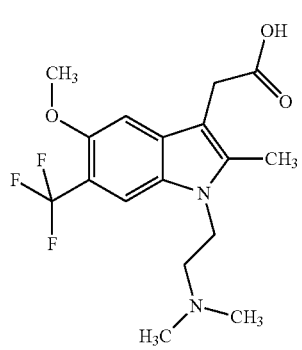
1g(19)
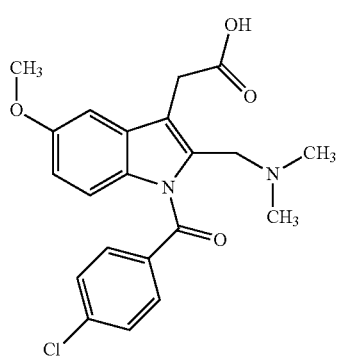
1i(1)
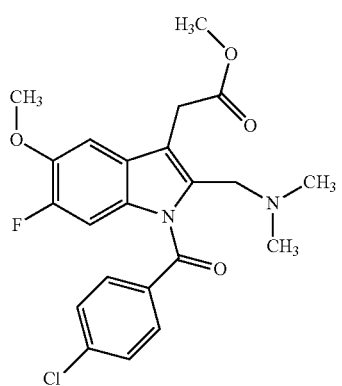
1i(2)

1i(3)
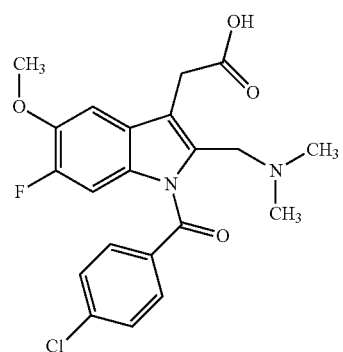
1i(4)
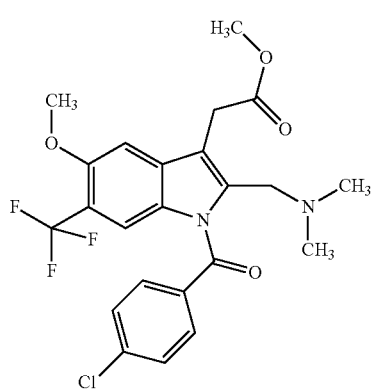
1i(5)
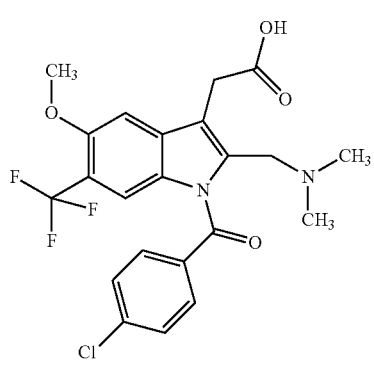
1i(6)
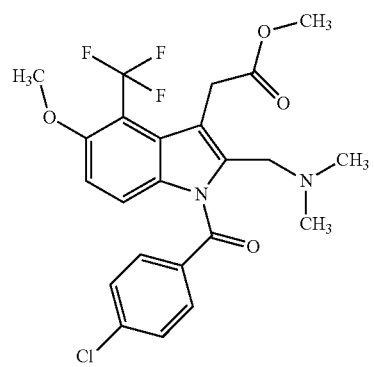
1i(7)
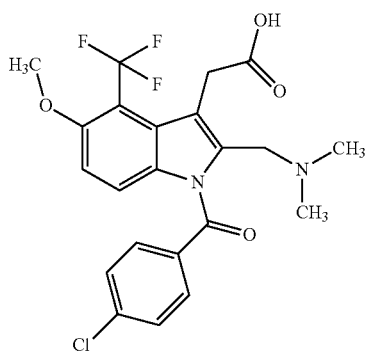
1i(8)
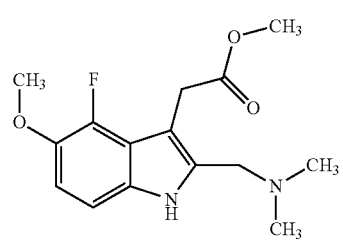
1i(9)
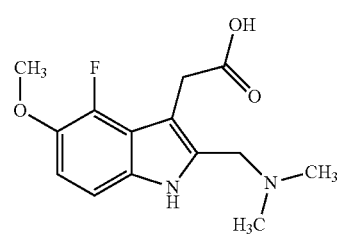
1i(10)
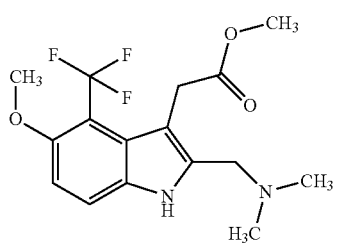
1i(11)
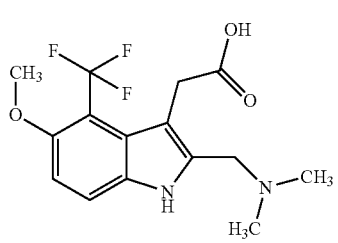
1i(12)
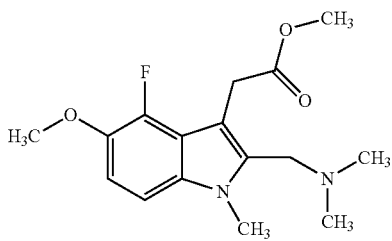

1i(13)

1i(14)

1i(15)

1i(16)

1i(17)

1i(18)

1i(19)

1i(20)

1i(21)

1i(22)

1i(23)

1i(24)

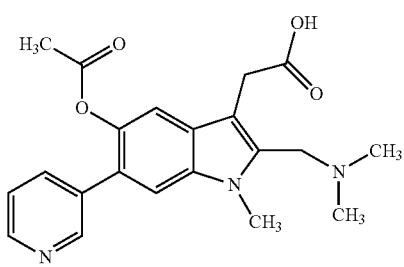 1i(25)
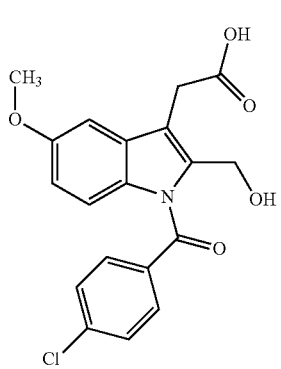 1k(1)
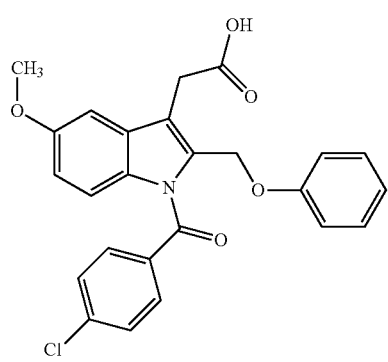 1l(1)
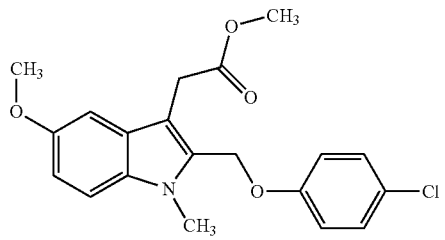 1l(2)
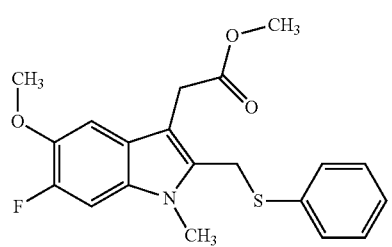 1m(1)
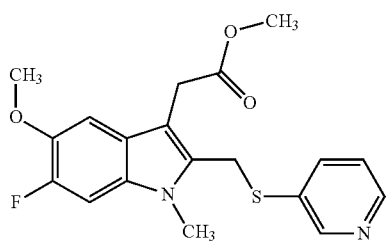 1m(2)
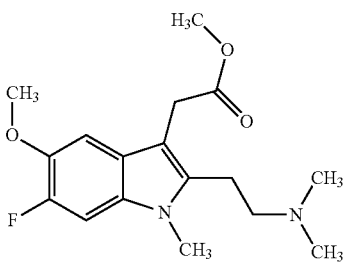 1n(1)
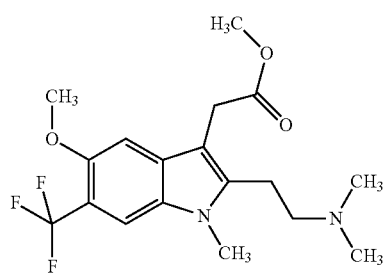 1n(2)
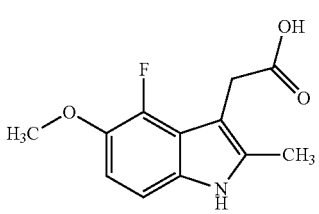 1o(1)
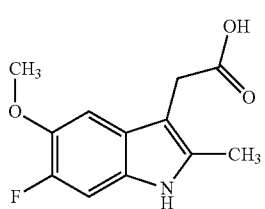 1o(2)
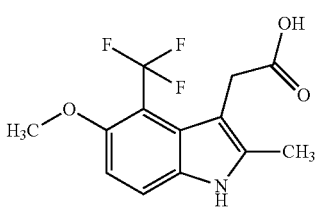 1o(3)

1o(4)
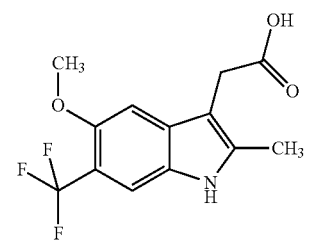
1o(5)
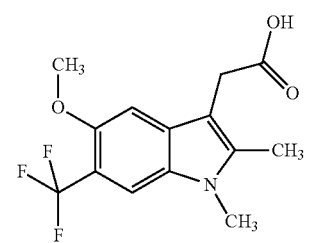
1o(6)
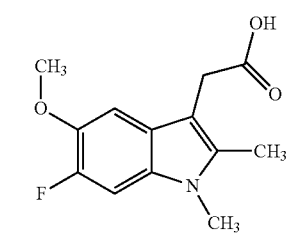
1o(7)
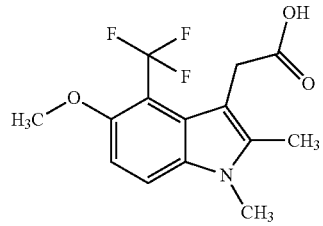
1p(1)
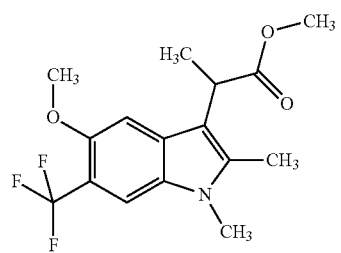
1p(2)
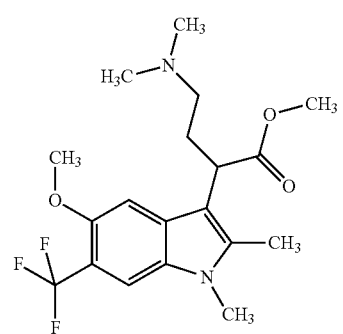
1p(3)
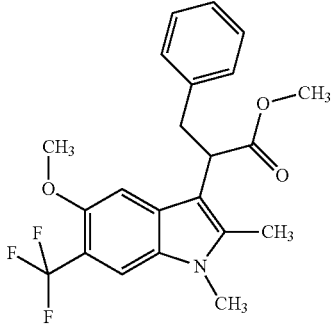
1p(4)
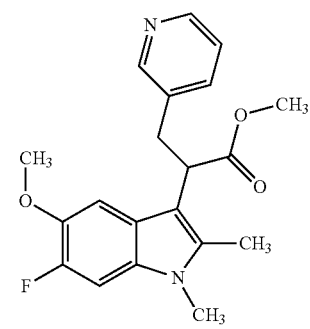
1q(1)
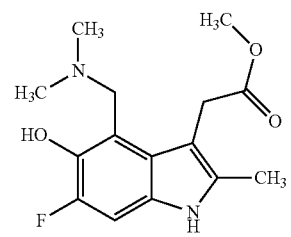
1q(2)
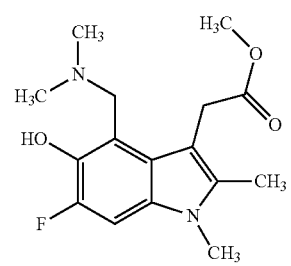
1q(3)
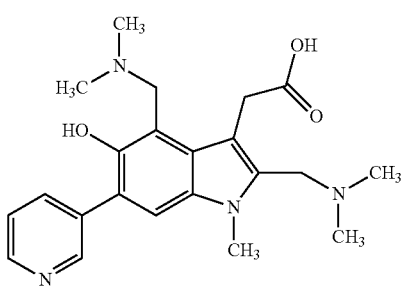

1r(1)
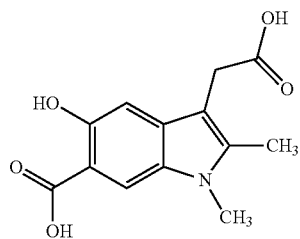
1s(1)
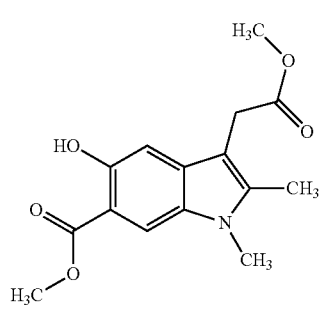
1t(1)
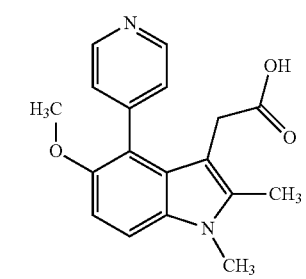
1t(2)
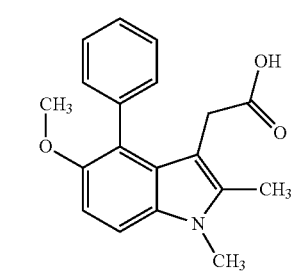
1t(3)
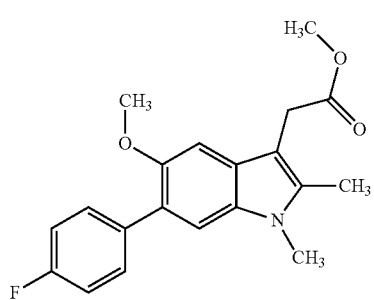
1t(4)
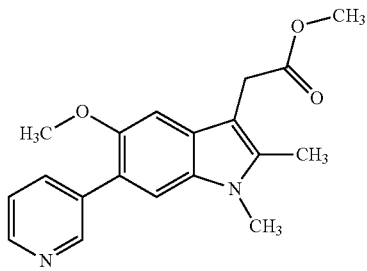
1t(5)
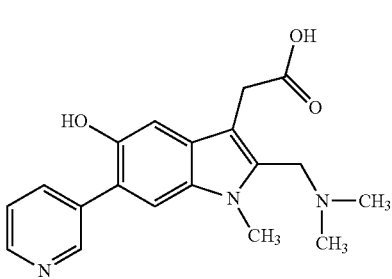
1u(1)
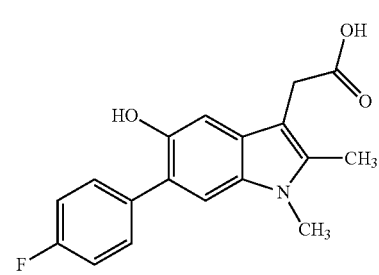
1u(2)
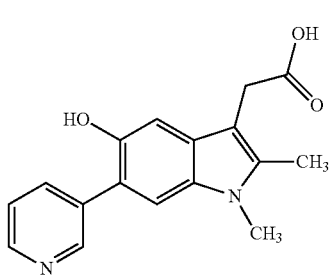
1u(3)
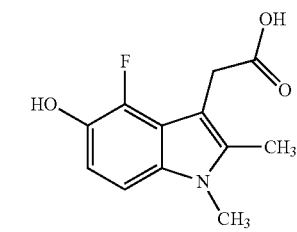
1u(4)
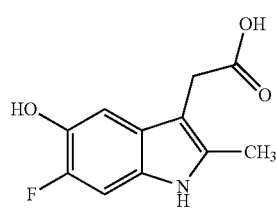

1u(5)
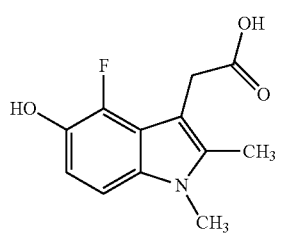
1u(6)
1u(7)
1u(8)
1u(9)
1u(10)
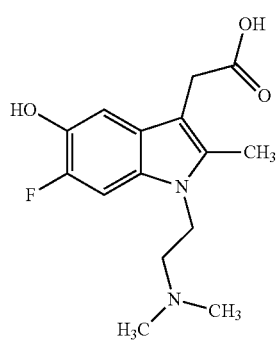
1v(1)
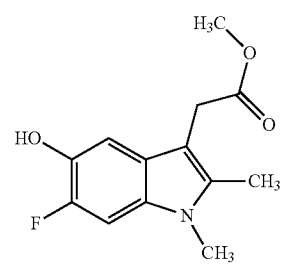
1v(2)
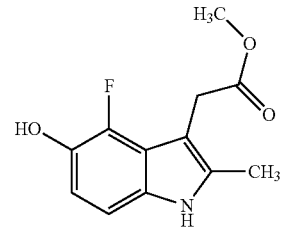
1v(3)
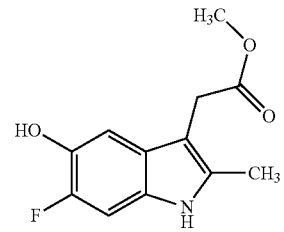
1v(4)
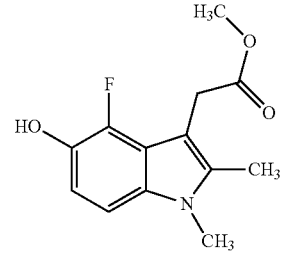

1v(5)
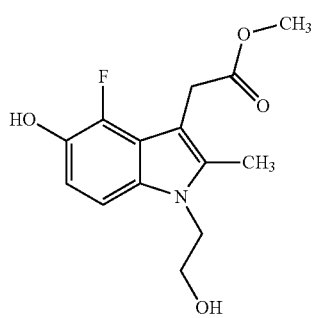

1v(6)
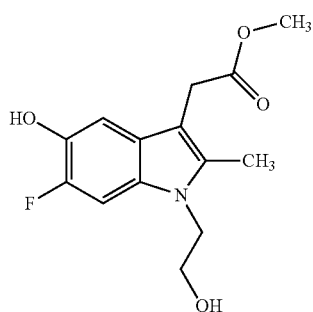

1v(7)
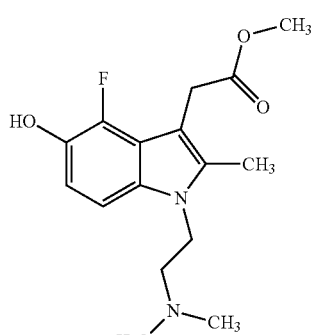

1v(8)
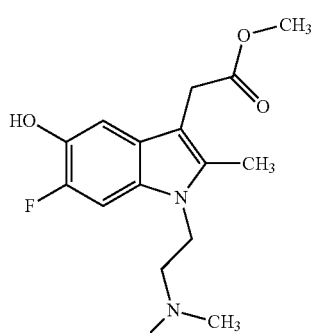

1w(1)
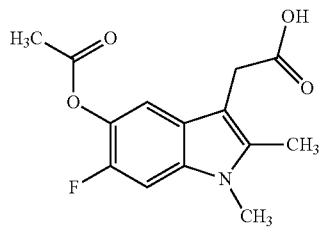

1x(1)
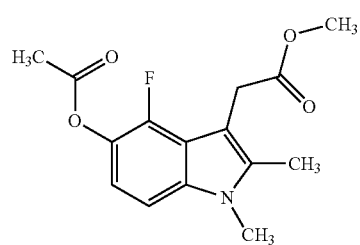

1x(2)
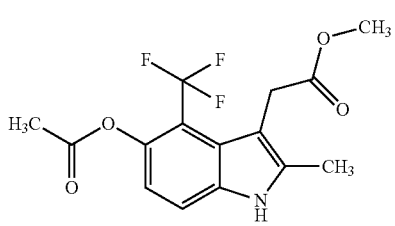

Methods for the preparation of novel substituted 2-(5-hydroxy-2-methyl-1H-indol-3-yl)acetic acids and their esters of the general formula 1 and pharmaceutically acceptable salts and/or hydrates thereof are also the subject of the present invention, they are illustrated by the following schemes.

According to the invention substituted 2-(1H-indol-3-yl)acetic acids of the general formula 1 could be prepared by interaction of the corresponding substituted phenylhydrazines of the general formula 2 with substituted levulinic acids of the general formula 3 at heating in acetic acid according to the scheme given below:

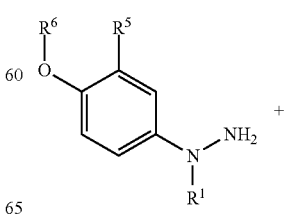

2

-continued

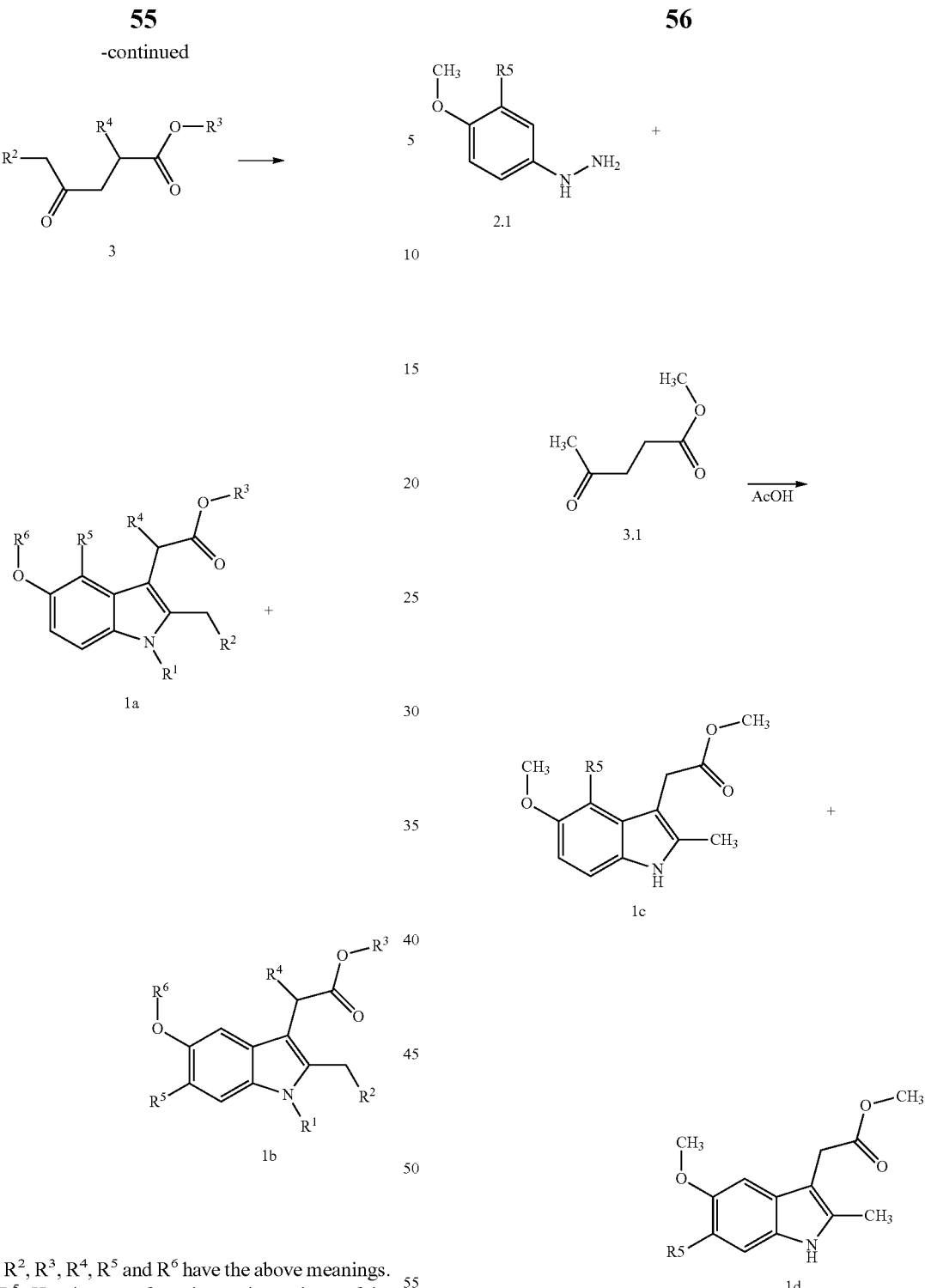

wherein: $R^1$, $R^2$, $R^3$, $R^4$, $R^5$ and $R^6$ have the above meanings. As a rule, if $R^5 \neq H$, mixtures of two isomeric products of the general formulas 1a and 1b with various ratio of components are obtained, which can be separated or purified by conventional methods.

According to the invention substituted 2-(2-methyl-5-methoxy-1H-indol-3-yl)acetic acids of the general formulas 1c, 1d where $R^1=R^2=H$, $R^3=R^6=CH_3$, $R^4=H$ are prepared by interaction of the corresponding 3-substituted 4-methoxyphenylhydrazines of the general formula 2.1 with methyl ester of levulinic acid 3.1 at heating in acetic acid with the subsequent isolation of the reaction products according to the scheme given below:

wherein: $R^5=F$, $CF_3$, CN.

According to the invention 1-substituted 2-(1H-indol-3-yl) acetic acids of the general formulas 1e, 1f, 1g are prepared by interaction of the corresponding compounds of the general formula 1 where $R^1=H$ with acyl chlorides 4, sulfonyl chlorides 5 or alkyl halides 6 according to the schemes given below:

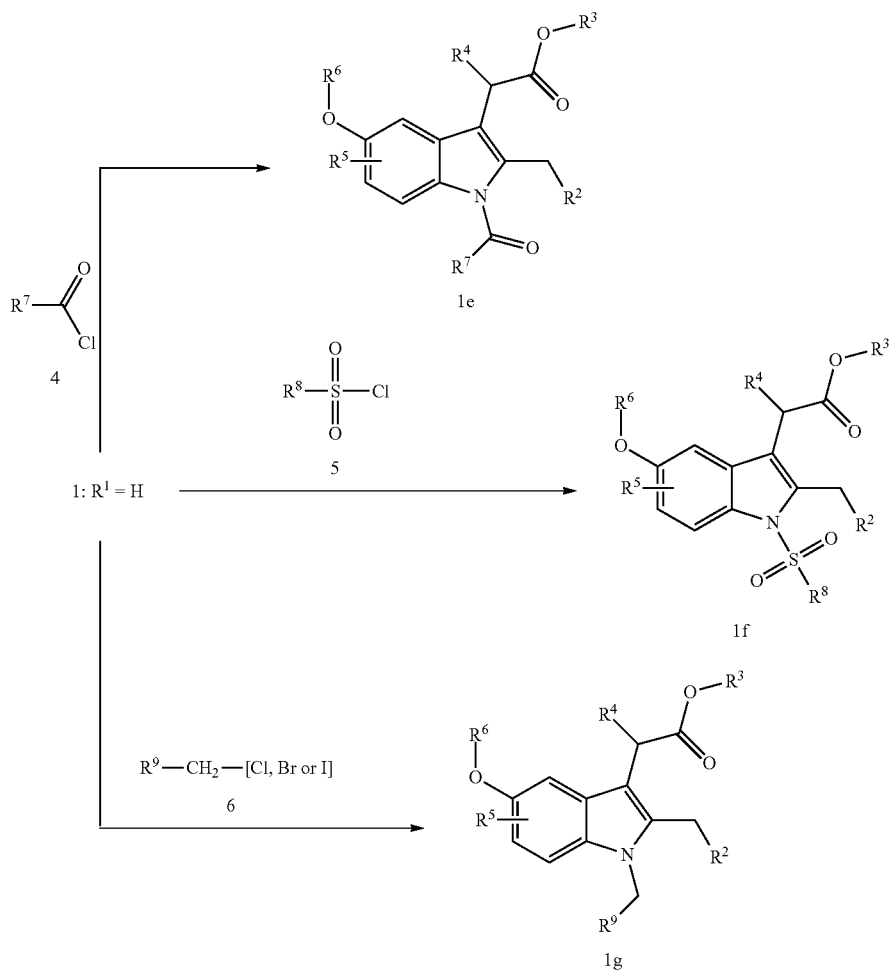

wherein: $R^1$=H; $R^2$, $R^3$, $R^4$, $R^5$ and $R^6$ have the above meanings; $R^7$ represents optionally substituted $C_1$-$C_3$ alkyl, aryl, heterocyclyl; $R^8$ represents optionally substituted $C_1$-$C_3$ alkyl, aryl or heterocyclyl, $R^9$ represents hydrogen, optionally substituted methyl.

According to the invention 2-aminomethyl-derivatives of the general formula 1i are prepared by bromination of the corresponding 2-methyl-derivatives of the general formula 1 ($R^2$=H) with subsequent interaction of the resulting 2-bromomethyl-derivatives of the general formula 1h with primary or secondary amines of the general formula 7 according to the scheme given below:

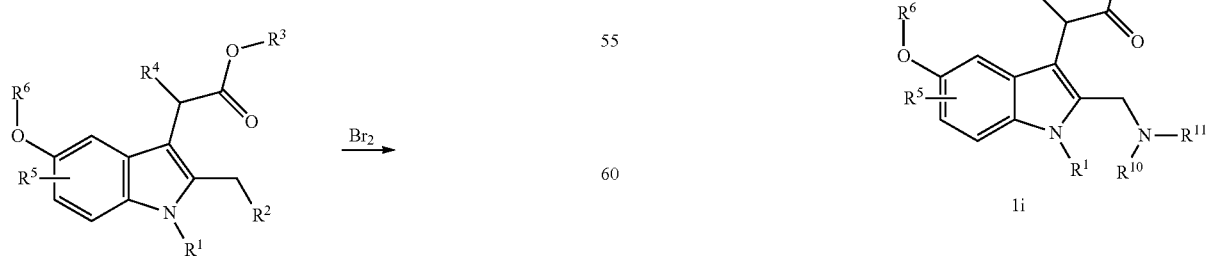

wherein: $R^1$, $R^3$, $R^4$, $R^5$ and $R^6$ have the above meanings; $R^{10}$ and $R^{11}$ independently of each other represent hydrogen, optionally substituted $C_1$-$C_3$ alkyl, aryl, heterocyclyl or $R^{10}$ and $R^{11}$ together with the nitrogen atom they are attached to form an azaheterocyclyl.

According to the invention 2-hydroxymethyl-derivatives of the general formula 1k are prepared by interaction of 2-bromomethyl-derivatives of the general formula 1h with sodium hydroxide according to the scheme given below:

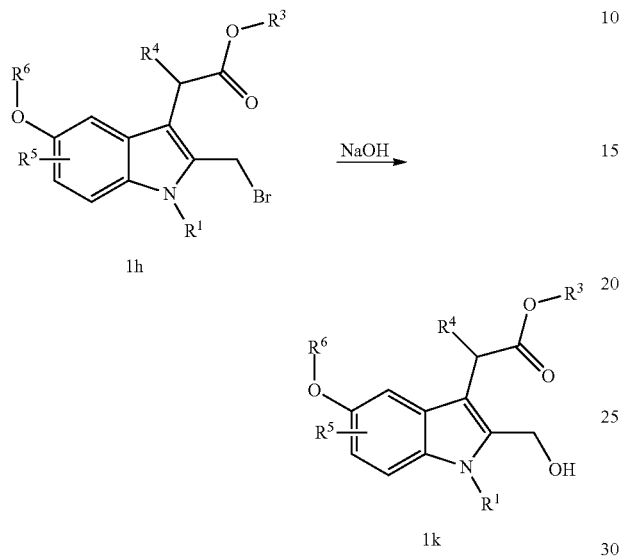

wherein: $R^1$, $R^3$, $R^4$, $R^5$ and $R^6$ have the above meanings

According to the invention 2-hydroxymethyl-derivatives of the general formula 1l and 2-sulfanylmethyl-derivatives of the general formula 1m are prepared by interaction of 2-bromomethyl-derivatives of the general formula 1h with optionally substituted phenolate or sulfanates of alkali metal of the general formula 8, respectively, according to the scheme given below:

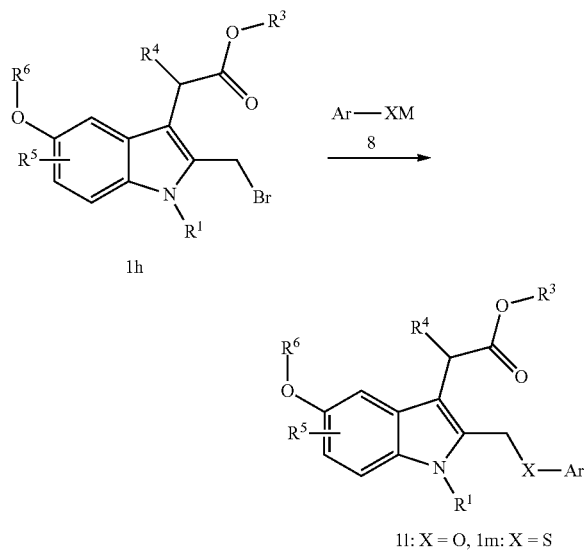

wherein: $R^1$, $R^3$, $R^4$, $R^5$ and $R^6$ have the above meanings; Ar represents optionally substituted aryl or heteroaryl; M represents alkali metal kation.

According to the invention 2-aminoethyl-derivatives of the general formula 1n are prepared by aminomethylation of the corresponding 2-methyl-substituted of the general formula 1($R^2$=H, $R^6 \neq$H) according to the scheme given below:

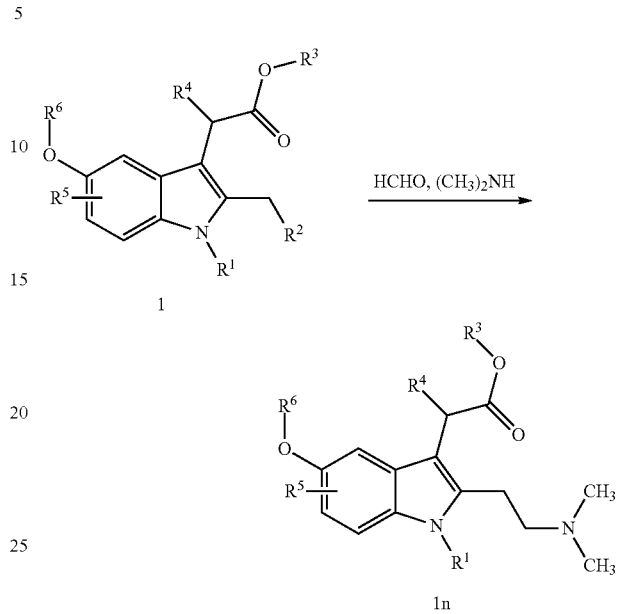

wherein in formula 1: $R^2$=H, $R^6 \neq$H, and $R^1$, $R^3$, $R^4$ and $R^5$ have the above meanings; in formula 1n: $R^1$, $R^3$, $R^4$, $R^5$ and $R^6$ have the above meanings;

According to the invention substituted 2-(1H-indol-3-yl) acetic acids of the general formula 1o are prepared by hydrolysis of the corresponding esters of the general formula 1 according to the scheme given below:

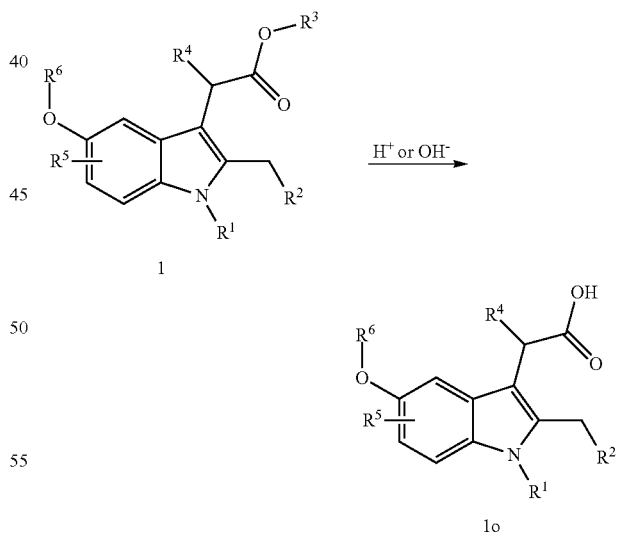

wherein in formula 1: $R^3$=alkyl, and $R^1$, $R^2$, $R^4$, $R^5$ and $R^6$ have the above meanings; in formula 1o: $R^1$, $R^2$, $R^4$, $R^5$ and $R^6$ have the above meanings According to the invention substituted 2-(1H-indol-3-yl) acetic acids of the general formula 1p are prepared by alkylation of the corresponding compounds of the general formula 1 by alkyl halides of the general formula 9 according to the scheme given below:

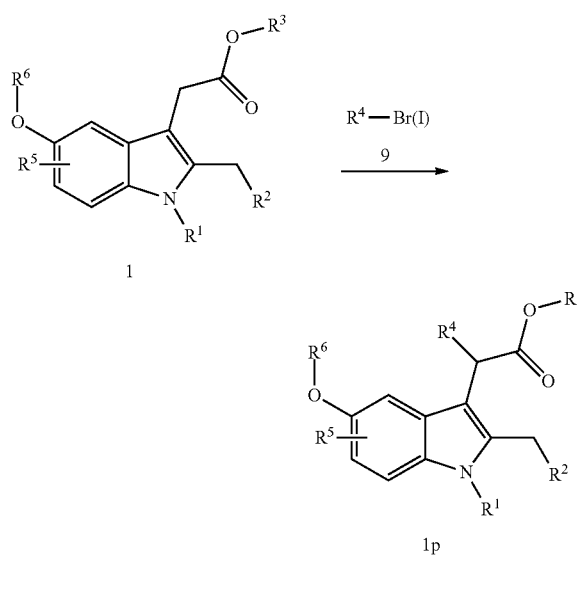

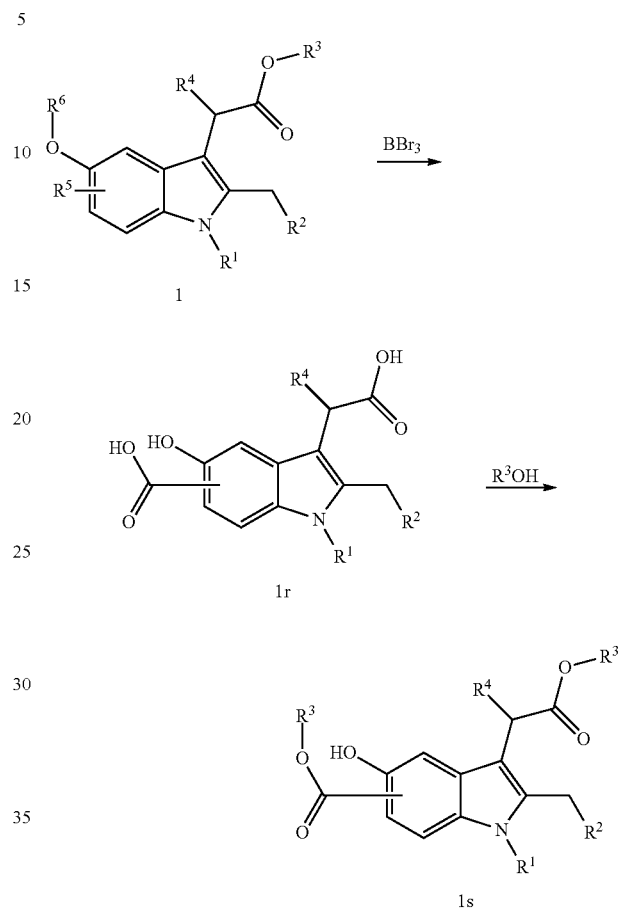

wherein in formula 1: $R^4$=H, and $R^1$, $R^2$, $R^3$, $R^5$ and $R^6$ have the above meanings; in formula 1p: $R^4$=alkyl, and $R^1$, $R^2$, $R^3$, $R^5$ and $R^6$ have the above meanings;

According to the invention substituted 4-aminomethyl-indoles of the general formula 1q are prepared by aminomethylation of the corresponding 5-hydroxy-indoles of the general formula 1 according to the scheme given below:

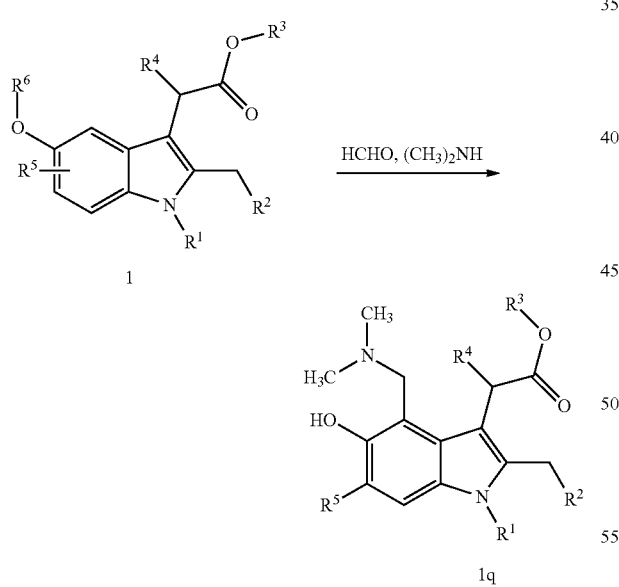

wherein in formula 1: $R^6$=H, and $R^1$, $R^2$, $R^3$, $R^4$ and $R^5$ are all as mentioned above; in formula 1q: $R^1$, $R^2$, $R^3$, $R^4$ and $R^5$ are all as mentioned above.

According to the invention dicarboxylic acids of the general formula 1r and esters thereof of the general formula 1s are prepared by the action of boron tribromide on the corresponding trifluoromethyl-derivatives of the general formula 1 and subsequent esterification of the resultant dicarboxylic acids 1r to esters 1s according to the scheme given below:

wherein in formula 1: $R^5$=CF$_3$, and $R^1$, $R^2$, $R^3$, $R^4$ and $R^6$ are all as mentioned above; in formula 1r: $R^1$, $R^2$ and $R^4$ are all as mentioned above; in formula 1s: $R^1$, $R^2$, $R^3$ and $R^4$ are all as mentioned above.

According to the invention substituted aryl- and hetaryl-derivatives of the general formula 1t are prepared by interaction of the corresponding bromides of the general formula 1 ($R^5$=Br) with optionally substituted aryl- or hetaryl-boronic acids 10 in the presence of palladium catalyst according to the scheme given below:

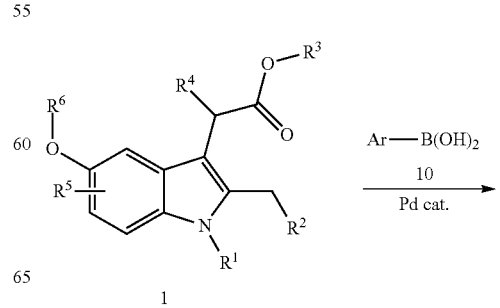

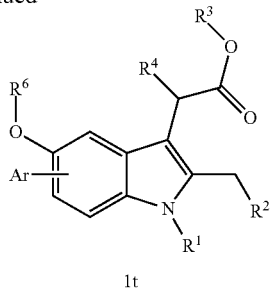

1t wherein in formula 1: $R^5$=Br, and $R^1$, $R^2$, $R^3$, $R^4$ and $R^6$ have the above meanings; in formula 1t: $R^1$, $R^2$, $R^3$, $R^4$ and $R^6$ have the above meanings; Ar represents optionally substituted aryl or heteroaryl.

According to the invention substituted 2-(1H-indol-3-yl)acetic acids of the general formula 1u and esters thereof of the general formula 1v are prepared by dealkylation of the corresponding compounds of the general formula 1 ($R^6$=alkyl) with boron tribromide with subsequent esterification of the resulting acids of the general formula 1u according to the scheme given below.

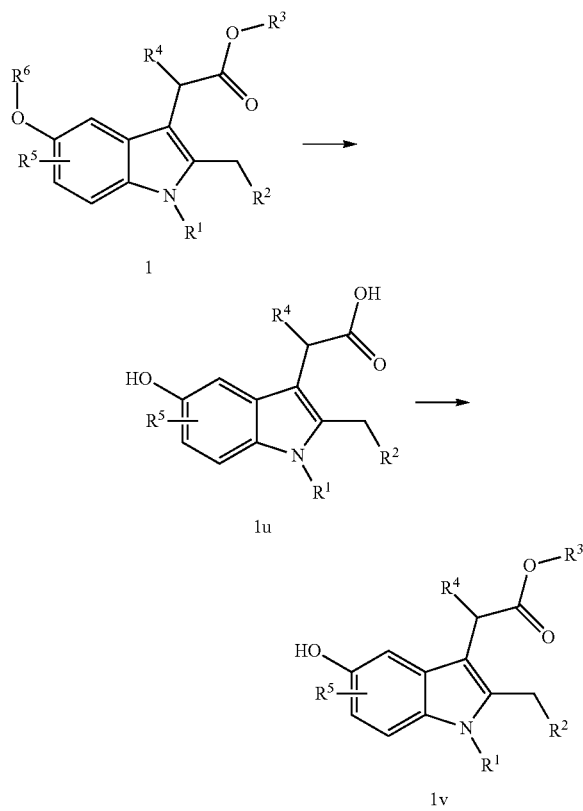

wherein in formula 1: $R^6$=alkyl, $R^1$, $R^2$, $R^3$, $R^4$ and $R^5$ are all as mentioned above;
in formula 1u: $R^1$, $R^2$, $R^4$ and $R^5$ are all as mentioned above;
in formula 1v: $R^1$, $R^2$, $R^3$, $R^4$ and $R^5$ have the above meanings.

According to the invention substituted 2-(5-acyloxy-1H-indol-3-yl)acetic acids of the general formula 1w and their esters of the general formula 1x are prepared by acylation of the corresponding 2-(5-hydroxy-1H-indol-3-yl)acetic acids of the general formula 1u in which $R^6$=H or their esters of the general formula 1v in which $R^6$=H, respectively, with carboxylic acid anhydride or acyl chlorides 4 according to the scheme given below,

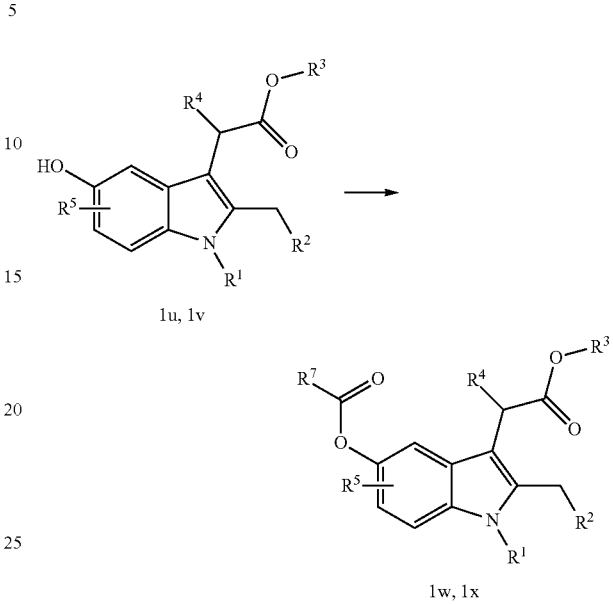

wherein in formulas 1u and 1w: $R^3$=H, $R^1$, $R^2$, $R^4$, $R^5$ and $R^7$ have the above meanings in formulas 1v and 1x: $R^1$, $R^2$, $R^3$, $R^4$, $R^5$ and $R^7$ have the above meanings.

Substituted 2-(5-hydroxy-2-methyl-1H-indol-3-yl)acetic acids of the general formula 1 may form hydrates or pharmaceutically acceptable salts. Both organic and mineral acids could be used for salt preparation, for example, hydrochloric acid, hydrobromic acid, hydroiodic acid, sulfuric acid, phosphoric acid, formic acid, acetic acid, propionic acid, trifluoroacetic acid, maleic acid, tartaric acid, methanesulphonic acid, benzenesulfonic acid, p-toluenesulfonic acid.

Both organic and mineral bases could be used for salt preparation. As mineral bases, for example, sodium hydroxide, carbonate, bicarbonate and hydride; kalium hydroxide, bicarbonate, and carbonate; lithium hydroxide; calcium hydroxide; magnesium hydroxide; zinc hydroxide are used. Amines and amino acids with basicity high enough to give the salt stable and suitable for use in medicine (in particular, they are to be of low toxicity) are used as organic bases, from which salts of the disclosed acids could be prepared. Ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like fall into the category of such amines.

Hydrates are usually formed during recrystallization of compounds of the general formula 1 or their salts from water or water containing solvents.

The purpose of the present invention is novel active ingredients.

The purpose in view is achieved by antiviral active ingredients representing substituted 2-(5-hydroxy-2-methyl-1H-indol-3-yl)acetic acids and esters thereof of the general formula 1 and pharmaceutically acceptable salts and/or hydrates thereof,

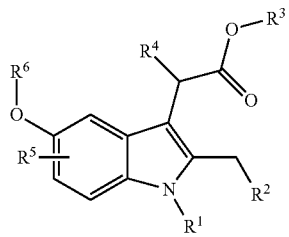

1 wherein: $R^1$ represents an amino group substituent selected from hydrogen, optionally substituted $C_1$-$C_5$ alkyl, acyl or sulfonyl;

$R^2$ and $R^4$ independently of each other represent an alkyl substituent selected from hydrogen, halogen, optionally substituted $C_1$-$C_3$alkyl, optionally substituted hydroxyl, optionally substituted amino group, optionally substituted aminomethyl, substituted mercapto group;

$R^3$ represents hydrogen, optionally substituted $C_1$-$C_5$ alkyl;

$R^5$ represents a cyclic system substituent selected from hydrogen, fluorine, trifluoromethyl, carboxy group, alkoxycarbonyl, conceivably substituted aryl, heterocyclyl, optionally substituted aminomethyl, cyano group;

$R^6$ represents a hydroxyl group substituent selected from hydrogen, optionally substituted $C_1$-$C_5$ alkyl, acyl.

The subject of the present invention is active ingredients, exhibiting antiviral activity towards influenza viruses representing substituted 2-(5-hydroxy-2-methyl-1H-indol-3-yl) acetic acids and their esters of the general formula 1 and pharmaceutically acceptable salts and/or hydrates thereof.

The preferable antiviral active ingredients are substituted 2-(5-hydroxy-2-methyl-4-fluoro-1H-indol-3-yl)acetic acids of the general formula 1.1, substituted 2-(5-hydroxy-2-methyl-6-fluoro-1H-indol-3-yl)acetic acids of the general formula 1.2, substituted 2-(5-hydroxy-2-methyl-4-trifluoromethyl-1H-indol-3-yl)acetic acids of the general formula 1.3, substituted 2-(5-hydroxy-2-methyl-6-trifluoromethyl-1H-indol-3-yl)acetic acids of the general formula 1.4, substituted 2-(5-hydroxy-2-methyl-4-cyano-1H-indol-3-yl)acetic acids of the general formula 1.5, substituted 2-(5-hydroxy-2-methyl-6-cyano-1H-indol-3-yl)acetic acids of the general formula 1.6, their esters and pharmaceutically acceptable salts and/or hydrates thereof, 1.1

-continued 1.2

1.3

1.4

1.5

1.6 wherein: $R^1$, $R^2$, $R^3$ and $R^6$ have the above meanings.

The preferable antiviral active ingredients are substituted 2-(1-benzoyl-2-methyl-5-methoxy-1H-indol-3-yl)acetic acids and esters thereof of the general formula A2, and pharmaceutically acceptable salts and/or hydrates thereof,

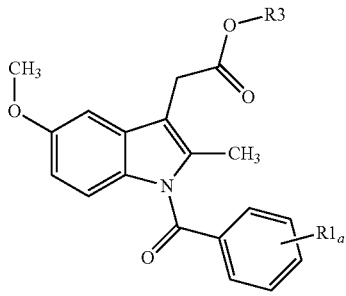

A2 wherein: R3 represents hydrogen, an optionally substituted $C_1$-$C_5$ alkyl, optionally substituted aryl; R1$_a$ represents 4-F, 4-Cl, 4-CF$_3$, 4-CF$_3$O, 4-N$_3$, 2,4,6-Cl$_3$.

The more preferable antiviral active ingredients are methyl 2-(2-methyl-5-methoxy-4-fluoro-1H-indol-3-yl)acetate 1.1(1), methyl 2-(2-methyl-5-methoxy-6-fluoro-1H-indol-3-yl)acetate 1.2(1), methyl 2-(2-methyl-5-methoxy-4-(trifluoromethyl)-1H-indol-3-yl)acetate 1.3(1), methyl 2-(2-methyl-5-methoxy-6-(trifluoromethyl)-1H-indol-3-yl)acetate 1.4(1), methyl 2-(2-methyl-5-methoxy-4-cyano-1H-indol-3-yl)acetate 1.5(1), methyl 2-(2-methyl-5-methoxy-6-cyano-1H-indol-3-y) acetate 1.6(1), methyl 2-[2-methyl-5-methoxy-4-fluoro-1-(4-chlorobenzoyl)-1H-indol-3-yl]acetate 1e(1), methyl 2-[2-methyl-5-methoxy-6-fluoro-1-(4-chlorobenzoyl)-1H-indol-3-yl]acetate 1e(2), methyl 2-[2-methyl-5-methoxy-4-(trifluoromethyl)-1-(4-chlorobenzoyl)-1H-indol-3-yl]acetate 1e(3), methyl 2-[2-methyl-5-methoxy-6-(trifluoromethyl)-1-(4-chlorobenzoyl)-1H-indol-3-yl]acetate 1e(4), 2-[2-methyl-5-methoxy-4-(trifluoromethyl)-1-(4-chlorobenzoyl)-1H-indol-3-yl]acetic acid 1e(5), 2-[2-methyl-5-methoxy-6-(trifluoromethyl)-1-(4-chlorobenzoyl)-1H-indol-3-yl]acetic acid 1e(6), methyl 2-[2-methyl-5-methoxy-1-(4-chlorobenzoyl)-4-cyano-1H-indol-3-yl]acetate 1e(7), methyl 2-[2-methyl-5-methoxy-1-(4-chlorobenzoyl)-6-cyano-1H-indol-3-yl]acetate 1e(8), methyl 2-[2-methyl-5-methoxy-6-fluoro-1-(p-tolylsulfonyl)-1H-indol-3-yl]acetate 1f(1), methyl 2-(2-methyl-5-methoxy-6-(trifluoromethyl)-1-phenylsulfonyl-1H-indol-3-yl)acetate 1f(2), methyl 2-[2-methyl-5-methoxy-6-(trifluoromethyl)-1-(pyridin-3-ylsulfonyl)-1H-indol-3-yl] acetate 1f(3), methyl 2-(2-methyl-5-methoxy-1-(methylsulfonyl)-6-(trifluoromethyl)-1H-indol-3-yl)acetate 1f(4), methyl 2-(1-(benzolsulfonyl)-2-methyl-5-methoxy-6-(trifluoromethyl)-1H-indol-3-yl)acetate 1f(5), methyl 2-(1,2-dimethyl-5-methoxy-4-fluoro-1H-indol-3-yl)acetate 1g(1), methyl 2-(1,2-dimethyl-5-methoxy-6-fluoro-1H-indol-3-yl)acetate 1g(2), methyl 2-(1,2-dimethyl-5-methoxy-4-(trifluoromethyl)-1H-indol-3-yl)acetate 1g(3), methyl 2-(1,2-dimethyl-5-methoxy-6-(trifluoromethyl)-1H-indol-3-yl)acetate 1g(4), ethyl 2-(1-ethyl-5-methoxy-2-methyl-6-(trifluoromethyl)-1H-indol-3-yl)butanoate 1g(5), methyl 2-(1,2-dimethyl-5-methoxy-4-cyano-1H-indol-3-yl)acetate 1g(6), methyl 2-(1,2-dimethyl-5-methoxy-6-cyano-1H-indol-3-yl) acetate 1g(7), methyl 2-[1-(2-hydroxyethyl)-2-methyl-5-methoxy-4-fluoro-1H-indol-3-yl]acetate 1g(8), methyl 2-[1-(2-hydroxyethyl)-2-methyl-5-methoxy-6-fluoro-1H-indol-3-yl]acetate 1g(9), methyl 2-[1-(2-hydroxyethyl)-2-methyl-5-methoxy-4-(trifluoromethyl)-1H-indol-3-yl]acetate 1g(10), methyl 2-[1-(2-hydroxyethyl)-2-methyl-5-methoxy-6-(trifluoromethyl)-1H-indol-3-yl]acetate 1g(11), methyl 2-[1-(2-(dimethylamino)ethyl)-2-methyl-5-methoxy-4-fluoro-1H-indol-3-yl]acetate 1g(12), methyl 2-[1-(2-(dimethylamino)ethyl)-2-methyl-5-methoxy-6-fluoro-1H-indol-3-yl]acetate 1g(13), methyl 2-[1-(2-(dimethylamino)ethyl)-2-methyl-5-methoxy-4-(trifluoromethyl)-1H-indol-3-yl] acetate 1g(14), methyl 2-[1-(2-(dimethylamino)ethyl)-2-methyl-5-methoxy-6-(trifluoromethyl)-1H-indol-3-yl] acetate 1g(15), methyl 2-[1-(2-(dimethylamino)ethyl)-2-methyl-5-methoxy-4-cyano-1H-indol-3-yl]acetate 1g(16), methyl 2-[1-(2-(dimethylamino)ethyl)-2-methyl-5-methoxy-6-cyano-1H-indol-3-yl]acetate 1g(17), 2-[1-(2-hydroxyethyl)-2-methyl-5-methoxy-6-(trifluoromethyl)-1H-indol-3-yl]acetic acid 1g(18), 2-[1-(2-(dimethylamino)ethyl)-2-methyl-5-methoxy-6-(trifluoromethyl)-1H-indol-3-yl]acetic acid 1g(19), 2-[2-(dimethylamino)methyl-5-methoxy-1-(4-chlorobenzoyl)-1H-indol-3-yl]acetic acid 1i(1), methyl 2-[2-(dimethylamino)methyl-5-methoxy-6-fluoro-1-(4-chlorobenzoyl)-1H-indol-3-yl]acetate 1i(2), 2-[2-(dimethylamino)methyl-5-methoxy-6-fluoro-1-(4-chlorobenzoyl)-1H-indol-3-yl]acetic acid 1i(3), methyl 2-[2-(dimethylamino)methyl-5-methoxy-6-(trifluoromethyl)-1-(4-chlorobenzoyl)-1H-indol-3-yl]acetate 1i(4), 2-[2-(dimethylamino)methyl-5-methoxy-6-(trifluoromethyl)-1-(4-chlorobenzoyl)-1H-indol-3-yl]acetic acid 1i(5), methyl 2-[2-(dimethylamino)methyl-5-methoxy-4-(trifluoromethyl)-1-(4-chlorobenzoyl)-1H-indol-3-yl]acetate 1i(6), 2-[2-(dimethylamino)methyl-5-methoxy-4-(trifluoromethyl)-1-(4-chlorobenzoyl)-1H-indol-3-yl]acetic acid 1i(7), methyl 2-(2-(dimethylamino)methyl-5-methoxy-4-fluoro-1H-indol-3-yl)acetate 1i(8), 2-(2-(dimethylamino)methyl-5-methoxy-4-fluoro-1H-indol-3-yl)acetic acid 1i(9), methyl 2-(2-(dimethylamino)methyl-5-methoxy-4-(trifluoromethyl)-1H-indol-3-yl)acetate 1i(10), 2-(2-(dimethylamino)methyl-5-methoxy-4-(trifluoromethyl)-1H-indol-3-yl)acetic acid 1i(11), methyl 2-(2-(dimethylamino)methyl-1-methyl-5-methoxy-4-fluoro-indol-3-yl)acetate 1i(12), 2-(2-(dimethylamino)methyl-1-methyl-5-methoxy-4-fluoro-1H-indol-3-yl)acetic acid 1i(13), methyl 2-(2-(dimethylamino)methyl-1-methyl-5-methoxy-4-(trifluoromethyl)-1H-indol-3-yl)acetate 1i(14), 2-(2-(dimethylamino)methyl-1-methyl-5-methoxy-4-(trifluoromethyl)-1H-indol-3-yl)acetic acid 1i(15), methyl 2-(2-(dimethylamino)methyl-5-methoxy-6-fluoro-1H-indol-3-yl)acetate 1i(16), methyl 2-(2-(dimethylamino)methyl-5-methoxy-6-(trifluoromethyl)-1H-indol-3-yl)acetate 1i(17), 2-(2-(dimethylamino)methyl-5-methoxy-6-(trifluoromethyl)-1H-indol-3-yl)acetic acid 1i(18), 2-(2-(dimethylamino)methyl-5-methoxy-6-fluoro-1H-indol-3-yl) acetic acid 1i(19), methyl 2-(2-(dimethylamino)methyl-1-methyl-5-methoxy-6-fluoro-1H-indol-3-yl)acetate 1i(20), methyl 2-(2-(dimethylamino)methyl-1-methyl-5-methoxy-6-(trifluoromethyl)-1H-indol-3-yl)acetate 1i(21), 2-(2-(dimethylamino)methyl-1-methyl-5-methoxy-6-fluoro-1H-indol-3-yl)acetic acid 1i(22), 2-(2-(dimethylamino)methyl-1-methyl-5-methoxy-6-(trifluoromethyl)-1H-indol-3-yl)acetic acid 1i(23), 2-(5-acetyloxy-2-(dimethylamino)methyl-1-methyl-6-phenyl-1H-indol-3-yl)acetic acid 1i(24), 2-(5-acetyloxy)-2-(dimethylamino)methyl-1-methyl-6-(pyridin-3-yl)-1H-indol-3-yl)acetic acid 1i(25), 2-[2-(hydroxymethyl)-5-methoxy-1-(4-chlorobenzoyl)-1H-indol-3-yl]acetic acid 1k(1), 2-[5-methoxy-2-(phenyloxymethyl)-1-(4-chlorobenzoyl)-1H-indol-3-yl]acetic acid 1l(1), methyl 2-[1-methyl-5-methoxy-2-((4-chlorophenyloxy)methyl)-1H-indol-3-yl]acetate 1l(2), methyl 2-(1-methyl-5-methoxy-6-fluoro-2-(phenylsulfanylmethyl)-1H-indol-3-yl)acetate 1m(1), methyl 2-[1-methyl-5-methoxy-6-fluoro-2-(pyridin-3-ylsulfanylmethyl)-1H-indol-3-yl]acetate 1m(2), methyl 2-[2-(2-dimethylamino)ethyl-1-methyl-5-methoxy-6-fluoro-1H-indol-3-yl]acetate 1n(1), methyl 2-[2-(2-dimethylamino)ethyl-1-methyl-5-methoxy-6-(trifluoromethyl)-1H-indol-3-yl]

acetate 1n(2), 2-(2-methyl-5-methoxy-4-fluoro-1H-indol-3-yl)acetic acid 1o (1), 2-(2-methyl-5-methoxy-6-fluoro-1H-indol-3-yl)acetic acid 1o(2), 2-(2-methyl-5-methoxy-4-(trifluoromethyl)-1H-indol-3-yl)acetic acid 1o(3), 2-(2-methyl-5-methoxy-6-(trifluoromethyl)-1H-indol-3-yl)acetic acid 1o(4), 2-(1,2-dimethyl-5-methoxy-6-(trifluoromethyl)-1H-indol-3-yl)acetic acid 1o(5), 2-(1,2-dimethyl-5-methoxy-6-fluoro-1H-indol-3-yl)acetic acid 1o(6), 2-(1,2-dimethyl-5-methoxy-4-(trifluoromethyl)-1H-indol-3-yl)acetic acid 1o(7), methyl [2-(1,2-dimethyl-5-methoxy-6-(trifluoromethyl)-1H-indol-3-yl]propionate 1p(1), methyl 2-(1,2-dimethyl-5-methoxy-6-(trifluoromethyl)-1H-indol-3-yl)-4-dimethylaminobutyrate 1p(2), methyl 2-(1,2-dimethyl-5-methoxy-6-(trifluoromethyl)-1H-indol-3-yl)-3-phenylpropionate 1p(3), methyl 2-(1,2-dimethyl-5-methoxy-6-fluoro-1H-indol-3-yl)-3-(pyridin-3-yl)propionate 1p(4), methyl 2-(5-hydroxy-4-(dimethylamino)methyl-2-methyl-6-fluoro-1H-indol-3-yl)acetate 1q(1), methyl 2-(5-hydroxy-1,2-dimethyl-4-(dimethylamino)methyl-6-fluoro-1H-indol-3-yl)acetate 1q(2), 2-[2,4-bis(dimethylaminomethyl)-1-methyl-5-hydroxy-6-(pyridin-3-yl)-1H-indol-3-yl]acetic acid 1q(3), 2-(1,2-dimethyl-5-hydroxy-6-carboxy-1H-indol-3-yl)acetic acid 1r(1), methyl 2-(1,2-dimethyl-5-hydroxy-6-(methyloxycarbonyl)-1H-indol-3-yl)acetate 1s(1), 2-(1,2-dimethyl-5-methoxy-4-(pyridin-4-yl)-1H-indol-3-yl)acetic acid 1t(1), 2-(1,2-dimethyl-5-methoxy-4-phenyl-1H-indol-3-yl)acetic acid 1t(2), methyl 2-[1,2-dimethyl-5-methoxy-6-(4-fluorophenyl)-1H-indol-3-yl]acetate 1t(3), methyl 2-(1,2-dimethyl-5-methoxy-6-(pyridin-3-yl)-1H-indol-3-yl)acetate 1t(4), 2-(5-hydroxy-2-(dimethylamino)methyl-1-methyl-6-(pyridin-3-yl)-1H-indol-3-yl)acetic acid 1t(5), 2-[1,2-dimethyl-5-hydroxy-6-(4-fluorophenyl)-1H-indol-3-yl]acetic acid 1u(1), 2-(1,2-dimethyl-5-hydroxy-6-(pyridin-3-yl)-1H-indol-3-yl)acetic acid 1u(2), 2-(5-hydroxy-2-methyl-4-fluoro-1H-indol-3-yl)acetic acid 1u(3), 2-(5-hydroxy-2-methyl-6-fluoro-1H-indol-3-yl)acetic acid 1u(4), 2-(5-hydroxy-1,2-dimethyl-4-fluoro-1H-indol-3-yl)acetic acid 1u(5), 2-(5-hydroxy-1,2-dimethyl-6-fluoro-1H-indol-3-yl)acetic acid 1u(6), 2-[5-hydroxy-1-(2-hydroxyethyl)-2-methyl-4-fluoro-1H-indol-3-yl]acetic acid 1u(7), 2-[5-hydroxy-1-(2-hydroxyethyl)-2-methyl-6-fluoro-1H-indol-3-yl]acetic acid 1u(8), 2-[5-hydroxy-1-(2-dimethylamino ethyl)-2-methyl-4-fluoro-1H-indol-3-yl]acetic acid 1u(9), 2-[5-hydroxy-1-(2-dimethylamino ethyl)-2-methyl-6-fluoro-1H-indol-3-yl]acetic acid 1u (10), methyl 2-(5-hydroxy-1,2-dimethyl-6-fluoro-1H-indol-3-yl)acetate 1v(1), methyl 2-(5-hydroxy-2-methyl-4-fluoro-1H-indol-3-yl)acetate 1v(2), methyl 2-(5-hydroxy-2-methyl-6-fluoro-1H-indol-3-yl)acetate 1v(3), methyl 2-(5-hydroxy-1,2-dimethyl-4-fluoro-1H-indol-3-yl)acetate 1v(4), methyl 2-[5-hydroxy-1-(2-hydroxyethyl)-2-methyl-4-fluoro-1H-indol-3-yl]acetate 1v(5), methyl 2-[5-hydroxy-1-(2-hydroxyethyl)-2-methyl-6-fluoro-1H-indol-3-yl]acetate 1v(6), methyl 2-[5-hydroxy-1-(2-dimethylamino)ethyl-2-methyl-4-fluoro-1H-indol-3-yl]acetate 1v(7), methyl 2-[5-hydroxy-1-(2-dimethylamino)ethyl-2-methyl-6-fluoro-1H-indol-3-yl]acetate 1v(8), 2-(5-acetyloxy-1,2-dimethyl-6-fluoro-1H-indol-3-yl)acetic acid 1w(1), methyl 2-(5-acetyloxy-1,2-dimethyl-4-fluoro-1H-indol-3-yl)acetate 1x(1), methyl 2-(5-acetyloxy-2-methyl-4-(trifluoromethyl)-1H-indol-3-yl)acetate 1x(2) and pharmaceutically acceptable salts and/or hydrates thereof.

The subject of the present invention is also a pharmaceutical composition exhibiting antiviral activity comprising as an active ingredient at least one substituted 2-(5-hydroxy-2-methyl-1H-indol-3-yl)acetic acid or its ester of the general formula 1 or pharmaceutically acceptable salt and/or hydrate thereof.

The preferable pharmaceutical composition is the pharmaceutical composition exhibiting antiviral activity towards influenza viruses comprising as an active ingredient at least one substituted 2-(5-hydroxy-2-methyl-1H-indol-3-yl)acetic acid or its ester of the general formula 1 or pharmaceutically acceptable salt and/or hydrate thereof.

The more preferable pharmaceutical composition is the pharmaceutical composition exhibiting antiviral activity in relation to hepatisis C viruses comprising as an active ingredient at least one substituted 2-(5-hydroxy-2-methyl-1H-indol-3-yl)acetic acid or its ester of the general formula 1 or pharmaceutically acceptable salt and/or hydrate thereof.

Pharmaceutical compositions may include pharmaceutically acceptable excipients. Pharmaceutically acceptable excipients mean diluents, auxiliary agents and/or carriers applied in the sphere of pharmaceutics. According to the invention pharmaceutical composition in addition to the drug substance of general formula 1 may include other active ingredients provided that they do not give rise to undesirable effects, for example, allergic reactions.

If needed, according to the present invention pharmaceutical compositions can be used in clinical practice in various forms prepared by mixing the said compositions with traditional pharmaceutical carries; for example, peroral forms (such as, tablets, gelatinous capsules, pills, solutions or suspensions); forms for injections (such as, solutions or suspensions for injections, or a dry powder for injections which requires only addition of water for injections before utilization); local forms (such as, ointments or solutions).

According to the present invention the carriers used in pharmaceutical compositions represent carriers which are used in the sphere of pharmaceutics for preparation of commonly applied forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The purpose of the present invention is a method for the preparation of pharmaceutical compositions.

The purpose in view is achieved by mixing an active ingredient with inert exicipient and/or solvent, a distinctive feature of which consists in using at least one substituted 2-(5-hydroxy-2-methyl-1H-indol-3-yl)acetic acid or its ester of the general formula 1 or pharmaceutically acceptable salt and/or hydrate thereof as an active ingredient.

The subject of the present invention is also a medicament in the form of tablets, capsules, or injections, placed in pharmaceutically acceptable packing comprising a novel active ingredient or a novel pharmaceutical composition intended for treatment of viral diseases.

The more preferable medicament comprising the novel active ingredient or the novel pharmaceutical composition is a medicament intended for treatment diseases caused by influenza viruses.

The preferable medicament is a medicament comprising the novel active ingredient or the novel pharmaceutical composition intended for hepatisis C treatment.

The subject of the present invention is also a therapeutic cocktail for prophylaxis and treatment of viral diseases among them diseases caused by influenza and hepatisis C viruses including as one of the component the novel medicament or the novel pharmaceutical composition comprising as an active ingredient at least one substituted 2-(5-hydroxy-2-methyl-1H-indol-3-yl)acetic acid or its ester of the general formula 1 or pharmaceutically acceptable salt and/or hydrate thereof.

The therapeutic cocktails for prophylaxis and treatment of hepatisis C along with the drug substances disclosed in the invention, may include other active ingredients such as: inhibitors inosine-5-monophosphate dehydrogenase, for example, Ribavirin (allowed) and Ribamidine; inhibitors of NS3 hepatisis C protease, for example, Telaprevir, Siluprevir and SCH-503034; inhibitors of RNK-polimerazy NS5B, for example, XTL-2125; alpha-glucosidase inhibitors, for example, aminocarbohydrate Selgozivir; and also TLR-receptor agonists, hepatoprotectors, cyclosporines, various proteins (for example, interferons), antibodies, vaccines etc.

The subject of the present invention is also a method for prophylaxis and treatment of viral diseases at humans and animals.

According to the present invention the method for prophylaxis and treatment of viral diseases at humans and animals among them caused by influenza and hepatisis C viruses (HCV), consists in introduction of novel medicament, novel pharmaceutical composition or novel therapeutic cocktail comprising as an active ingredient substituted 2-(5-hydroxy-2-methyl-1H-indol-3-yl)acetic acids or their esters of the general formula 1 or pharmaceutically acceptable salts and/or hydrates thereof to warm-blooded animals or humans.

Medicaments could be introduced peroral or parenterally (for example, intravenously, subcutaneously, intraperitoneally or locally). Clinical doses of a medicament comprising an active ingredient of the general formula 1, may be corrected depending on: therapeutic efficiency and bio-accessibility of the active ingredients in patients' organism, rate of their exchange and removal from organism, and age, gender, and severity of patient's symptoms. Thus, the daily intake for adults normally being 10~500 mg, preferably 50~300 mg. Accordingly, the above effective doses are to be taken into consideration while preparing medicament from the pharmaceutical composition of the present invention, each dose unit of the medicament contains 10~500 mg of the active ingredient of the general formula 1, preferably 50~300 mg. Following the instructions of physician or pharmacist, the medicaments may be taken several times over specified periods of time (preferably, from one to six times).

BEST EMBODIMENT OF THE INVENTION

Below the invention is described by means of specific examples, which illustrate but not limit the scope of the invention.

The examples given below describe synthesis of substituted 2-(5-hydroxy-2-methyl-1H-indol-3-yl)acetic acids and their esters of the general formula 1, pharmaceutically acceptable salts and biological tests of them. Test results for compounds of the general formula 1, their pharmaceutically acceptable salts and biological activity thereof are presented in Tables 1-3.

EXAMPLE 1

General Method for the Preparation of Substituted 2-(1H-indol-3-yl)acetic Acids of the General Formulas 1a, 1b, 1c, 1d, 1.1(1), 1.2(1), 1.3(1), 1.4(1), 1.5(1), 1.6(1)

The mixture consisting of substituted 4-methoxyphenylhydrazine hydrochloride of the general formulas 2 or 2.1 (21 mmol), levulinic acid ester 3 or 3.1 (21 mmol) and acetic acid (10 ml) was heated at 80° C. for 4 hours. The cooled reaction mixture was concentrated in vacuo, the residue was stirred in a mixture of ethyl acetate and ammonia aqua. The organic layer was separated and after evaporation of the solvent the residue was subjected to chromatographic separation using ethylacetate-hexane as eluent. Substituted 2-(1H-indol-3-yl) acetic acids of the general formulas 1a, 1b, 1c, 1d, 1.1(1), 1.2(1), 1.3(1), 1.4(1), 1.5(1), 1.6(1) were prepared, some of them are presented in Table 1.

TABLE 1

Substituted 2-(5-hydroxy-2-methyl-1H-indol-3-yl)acetic acids, their esters of the general formula 1 and pharmaceutically acceptable salts thereof.

| No | MW | LCMS (M + 1) | NMR |
|---|---|---|---|
| 1.1(1) | 251.26 | 252 | $^1$H NMR (DMSO-D$_6$, 400 MHz) δ 10.93 (s, 1H), 6.97 (d, J = 8.8 Hz, 1H), 6.85 (t, J = 8.4 Hz, 1H), 3.78 (s, 3H), 3.72 (s, 2H), 3.59 (s, 3H), 2.27 (s, 3H). $^1$H NMR (CDCl$_3$) δ 2.18 (s, 3H), 3.67 (s, 3H), 3.75 (s, 2H), 3.85 (s, 3H), 6.70-6.80 (m, 2H), 8.02 (br. s., 1H); $^{13}$C NMR (CDCl$_3$) δ 11.5, 30.8 (J$_{C-F}$ = 1.9 Hz), 52.2, 59.0, 102.6, 105.8 (J$_{C-F}$ = 4.2 Hz), 111.1, 118.4 (J$_{C-F}$ = 16.7 Hz), (J$_{C-F}$ = 2.3 Hz), 132.9 (J$_{C-F}$ = 10.6 Hz), 134.5, 140.2 (J$_{C-F}$ = 9.4 Hz), 146.2 (J$_{C-F}$ = 242.8 Hz), 173.3. LCMS, m/z, M + 1 = 252, rt 10.59 min., purity (254 nm) 99.0%. |
| 1.2(1) | 251.26 | 252 | $^1$H NMR (DMSO-D$_6$, 400 MHz) δ 10.78 (s, 1H), 7.07 (d, J = 12.0 Hz, 1H), 7.06 (d, J = 8.0 Hz, 1H), 3.80 (s, 3H), 3.65 (s, 2H), 3.59 (s, 3H), 2.28 (s, 3H). $^1$H NMR, δ, ppm, CDCl$_3$: 2.29 (s, 3H), 3.61 (s, 2H), 3.65 (s, 3H), 3.89 (s, 3H), 6.91 (d, J$_{H-F}$ = 11.6 Hz, 1H), 6.99 (d, J$_{H-F}$ = 8.4 Hz, 1H), 7.83 (br. s, 1H); $^{13}$C NMR (CDCl$_3$) δ 11.9, 30.4, 52.2, 57.2, 98.3 (d, J$_{C-F}$ = 23.1 Hz), 102.1 (d, J$_{C-F}$ = 2.3 Hz), 104.4, 124.1, 128.5 (d, J$_{C-F}$ = 11.0 Hz), 133.2, 143.1 (d, J$_{C-F}$ = 12.0 Hz), 150.3 (d. J$_{C-F}$ = 237.4 Hz), 172.7. LCMS, m/z, M + 1 = 252, rt 10.68 min., purity (254 nm) 99.4%. |
| 1.3(1) | 301.27 | 302 | $^1$H NMR (DMSO-D$_6$, 400 MHz) δ 11.25 (s, 1H), 7.48 (d, J = 8.8 Hz, 1H), 6.91 (d, J = 8.8 Hz, 1H), 3.84 (s, 3H), 3.66 (m, 2H), 3.60 (s, 3H), 2.34 (s, 3H). |
| 1.4(1) | 301.217 | 302 | $^1$H NMR (DMSO-D$_6$, 400 MHz) δ 11.13 (s, 1H), 7.45 (s, 1H), 7.14 (1H), 3.83 (s, 3H), 3.71 (s, 2H), 3.59 (s, 3H), 2.33 (s, 3H). $^{13}$C NMR (DMSO-D$_6$, 75 MHz) δ 171.87, 150.76 (d, J = 1.5 Hz), 137.74, 131.48, 128.28, 124.94 (q, J = 269.3 Hz), 110.45 (q, J = 30.0 Hz), 109.05 (q, J = 6.0 Hz), |

TABLE 1-continued

Substituted 2-(5-hydroxy-2-methyl-1H-indol-3-yl)acetic acids, their esters of the general formula 1 and pharmaceutically acceptable salts thereof.

| No | MW | LCMS (M + 1) | NMR |
|---|---|---|---|
| | | | 103.99, 100.51, 56.23, 51.57, 29.28, 11.54. $^1$H NMR (CDCl$_3$) δ 2.37 (s, 3H), 3.61 (s, 2H), 3.62 (s, 3H), 3.90 (s, 3H), 7.01 (s, 1H), 7.39 (s, 1H), 8.00 (br. s, 1H); LCMS, m/z, M + 1 = 302, rt 11.42 min., purity (254 nm) 99.6%. |
| 1.5(1) | 258.28 | 259 | |
| 1.6(1) | 258.28 | 259 | |
| 1e(1) | 389.81 | 390 | |
| 1e(2) | 389.81 | 390 | |
| 1e(3) | 439.82 | 440 | $^1$H NMR (DMSO-D$_6$, 400 MHz) δ 7.69 (m, 4H), 7.39 (s, 1H), 7.37 (s, 1H), 3.91 (s, 3H), 3.87 (s, 2H), 3.64 (s, 3H), 2.19 (s, 3H). |
| 1e(4) | 439.82 | 440 | $^1$H NMR (DMSO-D$_6$, 400 MHz) δ 7.70 (d, J = 8.4 Hz, 2H), 7.49 (d, J = 8.4 Hz, 2H), 7.38 (d, J = 9.2 Hz, 1H), 6.84 (d, J = 9.2 Hz, 1H), 3.87 (s, 3H), 3.79 (d, J = 2.4 Hz, 2H), 3.72 (s, 3H), 2.60 (s, 3H). |
| 1e(5) | 425.80 | 426 | |
| 1e(6) | 425.80 | 426 | |
| 1e(7) | 396.83 | 397 | $^1$H NMR (CDCl$_3$, 400 MHz) δ 7.67 (d, J = 8.8 Hz, 2H), 7.51 (d, J = 8.8 Hz, 2H), 7.82 (d, J = 9.2 Hz, 1H), 6.73 (d, J = 9.2 Hz, 1H), 4.00 (s, 2H), 3.94 (s, 3H), 3.78 (s, 3H), 2.33 (s, 3H). |
| 1e(8) | 396.83 | 397 | $^1$H NMR (CDCl$_3$, 400 MHz) δ 7.67 (d, J = 8.4 Hz, 2H), 7.52 (d, J = 8.4 Hz, 2H), 7.31 (s, 1H), 7.00 (s, 1H), 3.98 (s, 3H), 3.73 (s, 3H), 3.69 (s, 2H), 2.38 (s, 3H). |
| 1f(1) | 405.45 | 406 | $^1$H NMR (CDCl$_3$) δ 2.31 (s, 3H), 2.49 (s, 3H), 3.52 (s, 2H), 3.60 (s, 3H), 3.87 (s, 3H), 6.89 (d, J$_{H-F}$ = 8.1 Hz, 1H), 7.17 (m, 2H), 7.58 (m, 2H), 7.93 (d, J$_{H-F}$ = 12.1 Hz); LCMS, m/z, M + 1 = 406, rt 14.66 min., purity (254 nm) 98.0%. |
| 1f(2) | 441.43 | 442 | |
| 1f(3) | 442.42 | 443 | |
| 1f(4) | 379.36 | 380 | |
| 1f(5) | 455.46 | 456 | |
| 1g(1) | 265.29 | 266 | $^1$H NMR (DMSO-D$_6$, 400 MHz) δ 7.10 (d, J = 8.4 Hz, 1H), 6.92 (t, J = 8.0 Hz, 1H), 3.78 (s, 3H), 3.74 (s, 2H), 3.60 (s, 3H), 3.57 (s, 3H), 2.28 (s, 3H). |
| 1g(2) | 265.29 | 266 | $^1$H NMR (DMSO-D$_6$, 400 MHz) δ 7.31 (d, J = 12.0 Hz, 1H), 7.10 (d, J = 8.4 Hz, 1H), 3.81 (s, 3H), 3.70 (s, 2H), 3.59 (s, 3H), 3.58 (s, 3H), 2.29 (s, 3H). $^1$H NMR (CDCl$_3$) δ 2.32 (s, 3H), 3.55 (s, 3H), 3.63 (s, 5H), 3.89 (s, 3H), 6.90 (d, J$_{H-F}$ = 11.4 Hz, 1H), 7.00 (d, J$_{H-F}$ = 8.3 Hz, 1H); LCMS, m/z, M + 1 = 266, rt 11.45 min., purity (254 nm) 99.0%. |
| 1g(3) | 315.29 | 316 | $^1$H NMR (DMSO-D$_6$, 400 MHz) δ 7.69 (dd, J$_1$ = 9.2 Hz, J$_2$ = 0.4 Hz, 1H), 7.04 (d, J = 9.2 Hz, 1H), 3.84 (s, 3H), 3.72 (q, J = 2.8 Hz, 2H), 3.70 (s, 3H), 3.57 (s, 3H), 2.34 (s, 3H). |
| 1g(4) | 315.29 | 316 | $^1$H NMR (DMSO-D$_6$, 400 MHz) δ 7.66 (s, 1H), 7.18 (s, 1H), 3.85 (s, 3H), 3.76 (s, 2H), 3.69 (s, 3H), 3.59 (s, 3H), 2.35 (s, 3H). $^1$H NMR (CDCl$_3$) δ 2.38 (s, 3H), 3.60-3.63 (m, 8H), 3.90 (s, 3H), 7.01 (s, 1H), 7.41 (s, 1H); LCMS, m/z, M + 1 = 302, rt 12.37 min., purity (254 nm) 98.0%. |
| 1g(5) | 371.40 | 372 | |
| 1g(6) | 272.31 | 273 | $^1$H NMR (CDCl$_3$, 400 MHz) δ 7.37 (d, J = 9.2 Hz, 2H), 6.80 (d, J = 9.2 Hz, 1H), 3.98 (s, 2H), 3.95 (s, 3H), 3.79 (s, 3H), 3.67 (s, 3H). |
| 1g(7) | 272.31 | 273 | $^1$H NMR (CDCl$_3$, 400 MHz) δ 7.45 (s, 1H), 6.99 (s, 1H), 3.96 (s, 3H), 3.69 (s, 3H), 3.68 (s, 2H), 3.67 (s, 3H), 2.42 (s, 3H). |
| 1g(8) | 295.31 | 296 | |
| 1g(9) | 295.31 | 296 | |
| 1g(10) | 345.32 | 346 | |
| 1g(11) | 322.38 | 323 | $^1$H NMR (DMSO-D$_6$, 400 MHz) δ 11.12 (br, 1H), 7.39 (dd, J$_1$ = 14.4 Hz, J$_2$ = 8.4 Hz, 1H), 6.99 (t, J = 8.8 Hz, 1H), 4.53 (s, 2H), 3.81 (s, 2H), 3.77 (s, 2H), 3.59 (s, 3H), 3.26 (t, J = 6.8 Hz, 2H), 2.83 (s, 6H), 2.36 (s, 3H). |
| 1g(11)·HCl | 358.84 | 323 | |
| 1g(12)·HCl | 358.84 | 323 | |
| 1g(13)·HCl | 408.85 | 373 | |
| 1g(14) | 345.32 | 346 | |
| 1g(15)·HCl | 408.85 | 373 | |
| 1g(16) | 329.40 | 330 | $^1$H NMR (CD$_3$OD, 400 MHz) δ 7.72 (d, J = 9.2 Hz, 1H), 7.01 (d, J = 9.2 Hz, 1H), 4.60 (t, J = 8.0 Hz, 2H), 3.97 (s, 2H), 3.95 (s, 3H), 3.72 (s, 3H), 3.46 (t, J = 8.0 Hz, 2H), 3.01 (s, 6H), 2.45 (s, 3H). |
| 1g(17) | 329.40 | 330 | |
| 1g(18) | 331.29 | 332 | |
| 1g(19) | 358.36 | 359 | |

TABLE 1-continued

Substituted 2-(5-hydroxy-2-methyl-1H-indol-3-yl)acetic acids, their esters of the general formula 1 and pharmaceutically acceptable salts thereof.

| No | MW | LCMS (M + 1) | NMR |
|---|---|---|---|
| 1i(1) | 400.87 | 401 | |
| 1i(2) | 418.86 | 419 | |
| 1i(3) | 482.89 | 483 | |
| 1i(4) | 432.88 | 433 | |
| 1i(5) | 468.86 | 469 | |
| 1i(6)•HCl | 519.35 | 483 | |
| 1i(7) | 468.86 | 469 | |
| 1i(8)•HCl | 330.79 | 295 | |
| 1i(9) | 280.30 | 281 | |
| 1i(10)•HCl | 380.80 | 345 | |
| 1i(11) | 330.31 | 331 | |
| 1i(12)•HCl | 344.82 | 309 | |
| 1i(13) | 294.33 | 295 | |
| 1i(14)•HCl | 394.82 | 359 | |
| 1i(15) | 344.34 | 345 | |
| 1i(16) | 294.33 | 295 | $^1$H NMR (DMSO-D$_6$, 400 MHz) δ 10.47 (tr., 1H), 7.48 (d, J = 12.0 Hz, 1H), 7.18 (d, J = 8.4 Hz, 1H), 4.56 (d, J = 4.8 Hz, 2H), 3.98 (s, 2H), 3.83 (s, 3H), 3.82 (s, 3H), 3.63 (s, 3H), 2.75 (s, 6H). |
| 1i(17)•HCl | 380.80 | 345 | $^1$H NMR (DMSO-D$_6$, 400 MHz) δ 11.50 (s, 1H), 10.47 (br., 1H), 7.72 (s, 1H), 7.28 (s, 1H), 4.49 (s, 2H), 3.98 (s, 2H), 3.86 (s, 3H), 3.64 (s, 3H), 2.75 (s, 6H). |
| 1i(18) | 330.31 | 331 | |
| 1i(19) | 280.30 | 281 | |
| 1i(20)•HCl | 344.82 | 309 | |
| 1i(21)•HCl | 394.82 | 359 | |
| 1i(22) | 294.33 | 295 | |
| 1i(23) | 344.34 | 345 | |
| 1i(24) | 380.45 | 381 | |
| 1i(25) | 381.44 | 382 | |
| 1k(1) | 373.80 | 374 | |
| 1l(1) | 449.89 | 450 | |
| 1l(2) | 373.84 | 374 | |
| 1m(1) | 373.45 | 374 | |
| 1m(2) | 374.44 | 375 | |
| 1n(1)•HCl | 358.82 | 323 | $^1$H NMR (DMSO-D$_6$) δ 2.78 (s, 6H), 3.0-3.2 (m, 4H), 3.56 (s, 3H), 3.64 (s, 3H), 3.75 (s, 2H), 3.76 (s, 3H), 7.07 (d, J$_{H-F}$ = 8.4 Hz, 1H), 7.33 (d, J$_{H-F}$ = 12.1 Hz, 1H), 10.72 (br. s, 1H); LCMS, m/z, M + 1 = 323, rt 7.51 min., purity (254 nm) 96.6%. |
| 1n(2)•HCl | 408.85 | 373 | $^1$H NMR (DMSO-D$_6$) δ 2.78 (s, 6H), 3.08-3.28 (m, 4H), 3.57 (s, 3H), 3.75 (s, 3H), 3.80 (s, 3H), 3.82 (s, 2H), 7.15 (s, 1H), 7.68 (s, 1H), 11.07 (br. s, 1H); LCMS, m/z, M + 1 = 373, rt 8.45 min., purity (254 nm) 99.1%. |
| 1o(1) | 237.23 | 238 | $^1$H NMR (DMSO-D$_6$, 400 MHz) δ 12.06 (br., 1H), 10.88 (s, 1H), 6.97 (d, J = 8.4 Hz, 1H), 6.84 (t, J = 8.4 Hz, 1H), 3.78 (s, 3H), 3.61 (s, 2H), 2.26 (s, 3H). |
| 1o(2) | 237.23 | 238 | $^1$H NMR (DMSO-D$_6$, 400 MHz) δ 12.08 (br., 1H), 10.74 (s, 1H), 7.08 (d, J = 2.0 Hz, 1H), 7.05 (s, 1H), 3.80 (s, 3H), 3.54 (s, 2H), 2.28 (s, 3H). |
| 1o(3) | 287.24 | 288 | |
| 1o(4) | 287.24 | 288 | $^1$H NMR DMSO-D$_6$, 400 MHz) δ 12.14 (s, 1H), 11.09 (s, 1H), 7.45 (s, 1H), 7.14 (s, 1H), 3.83 (s, 3H), 3.60 (s, 2H), 2.33 (s, 3H). |
| 1o(5) | 301.27 | 302 | $^1$H NMR (DMSO-D$_6$, 400 MHz) δ 12.1 (s, 1H), 7.65 (s, 1H), 7.18 (s, 1H), 3.84 (s, 3H), 3.69 (s, 3H), 3.64 (s, 2H), 2.34 (s, 3H). |
| 1o(6) | 251.26 | 252 | $^1$H NMR (DMSO-D$_6$, 400 MHz) δ 12.1 (s, 1H), 7.31 (d, J = 12 Hz, 1H), 7.1 (d, J = 8 Hz, 1H), 3.81 (s, 3H), 3.59 (s, 3H), 3.58 (s, 2H), 2.29 (s, 3H). |
| 1o(7) | 301.27 | 302 | $^1$H NMR (DMSO-D$_6$, 400 MHz) δ 12.00 (br., 1H), 7.67 (d, J = 8.8 Hz, 1H), 7.03 (d, J = 8.8 Hz, 1H), 3.84 (s, 3H), 3.69 (s, 3H), 3.63 (q, J = 2.0 Hz, 2H), 2.33 (s, 3H). |
| 1p(1) | 329.32 | 330 | $^1$H NMR (CDCl$_3$, 400 MHz) δ 7.47 (s, 1H), 7.18 (s, 1H), 3.96 (q, J = 7.2 Hz, 1H), 3.94 (s, 3H), 3.67 (2s, 6H), 2.42 (s, 3H), 1.57 (d, J = 7.2 Hz, 3H). |
| 1p(2)•HCl | 422.88 | 387 | |
| 1p(3) | 405.42 | 406 | |
| 1p(4)•HCl | 392.86 | 357 | |
| 1q(1)•HCl | 330.79 | 295 | |
| 1q(2)•HCl | 344.82 | 309 | $^1$H NMR (DMSO-D$_6$) δ 2.28 (s, 3H), 2.71 (s, 6H), 3.51 (s, 3H), 3.57 (s, 3H), 3.79 (s, 2H), 4.52 (s, 2H), 7.46 (d, J$_{H-F}$ = 11.4 Hz, 1H), 9.48 (br. s, 1H), 9.60 (br. s, 1H); LCMS, m/z, M + 1 = 309, rt 7.14 min., purity (254 NM) 99.2%. |

TABLE 1-continued

Substituted 2-(5-hydroxy-2-methyl-1H-indol-3-yl)acetic acids, their esters of the general formula 1 and pharmaceutically acceptable salts thereof.

| No | MW | LCMS (M + 1) | NMR |
|---|---|---|---|
| 1q(3)•3HCl | 505.87 | 397 | |
| 1r(1) | 263.25 | 264 | |
| 1s(1) | 291.31 | 292 | $^1$H NMR (CDCl$_3$) δ 2.38 (s, 3H), 3.50-3.70 (m, 8H), 3.90 (s, 3H), 6.95 (s, 1H), 7.72 (s, 1H), 10.40 (s, 1H); $^{13}$C NMR (CDCl$_3$) δ 11.0, 30.0, 30.4, 30.5, 52.2, 103.5, 103.8, 106.7, 110.1, 131.1, 134.1, 141.1, 155.0, 171.5, 172.5; LCMS, m/z, M + 1 = 292, rt 11.47 min., purity (254 nm) 95.3%. |
| 1t(1) | 310.36 | 311 | |
| 1t(2) | 309.37 | 310 | |
| 1t(3) | 313.33 | 314 | |
| 1t(4) | 296.33 | 297 | |
| 1t(5) | 339.40 | 340 | |
| 1u(1) | 313.33 | 314 | |
| 1u(2) | 296.33 | 297 | |
| 1u(3) | 223.21 | 224 | |
| 1u(4) | 223.21 | 224 | |
| 1u(5) | 237.23 | 238 | |
| 1u(6) | 237.23 | 238 | |
| 1u(7) | 267.26 | 268 | |
| 1u(8) | 267.26 | 268 | |
| 1u(9) | 294.33 | 295 | |
| 1u(10) | 294.33 | 295 | |
| 1v(1) | 251.26 | 252 | $^1$H NMR (CDCl$_3$) δ 2.30 (s, 3H), 3.50 (s, 3H), 3.59 (s, 2H), 3.62 (s, 3H), 4.88 (br. s, 1H), 6.90 (d, J$_{H-F}$ = 11.4 Hz, 1H), 7.10 (d, J$_{H-F}$ = 8.3 Hz, 1H); LCMS, m/z, M + 1 = 252, rt 9.90 min., purity (254 nm) 99.8%. |
| 1v(2) | 237.23 | 238 | |
| 1v(3) | 237.33 | 238 | |
| 1v(4) | 251.26 | 252 | |
| 1v(5) | 281.29 | 282 | |
| 1v(6) | 281.29 | 282 | |
| 1v(7) | 308.36 | 309 | |
| 1v(8) | 308.36 | 309 | |
| 1w(1) | 279.27 | 280 | |
| 1x(1) | 293.30 | 294 | |
| 1x(2) | 329.28 | 330 | |

EXAMPLE 2

General Method for the Preparation of Substituted 2-(1-acyl-1H-indol-3-yl)acetic Acids of the General Formula 1e The mixture consisting of substituted 2-(1H-indol-3-yl) acetic acid of the general formula 1 (1 mmol) where R$^1$=H, acyl chloride (1 mmol) of the general formula 4 and triethylamine (1 mmol, 30 mg) in benzene (2 ml) or other suitable solvent was vigorously stirred at room temperature for 30 min and distributed between water and ethylacetate. The organic layer was concentrated, the residue was purified on silica gel using dichloromethane:hexane eluent. Substituted 2-(1-acyl-1H-indol-3-yl)acetic acids of the general formula 1e were prepared, some of them are presented in Table 1.

EXAMPLE 3

General Method for the Preparation of Substituted 2-(1-sulfonyl-1H-indol-3-yl)acetic Acids of the General Formula 1f 50% KOH water solution (1 ml) was added dropwise to the solution consisting of substituted 2-(1H-indol-3-yl)acetic acid of the general formula 1 where R$^1$=H (1 mmol), sulfonyl chloride (1 mmol) of the general formula 5 and tetrabutylammonium hydrogen sulphate (35 mg) in benzene (3 ml). The mixture was stirred vigorously at room temperature for 30 min and distributed between water and ethyl acetate. The residue after evaporation of organic layer was purified on silica gel using as eluent dichloromethane:hexane mixture (2:1). Substituted 2-(1-sulfonyl-1H-indol-3-yl)acetic acids of the general formula 1f were prepared, some of them are presented in Table 1.

EXAMPLE 4

General Method for the Preparation of Substituted alkyl 2-(1-alkyl-1H-indol-3-yl)acetates of the General Formula 1g Sodium hydride (0.169 g, 7.05 mmol) was added in small portions to the solution of substituted 2-(1H-indol-3-yl)acetic acid of the general formula 1 where R$^1$=H, R$^3$≠H, R$^6$≠H (3.357 mmol) in dry DMF (15 ml) at vigorous stirring and cooling in ice bath. After the addition was completed the reaction mixture was stirred for 30 min, then alkyl halide (7 mmol) of the general formula 6 was added dropwise to the mixture and stirring was continued for 12 h. The reaction mixture was filtered, poured into water and extracted with benzene. Organic extract was dried over Na$_2$SO$_4$, the solvent was evaporated in vacuo, the residue was recrystallized or resolved by column chromatography using ethylacetate:hexane as eluent. Substituted alkyl 2-(1-alkyl-1H-indol-3-yl)acetates of the general formula 1g were prepared, some of them are presented in Table 1.

EXAMPLE 5

General Method for the Preparation of Substituted 2-(2-aminomethyl-indol-3-yl)acetic Acids of the General Formula 1i A. Substituted 2-(2-methyl-1H-indol-3-yl)acetic acid 1($R^2$=H) (0.0115 mol) and N-bromosuccinimide (2 g, 0.0115 mol) were dissolved in acetic acid (25 ml) and stirred at room temperature for 4 h (LCMS control). Then the reaction mixture was poured into water, the product was filtered off and dried in vacuo. 2-Bromomethyl-derivatives of the general formula 1h were prepared and used in further reactions without additional purification.

B. Indomethacin A2 (R3=H, $R1_a$=4-Cl) (1 g, 2.8 mmol) and N-bromosuccinimide (0.539 g, 3.08 mmol) were suspended in tetrachloromethane (50 ml) and kept at room temperature for 12 h. The reaction mixture was heated to boiling and filtered off from succinimide. The solid was washed with hot tetrachloromethane (150 ml). The solvent was evaporated in vacuo. Prepared 2-(1-(4-chlorobenzoyl)-5-methoxy-2-methyl-1H-indol-3-yl)-acetohypobromoanhydride was boiled in $CCl_4$ (50 ml) for 1.5 h. 2-((2-(Bromomethyl)-1-(4-chlorobenzoyl)-5-methoxy-1H-indol-3-yl)acetic acid 1 h ($R^1$=4-chlorobenzoyl, $R^3$=$R^4$=$R^5$=H, $R^6$=$CH_3$) was prepared and used in further reactions without additional purification.

B. Amine of the general formula 7 (3-5 mmol) was added to the solution of 2-bromomethylindole (0.75 g, 1.716 mmol) 1 h in THF (25 ml), the resultant mixture was stirred at room temperature for 5 minutes and evaporated. The product was recrystallized from the proper solvent or subjected to chromatographic purification on silica gel. The corresponding substituted 2-(2-aminomethyl-1H-indol-3-yl)acetic acids of the general formula 1i were prepared, some of them are presented in Table 1.

EXAMPLE 6

General Method for the Preparation of Substituted 2-(2-hydroxymethyl-indol-3-yl)acetic Acids of the General Formula 1k ($R^3$=H)

The mixture of 5% NaOH water solution (10 ml) and substituted 2-(2-bromomethyl-1H-indol-3-yl)acetic acid (0.639 mmol) of the general formula 1h was stirred at room temperature for 1 h (LCMS control). After the process was completed the reaction mixture was acidified, precipitated solid was filtered off and, if it was necessary, subjected to chromatographic purification on silica gel. Substituted 2-(2-hydroxymethyl-indol-3-yl)acetic acids of the general formula 1k ($R^3$=H) were prepared, some of them are presented in Table 1.

EXAMPLE 7

General Method for the Preparation of Substituted 2-(2-hydroxy(or mercapto)methyl-indol-3-yl)acetic Acids of the General Formulas 1l or 1m Respectively ($R^3$=H)

The mixture consisting of 5% NaOH water solution (10 ml), aromatic or heterocyclic phenol or thiophenol (0.7 mmol) of the general formula 8 and substituted 2-(2-bromomethyl-1H-indol-3-yl)acetic acid (0.7 mmol) of the general formula 1h was stirred at room temperature for one hour (LCMS control). After the process was completed the reaction mixture was acidified, precipitated solid was filtered off and, if it was necessary, subjected to chromatographic purification on silica gel. Substituted 2-(2-hydroxy(or mercapto)methyl-indol-3-yl)acetic acids of the general formulas 1l, 1m ($R^3$=H) were prepared, some of them are presented in Table 1.

EXAMPLE 8

General Method for the Preparation of Substituted 2-(2-(2-aminoethyl)-indol-3-yl)acetic Acids of the General Formula 1n The mixture consisting of substituted 2-(2-methyl-indol-3-yl)acetic acid (0.6 mmol) of the general formula 1 where $R^2$=H, 40% water solution of dimethylamine (0.5 ml), 37% solution of formalin (0.5 ml) and acetic acid (1 ml) was heated at 60° C. for 18 h. After the process was completed (LCMS control) acetic acid was distilled off in vacuo, the residue was distributed between ethyl acetate and $K_2CO_3$ water solution. The residue after evaporation of organic phase was purified on silica gel using 1% solution of triethylamine in chloroform with methanol gradient 0-10% as eluent. For the complete removal of triethylamine traces the prepared compound was subjected to lyophilization with dioxane. After that the residue was dissolved in dioxane again, converted into hydrochloride by adding 1N HCl dioxane solution, freezed again and subjected to lyophilization. Substituted 2-((2-aminoethyl)-1H-indol-3-yl)acetic acids of the general formula 1n were prepared, some of them are presented in Table 1.

EXAMPLE 9

General Method for the Preparation of Substituted 2-(indol-3-yl)acetic Acids of the General Formula 1o KOH (0.5 g) was added to the solution of substituted alkyl 2-(indol-3-yl)acetate (3.077 mmol) of the general formula 1, where $R^3$=alkyl, in MeOH:THF:$H_2O$ (3:1:1) mixture (50 ml). The reaction mixture was kept at room temperature for 20 h or at reflux for 1.5 h. The course of the reaction was controlled by thin layer chromatography using ethyl acetate:hexane (1:3) eluent. After the process was completed the reaction mixture was acidified with HCl, diluted twice with water, and organic solvents were evaporated. The obtained solid was filtered off, washed with water and dried in vacuo. Substituted 2-(indol-3-yl)acetic acids of the general formula 1o were prepared, some of them are presented in Table 1.

EXAMPLE 10

General Method for the Preparation of Substituted 2-(indol-3-yl)acetic Acids of the General Formula 1p A. Sodium hydride (3.3 mmol) was added in small portions to the solution of substituted alkyl 2-(1H-indol-3-yl)acetate (3 mmol) 1, where $R^1$≠H, in absolute DMF (15 ml) at vigorous stirring and cooling in ice bath. After the addition was completed the reaction mixture was stirred for 30 min, then alkyl halide (3.3 mmol) was added and stirring was continued for additional 12 hs. After that the reaction mixture was filtered, poured into water and extracted with benzene. The organic extract was dried over $Na_2SO_4$, the solvent was evaporated in vacuo, the residue was recrystallized or subjected to chromatographic purification using as eluent ethyl acetate:hexane. Substituted 2-(indol-3-yl)acetic acids of the general formula 1p were prepared, some of them are presented in Table 1.

B. The synthesis was carried out in the same manner as described in example 10A. Substituted alkyl 2-(1H-indol-3-yl)acetate 1, where $R^1$=H (one equivalent), and sodium hydride:alkyl halide (3 equivalents) were used. The corresponding substituted 2-(indol-3-yl)acetic acids of the general formula 1p where $R^1$=$R^4$=alkyl were prepared, some of them are presented in Table 1.

EXAMPLE 11

General Method for the Preparation of Substituted 2-(4-aminomethyl-1H-indol-3-yl)acetic Acids of the General Formula 1q Substituted 2-(5-hydroxy-1H-indol-3-yl)acetic acid (0.5 mmol) of the general formula 1 where $R^6$=H and bisdimethylaminomethane (153 mg, 1.5 mmol) or the corresponding amount of formalin and amine were dissolved in a mixture consisting of dioxane (10 ml), AcOH (40 ml) and water (20 ml). The reaction was carried out at room temperature (LCMS control). After the process was completed the reaction mixture was evaporated in vacuo, the product was recrystallized from acetonitrile or subjected to chromatographic purification on silica gel. Substituted 2-(4-aminomethyl-1H-indol-3-yl)acetic acids of the general formula 1q were prepared, some of them are presented in Table 1.

EXAMPLE 12

General Method for the Preparation of Substituted Dicarboxylic Acids of the General Formula 1r and their Esters of the General Formula 1s 10M $BBr_3$ solution in dichloromethane (4 ml) was added to the solution of substituted 2-(6-trifluoromethyl-indol-3-yl)acetic acid (0.3 mmol) of the general formula 1, where $R^5$=6-$CF_3$, in dichloromethane (2 ml) cooled previously with dry ice. The mixture was heated under reflux for 18 h and concentrated in vacuo. Ethanol was added to the residue comprising the corresponding substituted dicarboxylic acid of the general formula 1r, the mixture was evaporated, the residue was dissolved in ethanol again, mixed together with 2 g of silica gel and the obtained mixture was dried in vacuo. The residue was transferred onto a starting zone of chromatographic column and eluted with hexane:ethyl acetate mixture with gradient from 25 to 50%. Substituted diesters of dicarboxylic acids of the general formula 1s were prepared, some of them are presented in Table 1.

EXAMPLE 13

General Method for the Preparation of Substituted 2-(aryl- and hetaryl-indol-3-yl)acetic Acids of the General Formula 1t Substituted 2-(4- or 6-bromo-indol-3-yl)acetic acid (1.7 mmol) where $R^5$=Br, boronic acid (2.72 mmol) of the general formula 10, $Na_2CO_3$ (721 mg, 6.8 mmol), and $PdCl_2(PPh_3)_2$ (119 mg, 0.17 mmol) were added to a previously degasified ethanol:water (3:1) and the resultant mixture was refluxed for 1.5 h under argon. Then, $NaBH_4$ (1 mg, 0.0255 mmol) was added and the reaction mixture was refluxed for additional 1 h. The process was monitoring by LCMS. After the reaction was completed the hot reaction mixture was filtered through celit and evaporated in vacuo. The product was recrystallized from the proper solvent or subjected to chromatographic purification on silica gel. Substituted 2-(aryl- or hetaryl-indol-3-yl)acetic acids of the general formula 1t were prepared, some of them are presented in Table 1.

EXAMPLE 14

General Method for the Preparation of Substituted 2-(5-hydroxy-indol-3-yl)acetic Acids of the General Formula 1u and their Esters of the General Formula 1v A. The cooled solution of $BBr_3$ (4.02 g, 16.025 mmol) in $CH_2Cl_2$ (20 ml) was slowly added to the previously cooled to −78° C. solution of substituted 2-(5-alkyloxy-1H-indol-3-yl)acetic acid (3.205 mmol) of the general formula 1 where $R^6$=alkyl in $CH_2Cl_2$ (100 ml) under argon. The reaction mixture was stirred at −78° C. for 2 h, then stirring was continued at room temperature for 12 h (LCMS control). After the reaction was completed the resultant solution was poured into water and $K_2CO_3$ water solution was added to pH~8. Without separating organic and water layers $CH_2Cl_2$ was evaporated, and the remaining water solution was acidified to pH~3, and NaCl was added to saturation. The product was extracted with ethyl acetate and subjected to chromatographic purification on silica gel, eluent —$CHCl_3$:$CH_3OH$:AcOH (10:1:0.05). The corresponding substituted 2-(5-hydroxy-1H-indol-3-yl)acetic acids of the general formula 1u were prepared, some of them are presented in Table 1.

B. Solution of 10M $BBr_3$ (4 ml) in $CH_2Cl_2$ (20 ml) was added to the solution of the corresponding substituted 2-(5-alkyloxy-1H-indol-3-yl)acetic acid (0.3 mmol) of the general formula 1 where $R^6$=alkyl in dichloromethane (2 ml) cooled with dry ice. The mixture was refluxed for 18 h and evaporated in vacuo. Ethanol was added to the residue comprising the corresponding substituted acid of the general formula 1u, the mixture was concentrated, the residue was dissolved in ethanol again, mixed together with 2 g of silica gel and the mixture obtained was dried in vacuo. The residue was transferred onto a starting zone of chromatographic column and eluted with hexane:ethyl acetate mixture with gradient from 25 to 50%. Alkyl 2-(5-hydroxy-1H-indol-3-yl)acetates of the general formula 1v, were prepared, some of them are presented in Table 1.

EXAMPLE 15

General Method for the Preparation of Substituted 2-(5-acyloxy-1H-indol-3-yl)acetic Acids of the General Formula 1w and their Esters of the General Formula 1x The solution of the corresponding substituted 2-(5-hydroxy-indol-3-yl)acetic acid (5 mmol) of the general formula 1 where $R^6$=H in pyridine (3 ml) was gradually added to the solution of carboxylic acid anhydride (1020 mg, 10 mmol) or acyl chloride in pyridine (3 ml) at room temperature. After the addition was completed the reaction mixture was stirred for 30 min at room temperature and poured into saturated NaCl solution. The product was extracted with ethyl acetate or other proper solvent, the solvent was evaporated in vacuo. The residue was crystallized from the proper solvent. The corresponding substituted 2-(5-acyloxy-1H-indol-3-yl)acetic acids of the general formula 1w and their esters of the general formula 1x were prepared, some of them are presented in Table 1.

EXAMPLE 16

Determination of anti-influenza activity of the compounds of the general formula 1 towards viruses of influenza A/New Caledonia/20/99 (H1N1). Anti-influenza activity was determined by enzyme-linked immunosorbent assay method (ELISA) in MDCK cell culture. The MDCK cells were embedded in 96-well plate of "Costar" firm with average density of 35000 cells to each well and were grown in Eagle's minimum essential medium in the presence of 5% fetal calf serum and 10 µM of glutamine to full monolayer. Before infection with virus the cells were washed twice with medium without serum. Investigated compounds of the general formula 1 were added to the cells in concentration twice exceeding the concentration of the compounds in 100 ml of the medium used. By 100 ml of the same medium was added to the virus control, and by 200 ml—to the cell control. For experiments with the use of strains of influenza A/New Calcdonia/20/99(H1N1) viruses the investigated compounds and virus dilutions were prepared using the medium with the addition of 2.5 µg/ml of TPCK trypsin. After incubation of the cells together with the investigated compounds for 2 hours at 37° C. by 100 µl of allantoic virus diluted with the used medium was added to the wells with the exception of cell control; at that multiplicity of infection ranged approximately from 0.1 to 1 PFU per cell depending on experimental conditions. Then the plates were incubated for 17-20 hours. After incubation for the mentioned time in atmosphere of 5% $CO_2$ at 37° C. the cells were looked at under the inverted-stage microscope to be convinced of the absence of cytotoxic and cytopathic changes in them. Having convinced of their absence, the medium was removed, and the cells were fixing with 80% acetone on phosphate buffered saline (PBS) for 20 min, dried well and then washed three times with PBS and 0.05% Tween-20 (ELISA solution). These and all further procedures of washing were carried out with this solution. Then by 100 µl of PBS with 1% fetal calf serum and 0.05% Tween-20 were added to the cells and incubated for 30 minutes at 37° C. After removal of the solvent by 100 µl of monoclonal antibodies (MCA) to internal proteins of influenza A virus diluted with ELISA solution in ratio 1:1000 were added to the cells. After incubation with antibodies for 1 hour at 37° C. and subsequent 3-fold washing, by 100 µl of rabbit IgG against mouse IgG conjugated with horseradish peroxidase at dilution 1:5000-1:3000 were introduced into the wells, and incubation lasted for additional 1 hour at 37° C. After 4-fold washing the binded peroxidase was determined by addition to the wells of 100 µl of 0.05% o-phenylenediamine (oPD) solution in citrate buffer pH=5.0 comprising 0.003% $H_2O_2$. The plates were kept for 15-30 minutes in darkness until emergence of colouring, the reaction was ceased by addition of 50 µl of 4N $H_2SO_4$. Then optical density (OD) was measured with the help of automatic spectrophotometer at 492 nm using oPD. The wells, the cells of which were not infected with the virus, were used as a control. Typically the meanings of OD did not exceed 0.1-0.2. Inhibition percent of virus reproduction by the investigated compounds was calculated according to the formula: inhibition percent=100−(OD of the experiment−OD of cellular control/ OD of viral control in the absence of a compound−OD of cellular control)×100. For one experimental point 3 or 4 wells of the plate were used.

The primary screening of the compounds of the general formula 1 was performed on the basis of two experiments. Two multiplicities of infection (10-2 and 10-3, that is 0.1-1 PFU per cell) were used. For one point of every experiment three replications were used (that is three wells of the plate). Determination of concentration dependenses of inhibition percent for one multiplicity of infection made it possible to estimate $IC_{50}$. Four replications were used for one point of this experiment. Deviations from the average value did not amount to 10-15%. Relying on the results obtained, the dose-answer diagram was plotted on the basis of which $IC_{50}$ values were calculated. $IC_{50}$ values for some of the compounds of the general formula 1 are represented in Table 2.

TABLE 2

Antiviral activity of the compounds of the general formula 1 to influenza A/New Caledonia/20/99 (H1N1) viruses.

| Compound No | $IC_{50}$, mkg/ml |
| --- | --- |
| 1.4(1) | >15 |
| 1g(2) | 10 |
| 1i(13) | 12 |
| 1p(2)•HCl | 12 |
| 1t(5) | >15 |
| 1u(6) | >15 |

EXAMPLE 17

Determination of antiviral activity of the compounds of the general formula 1 towards hepatisis C viruses. Determination of antiviral activity of the compounds of the general formula 1 towards hepatisis C viruses (HCV) strain JFH-1 in cell culture of human hepatoma (Huh7) infected with HCV.

Cells Huh7 were embedded in 96-well plates ($7.5 \times 10^3$ cells in every well in 50 µl of nutrient solution). 5×-concentrated solutions of the tested compounds in DMEM medium {DMEM} 1×; the source: Cellgro; Catalogue: 10-013-CV} were prepared just before the usage. In total, four serial five-fold dilutions with concentration ranging from 250 µM to 2 µM were prepared. In 4 hours after cell embedding serial dilutions of the compounds were added to the cells (50 mkl per one well). Each dilution of the examined compound was tested for two identical wells. The final DMSO concentration amounted up to 0.5%. Then, the cells were incubated for 3 hours at 37° C./5% $CO_2$. After the incubation virus (300 tissue culture infective doses in 30 µl per one well) was added to the cells. The final DMSO concentration amounted up to 0.5%. Then the cells were incubated for 3 hours at 37° C./5% $CO_2$. The cells were fixed by addition acetone/methanol (1:1) mixture in amount of 250 gµl/well. In one minute the cells were washed with Phosphate Buffered Saline (PBS) three times. After that the cells were quenched by addition of 10% solution of fetal calf serum in PBS (150 µl/well) and kept for one hour at room temperature. Then the cells were incubated with mouse monoclonal antibody (100 µl/well) to cor-antigen HCV, clone C7-50 (Source: Affinity BioReagents; Catalogue: MA1-080) (working dilution—1:500 in 10% solution of fetal calf serum in PBS) for two hours at 37° C. The cells were washed 6 times with PBS/0.05% Tween 20 solution and incubated for one hour with peroxidase conjugated goat anti-mouse immunoglobulin (100 µl/well) (working dilution—1: 2500 in 10% solution of fetal calf serum in PBS). The cells were washed 6 times with PBS/0.05% Tween 20 solution, then with PBS solution, and 100 µl/well of the substrate (consisting of 1 tablet of oPD, 12 ml of citrate/phosphate buffer and 5 µl of 30% $H_2O_2$) were added. The plates were kept for 30 min in darkness at room temperature. The reaction was stopped by addition of 2N $H_2SO_2$ (100 µl/well), optical density (at 490 nm) was measured with the help of multichannel spectrophotometer Victor3 V 1420 (Perkin Elmer). $IC_{50}$ values for every tested compound were calculated using XLfit 4 programm. Table 3 shows $IC_{50}$ values for some of the compounds of the general formula 1.

TABLE 3

Antiviral activity of the compounds of the general formula 1 to hepatisis C virus.

| Compound No | IC$_{50}$, μM |
|---|---|
| 1e(1) | 39 |
| 1.1(1) | 38 |
| 1.2(1) | 13 |
| 1g(4) | 2.4 |
| 1.4(1) | 1.7 |
| 1g(2) | 6.3 |
| 1v(1) | 50 |

EXAMPLE 18

The Preparation of a Medicament in the Form of Tablets

Starch (1600 mg), ground lactose (1600 mg), talk (400 mg) and methyl 2-[2-(dimethylamino)methyl-5-methoxy-4-(trifluoromethyl)-1-(4-chlorobenzoyl)-1H-(indol-3-yl]acetate hydrochloride 1i(6).HCl (1000 mg) were mixed together and pressed into a bar. The resultant bar was comminuted into granules and sifted through sieve to collect granules of 14-16 mesh. The granules thus obtained were shaped into tablets of suitable form weighing 560 mg each.

EXAMPLE 19

The Preparation of a Medicament in the Form of Capsules

Methyl 2-[2-(dimethylamino)methyl-5-methoxy-4-(trifluoromethyl)-1-(4-chlorobenzoyl)-1H-(indol-3-yl]acetate hydrochloride 1i(6).HCl and lactose powder were carefully mixed in ratio 2:1. The resultant powdery mixture was packed into gelatin capsules of suitable size by 300 mg to capsule.

EXAMPLE 20

The Preparation of a Medicament in the Form of Compositions for Intramuscular, Intraperitoneal or Hypodermic Injections Methyl 2-[2-(dimethylamino)methyl-5-methoxy-4-(trifluoromethyl)-1-(4-chlorobenzoyl)-1H-(indol-3-yl]acetate hydro chloride 1i(6).HCl (500 mg), chlorobutanol (300 mg), propylene glycol (2 ml), and injectable water (100 ml) were mixed together. The resultant solution was filtered and placed into 1 ml ampoules, which were sealed and sterilized in autoclave.

INDUSTRIAL APPLICABILITY

The invention could be used in medicine, veterinary, biochemistry.

The invention claimed is:

1. A compound of general formula 1, or a pharmaceutically acceptable salt or hydrate thereof,

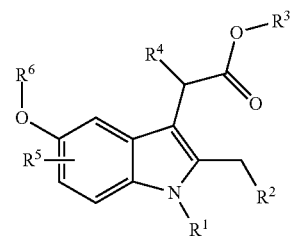

wherein:

$R^1$ is hydrogen, an optionally substituted $C_1$-$C_5$ alkyl, an optionally substituted $C_1$-$C_5$ alkylsulfonyl, an optionally substituted $C_1$-$C_5$ arylsulfonyl, an optionally substituted heterocyclylsulfonyl, or an acyl;

$R^2$ is hydrogen, a substituted amino group, an optionally substituted hydroxy group, a substituted mercapto group, a substituted alkylamino group;

$R^3$ is hydrogen, a $C_1$-$C_3$ alkyl;

$R^4$ is hydrogen, halogen, a $C_1$-$C_3$ alkyl, which is optionally substituted by amino group, an optionally substituted phenyl or a heterocyclyl;

$R^5$ is one or more cyclic system substituents selected from carboxyl, alkyloxycarbonyl, possibly substituted aryl, non-annelated heterocyclyl, substituted aminomethyl, cyano group; or $R^5$ is hydrogen under the condition when $R^1$ is substituent selected from hydroxy substituted $C_1$-$C_3$ alkyl, an amino substituted $C_1$-$C_3$ alkyl and $R^2$, $R^3$, $R^4$ are said, or when $R^2$ is a substituted amino group, an optionally substituted hydroxy group, a substituted mercapto group, a substituted alkylamino group and $R^1$, $R^3$, $R^4$ are said; or $R^5$ is fluoro or trifluoromethyl under the condition when $R^1$ is substituent selected from a lower alkyl, a substituted sulfonyl, a hydroxy substituted $C_1$-$C_3$ alkyl, an amino substituted $C_1$-$C_3$ alkyl and $R^2$, $R^3$, $R^4$ are said, or when $R^2$ is a substituted amino group, an optionally substituted hydroxy group, a substituted mercapto group, an optionally substituted alkylamino group and $R^1$, $R^3$, $R^4$ are said;

$R^6$ is hydrogen, an optionally substituted $C_1$-$C_5$ alkyl, or an acyl.

2. The compound of claim 1, selected from the group consisting of substituted 2-(5-hydroxy-2-methyl-4-fluoro-1H-indol-3-yl)acetic acid of formula 1.1, substituted 2-(5-hydroxy-2-methyl-6-fluoro-1H-indol-3-yl)acetic acid of formula 1.2, substituted 2-(5-hydroxy-2-methyl-4-trifluoromethyl-1H-indol-3-yl)acetic acid of formula 1.3, substituted 2-(5-hydroxy-2-methyl-6-trifluoromethyl-1H-indol-3-yl)acetic acid of formula 1.4, substituted 2-(5-hydroxy-2-methyl-4-cyano-1H-indol-3-yl)acetic acid of formula of the general formula 1.5, and substituted 2-(5-hydroxy-2-methyl-6-cyano-1H-indol-3-yl)acetic acid of formula 1.6, or a pharmaceutically acceptable salt or hydrate thereof,

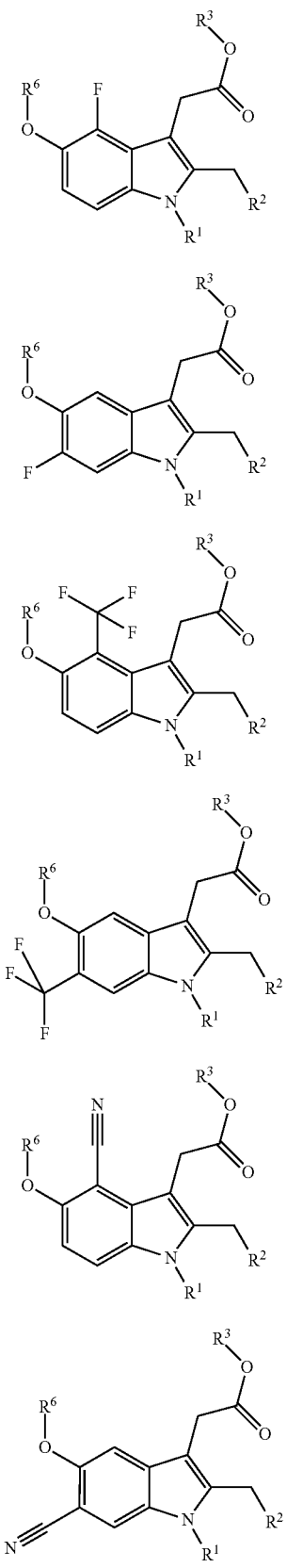

1.1
1.2
1.3
1.4
1.5
1.6 wherein R¹, R², R³ and R⁶ are said.

3. The compound of claim 2, selected from the group consisting of substituted 2-(5-hydroxy-2-methyl-1H-indol-3-yl)acetic acid of formula 1.1, 1.2, 1.3, and 1.4, or a pharmaceutically acceptable salt or hydrate thereof, wherein R¹ is methyl, 2-hydroxyethyl, 2-(dimethylamino)ethyl, a possibly substituted sulfonyl, and R², R³, R⁶ are said, or R¹ is 4-chlorobenzoyl and R² is not hydrogen.

4. The compound of claim 2, selected from the group representing substituted 2-(5-hydroxy-2-methyl-1H-indol-3-yl)acetic acid of formula 1.5 or 1.6, or a pharmaceutically acceptable salt or hydrate thereof, wherein R¹ is hydrogen, methyl, 2-hydroxyethyl, 2-(dimethylamino)ethyl, 4-chlorobenzoyl, a possibly substituted sulfonyl and R², R³, R⁶ are said.

5. The compound of claim 2, selected from the group consisting of substituted 2-(5-hydroxy-2-methyl-1H-indol-3-yl)acetic acid of formula 1.1, 1.2, 1.3, 1.4, or a pharmaceutically acceptable salt or hydrate thereof, wherein R² is a hydroxy group, a substituted hydroxy group, a dimethylamino group, (dimethylamino)methyl, a substituted mercapto group, and R¹, R³, R⁶ are said.

6. The compound of claim 2, selected from the group representing substituted 2-(5-hydroxy-2-methyl-1H-indol-3-yl)acetic acid of formula 1.5 or 1.6, or a pharmaceutically acceptable salt or hydrate thereof, wherein R² is a hydroxy group, a substituted hydroxy group, a dimethylamino group, (dimethylamino)methyl, a substituted mercapto group and R¹, R³, R⁶ are said.

7. The compound of claim 2, selected from the group consisting of substituted 2-(5-hydroxy-2-methyl-1H-indol-3-yl)acetic acid of the general formula 1.1, 1.2, 1.3, 1.4, 1.5, and 1.6, or a pharmaceutically acceptable salt or hydrate thereof wherein R³ is hydrogen, methyl, ethyl and R¹, R², R⁶ are said.

8. The compound of claim 2, selected from the group consisting of substituted 2-(5-hydroxy-2-methyl-1H-indol-3-yl)acetic acid of formula 1.1, 1.2, 1.3, 1.4, 1.5, and 1.6, or a pharmaceutically acceptable salt or hydrate thereof wherein R⁶ is hydrogen, methyl, iso-propyl, 3-pentyl or acetyl and R¹, R², R³ are said.

9. The compound of claim 1, selected from the group consisting of a compound of formula 1a, 1b, 1c, 1d, 1e, 1f, 1g, 1h, 1i, 1k, 1l, 1m, 1n, 1o, 1p, 1q, 1r, 1s, 1t, 1u, 1v, 1w, and 1x, or a pharmaceutically acceptable salt or hydrate thereof,

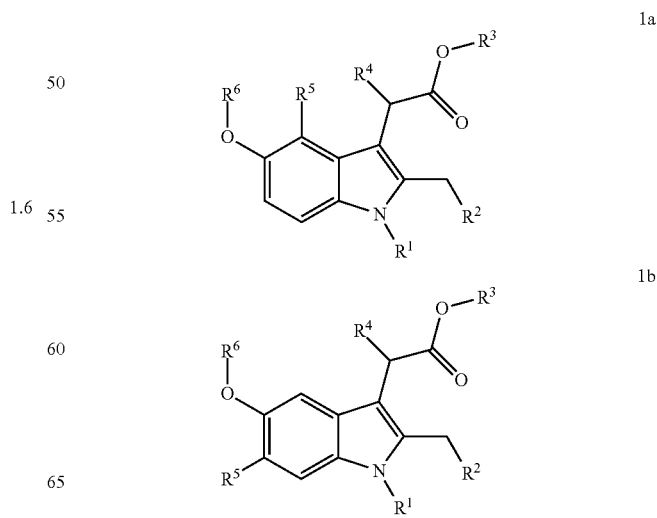

-continued
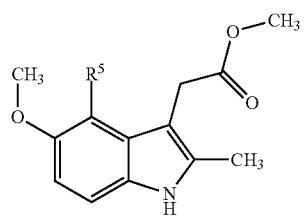
1c
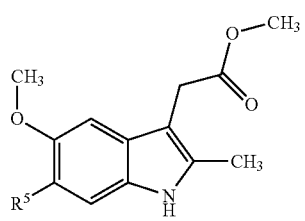
1d
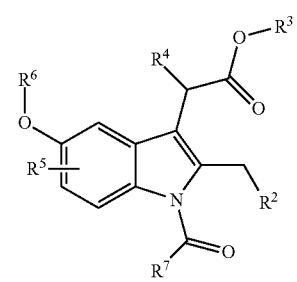
1e
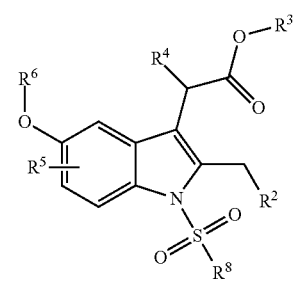
1f
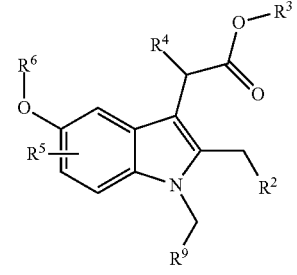
1g
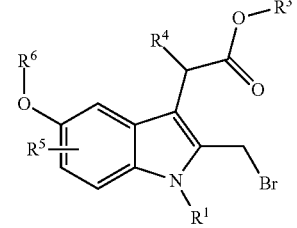
1h
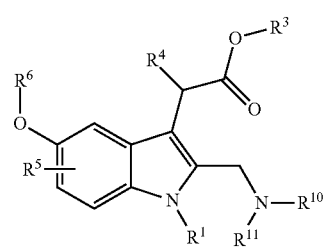
1i
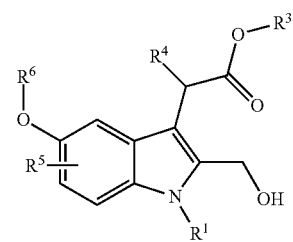
1k
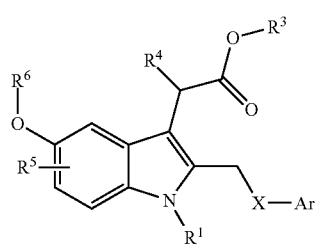
1l: X = O,
1m: X = S
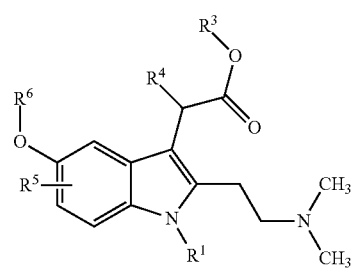
1n
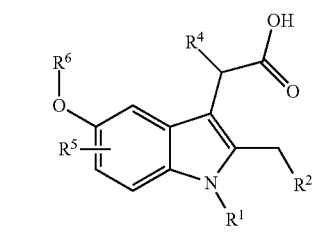
1o
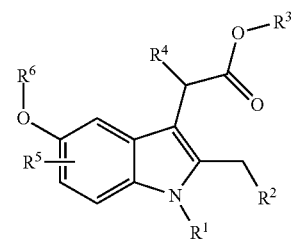
1p

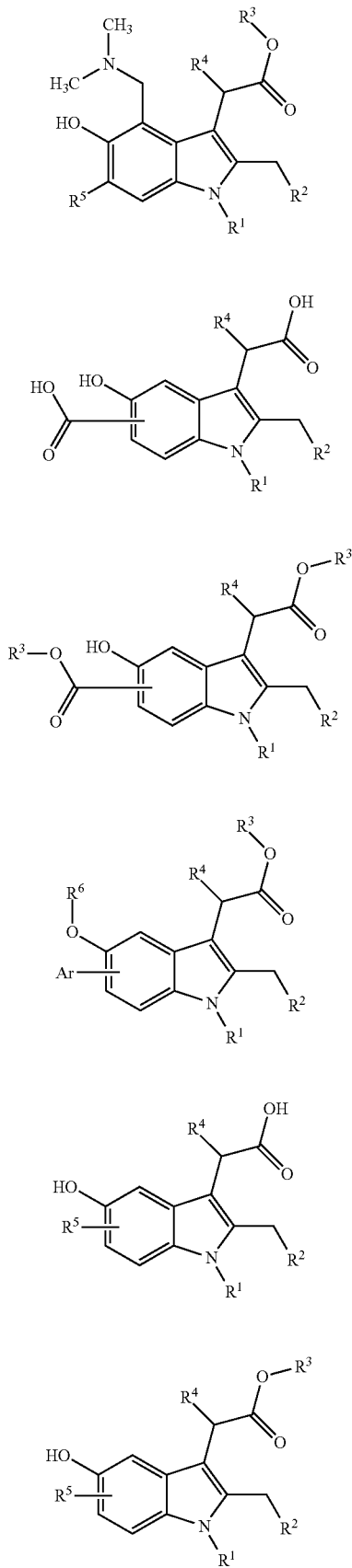

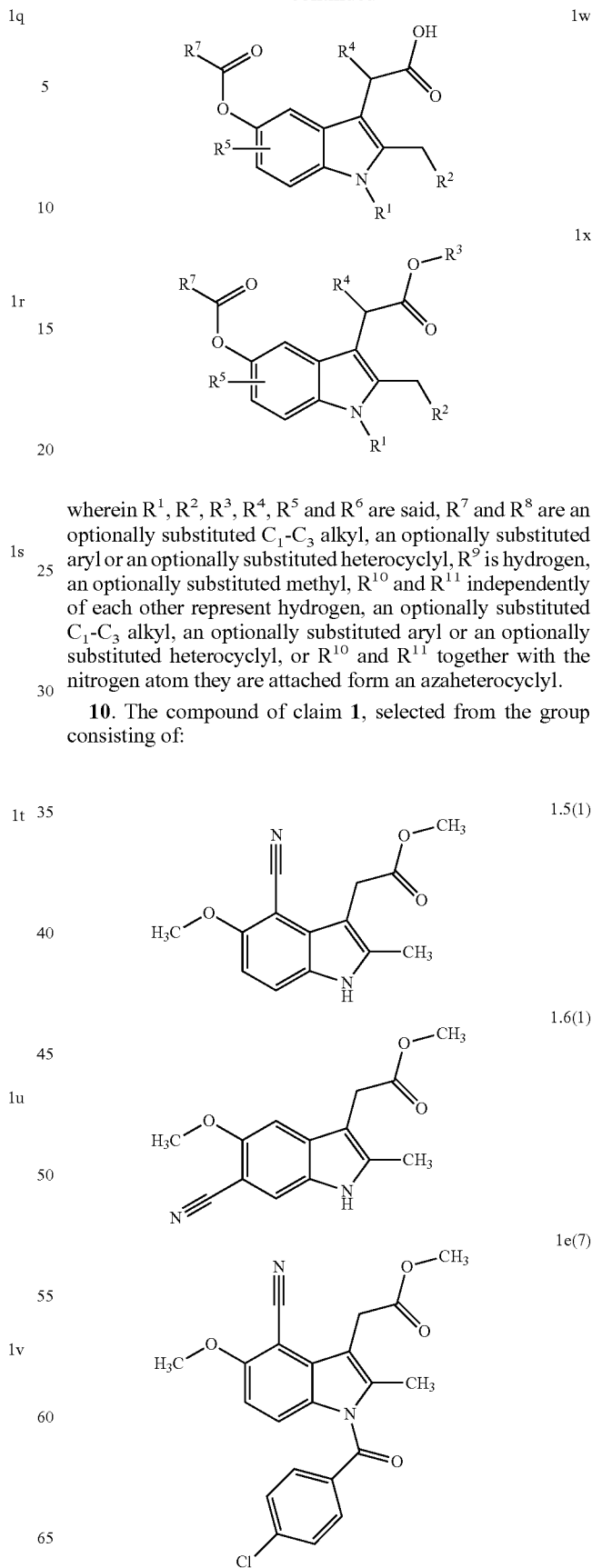

wherein $R^1$, $R^2$, $R^3$, $R^4$, $R^5$ and $R^6$ are said, $R^7$ and $R^8$ are an optionally substituted $C_1$-$C_3$ alkyl, an optionally substituted aryl or an optionally substituted heterocyclyl, $R^9$ is hydrogen, an optionally substituted methyl, $R^{10}$ and $R^{11}$ independently of each other represent hydrogen, an optionally substituted $C_1$-$C_3$ alkyl, an optionally substituted aryl or an optionally substituted heterocyclyl, or $R^{10}$ and $R^{11}$ together with the nitrogen atom they are attached form an azaheterocyclyl.

10. The compound of claim 1, selected from the group consisting of:

| | |
|---|---|
| 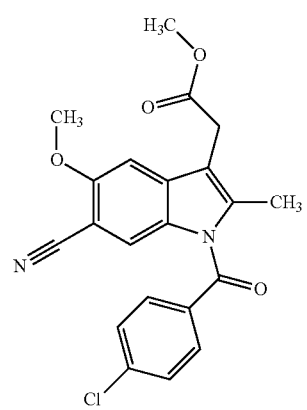 1e(8) | 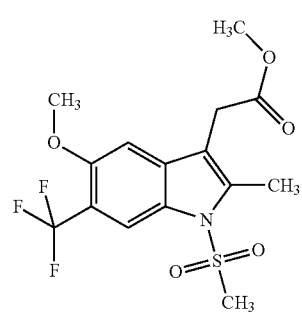 1f(4) |
| 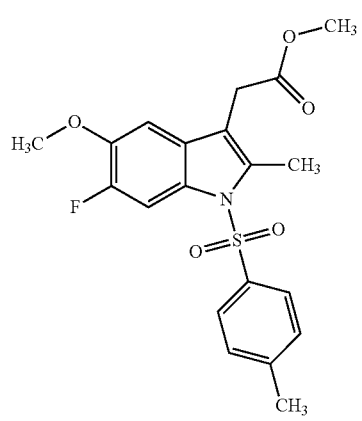 1f(1) | 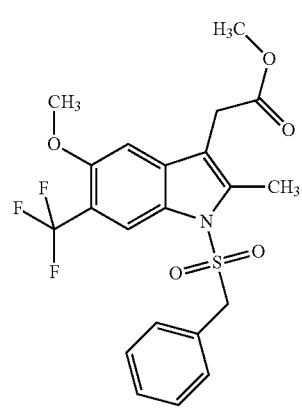 1f(5) |
| 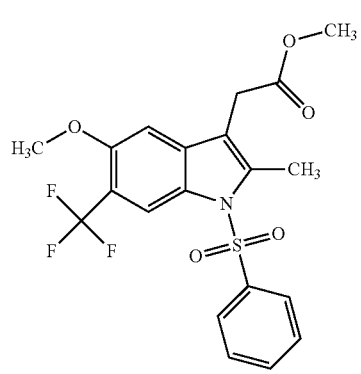 1f(2) | 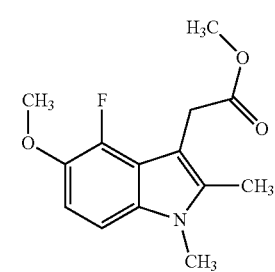 1g(1) |
| 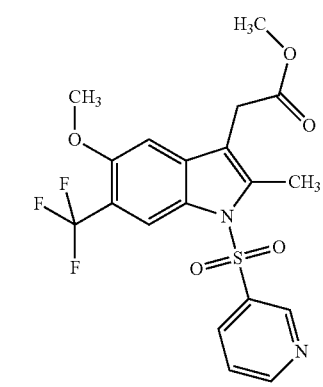 1f(3) | 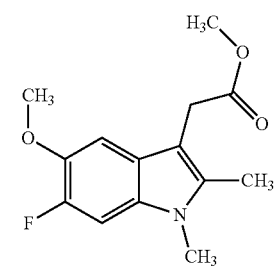 1g(2) |
| | 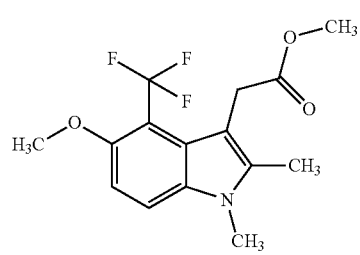 1g(3) |

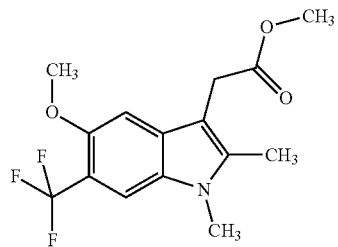
1g(4)
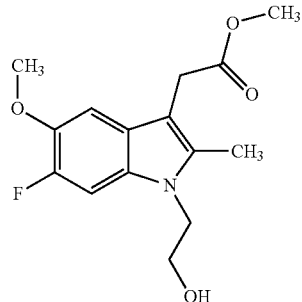
1g(9)
1g(5)
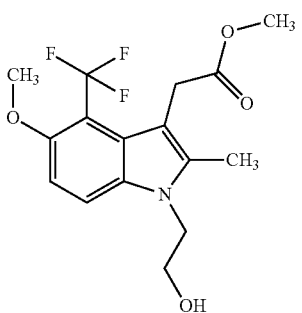
1g(10)
1g(6)
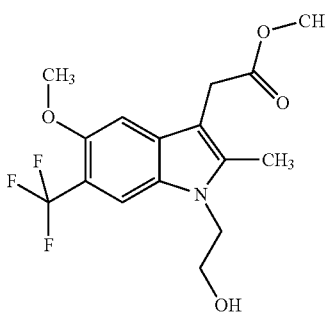
1g(11)
1g(7)
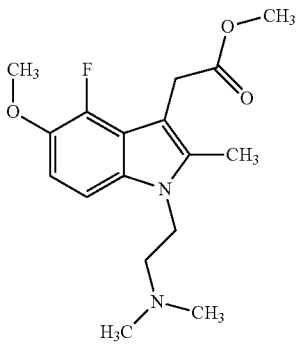
1g(12)
1g(8)
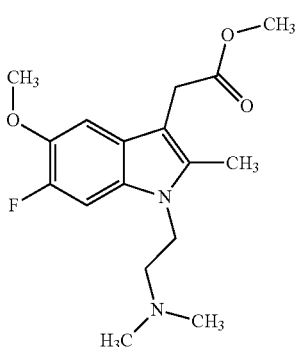
1g(13)

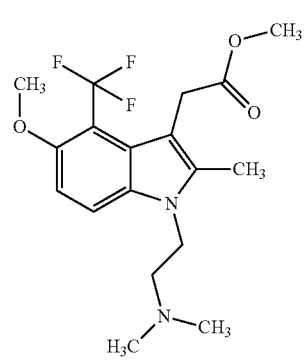
1g(14)
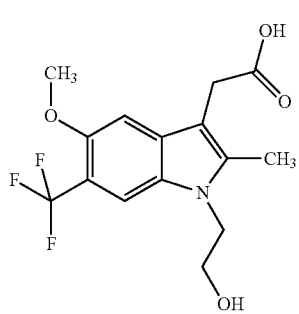
1i(1)
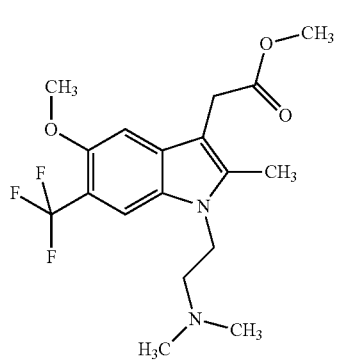
1g(15)
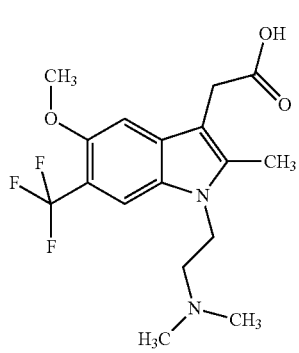
1i(2)
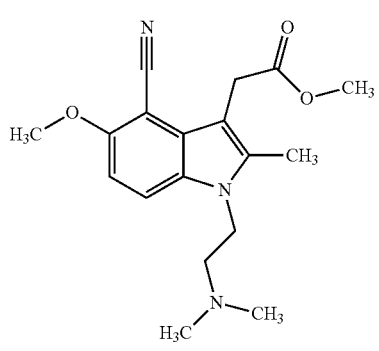
1g(16)
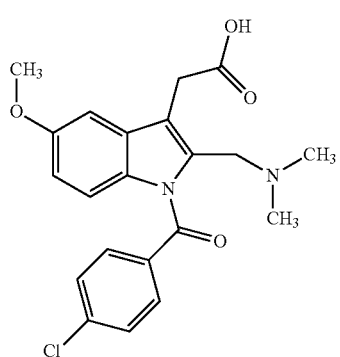
1i(3)
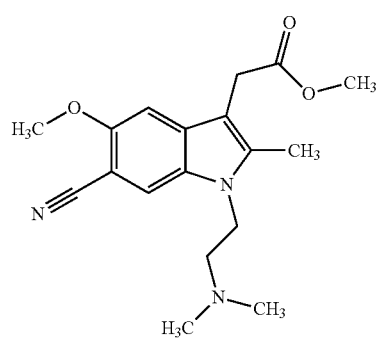
1g(17)
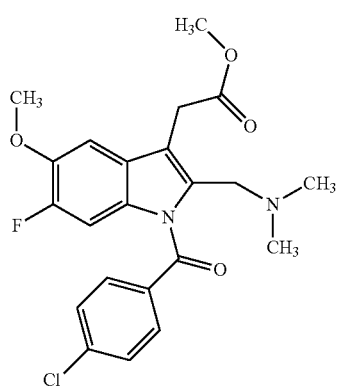
1i(4)

1i(5)
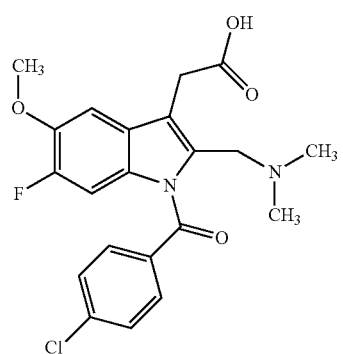
1i(6)
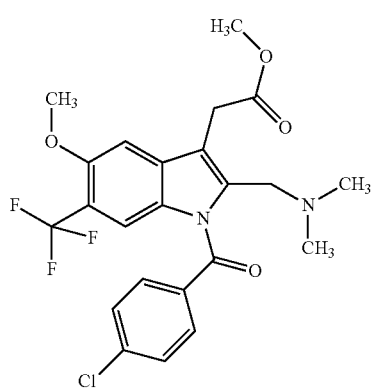
1i(7)
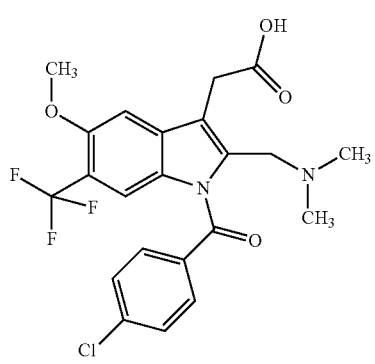
1i(8)
1i(9)
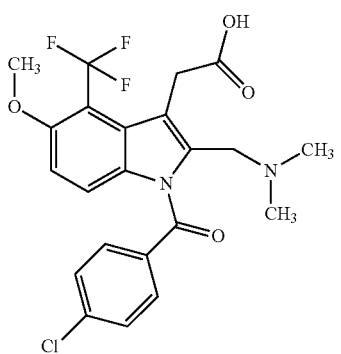
1i(10)
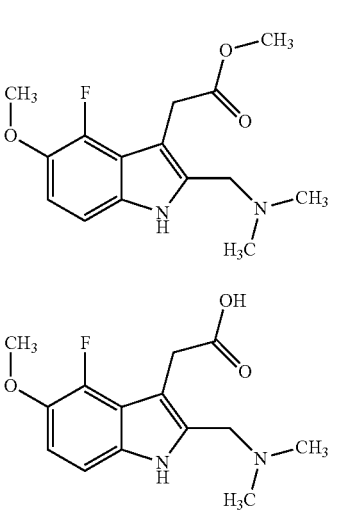
1i(11)
1i(12)
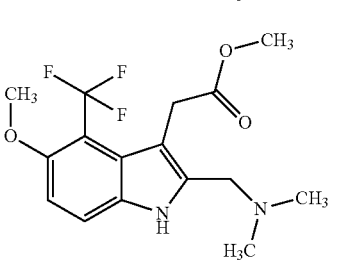
1i(13)
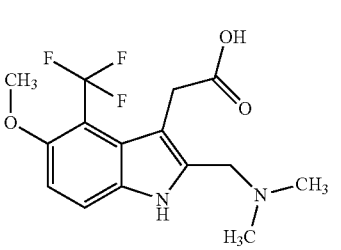
1i(14)
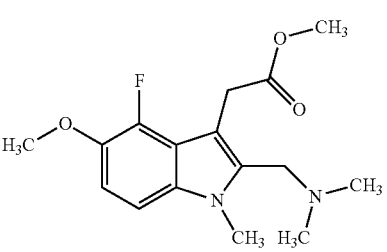

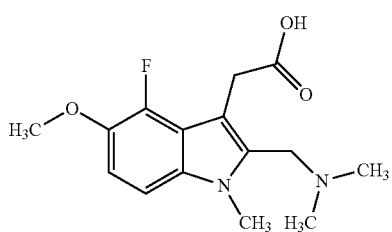 1i(15)
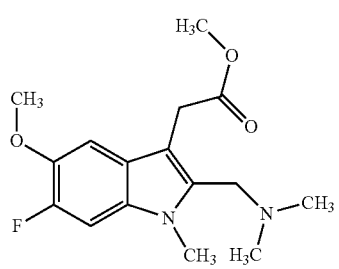 1i(22)
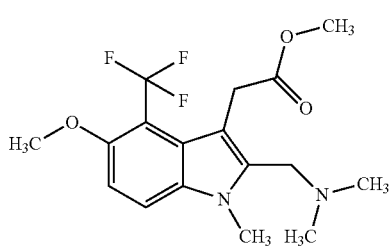 1i(16)
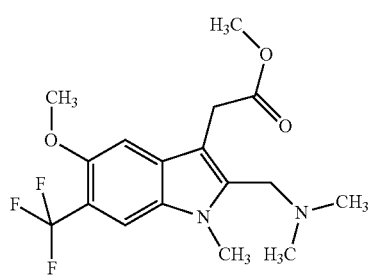 1i(23)
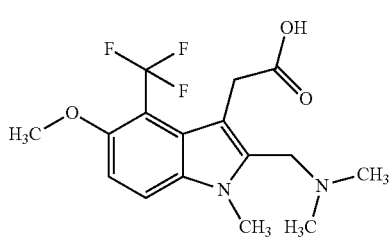 1i(17)
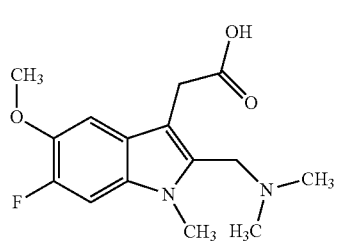 1i(24)
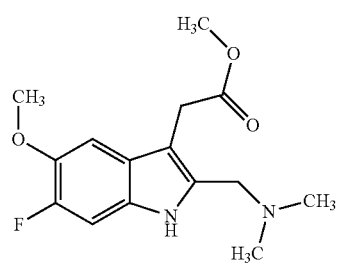 1i(18)
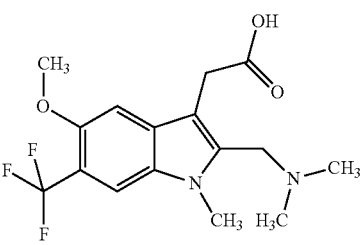 1i(25)
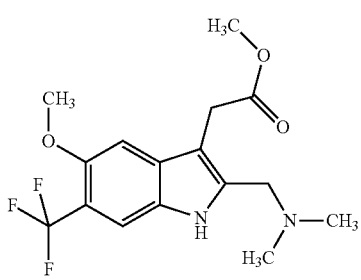 1i(19)
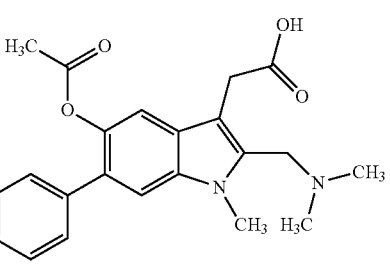 1i(26)
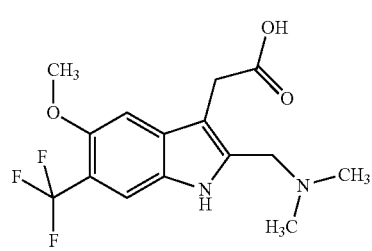 1i(20)
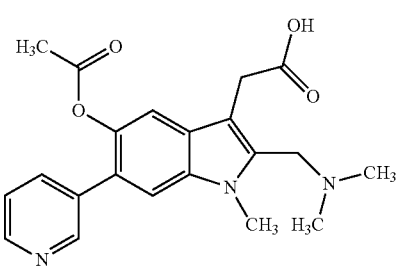 1i(27)

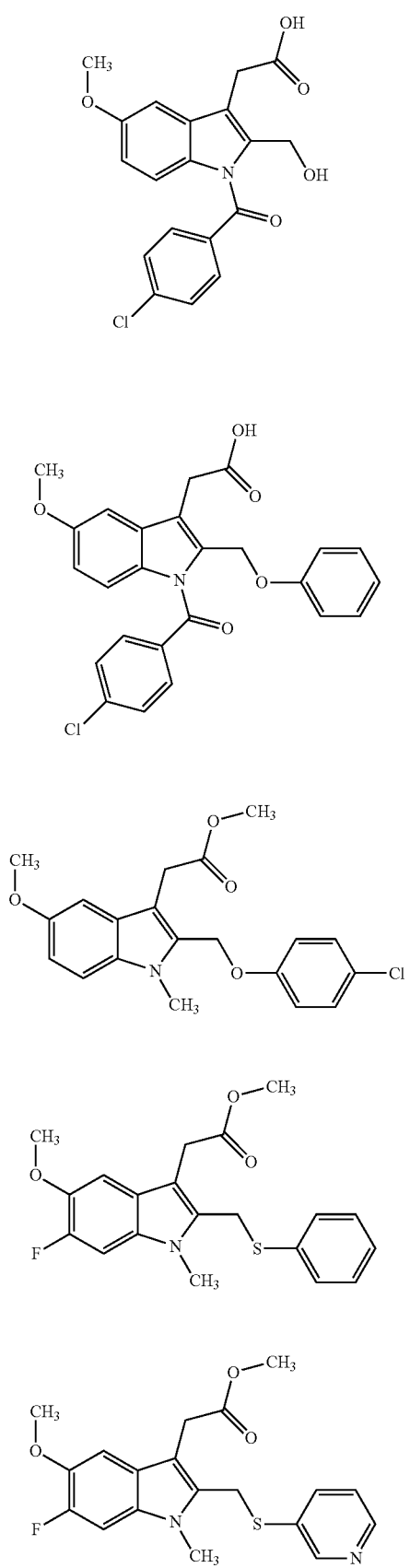
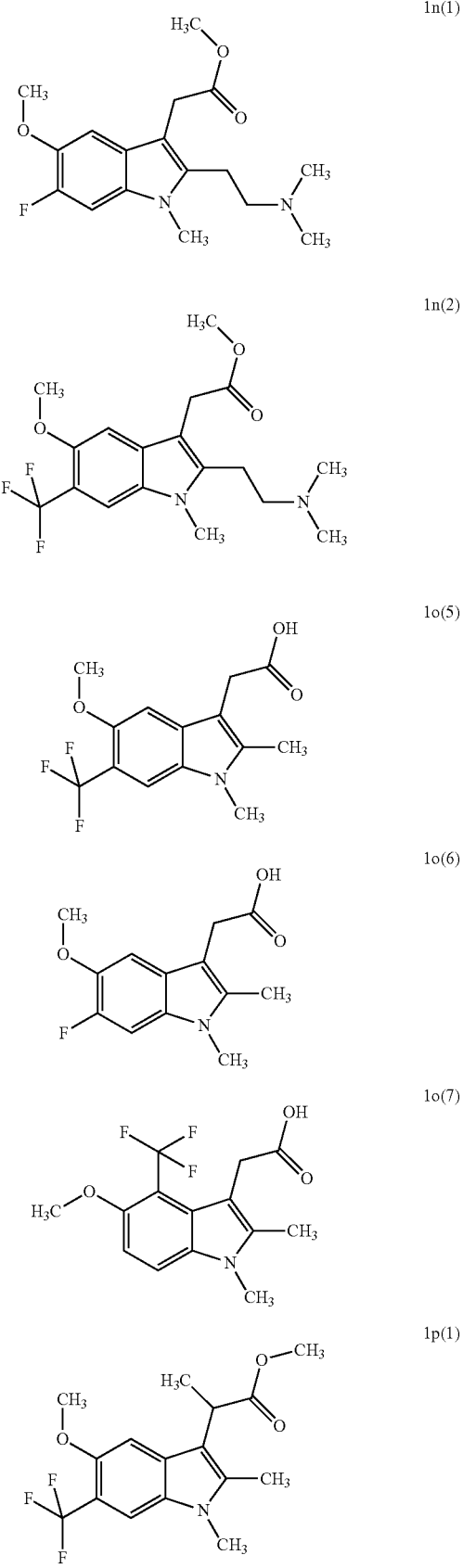

-continued
1p(2)
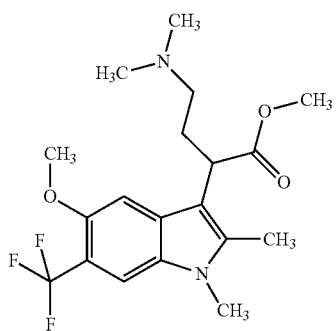
1p(3)
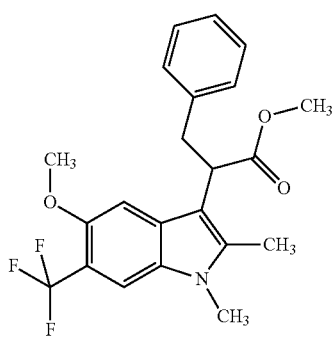
1p(4)
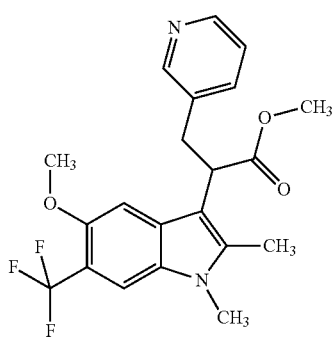
1q(1)
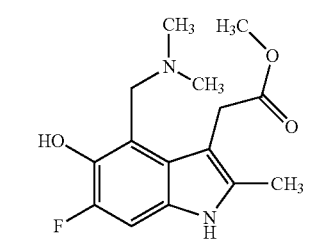
1q(2)
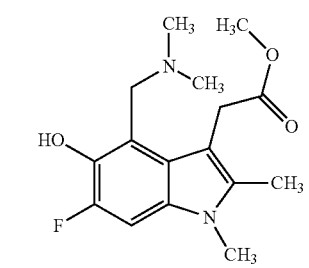
-continued
1q(3)
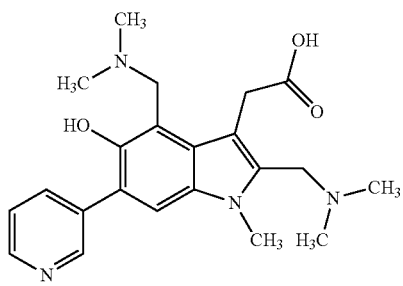
1r(1)
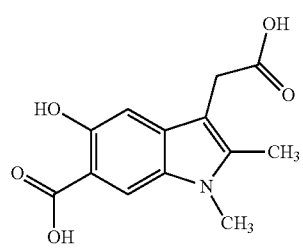
1s(1)
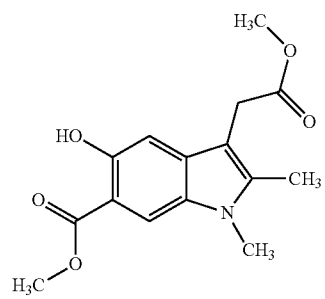
1t(1)
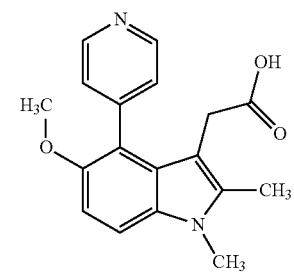
1t(2)
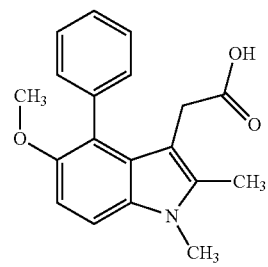

1t(3)
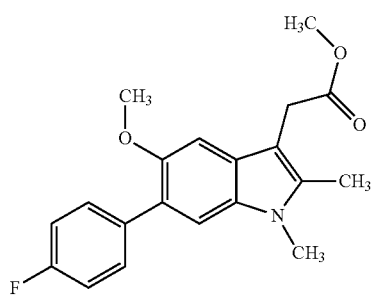
1t(4)
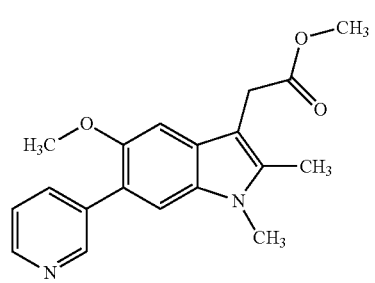
1t(5)
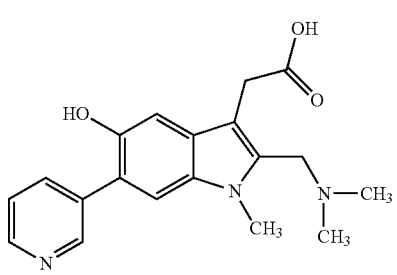
1u(1)
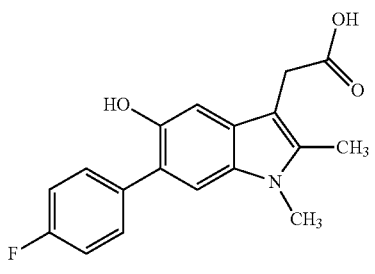
1u(2)
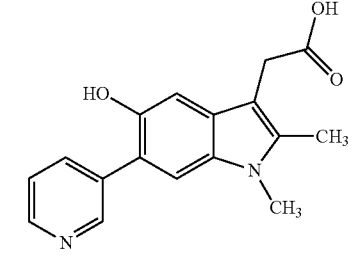
1u(5)
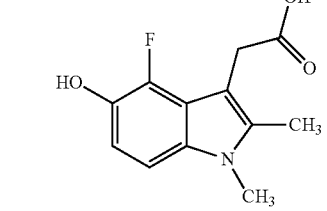
1u(6)
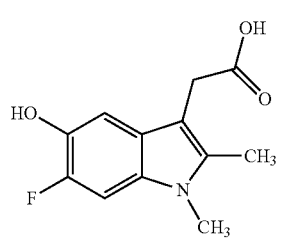
1u(7)
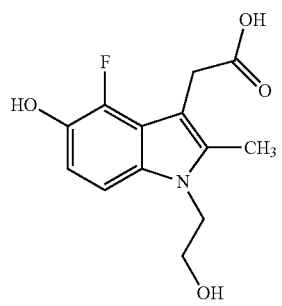
1u(8)
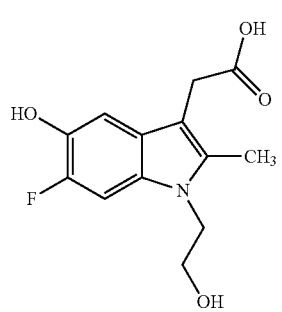
1u(9)
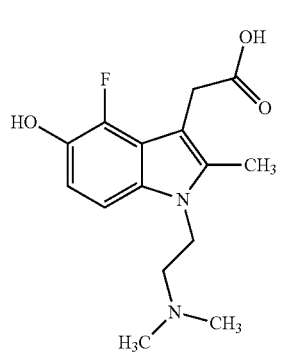
1u(10)
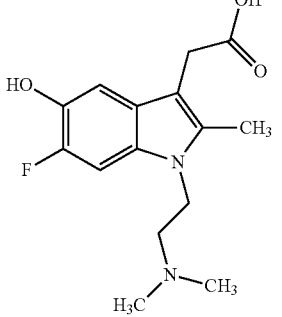

or a pharmaceutically acceptable salt or hydrate thereof.

11. An antiviral agent for a pharmaceutical composition or medicament comprising a compound of general formula 1, or a pharmaceutically acceptable salt or hydrate thereof, wherein R¹ is hydrogen, an optionally substituted $C_1$-$C_5$ alkyl, an optionally substituted $C_1$-$C_5$ alkyl-, aryl- or heterocyclyl- carbonyl or an optionally substituted $C_1$-$C_5$ alkyl-, aryl- or heterocyclyl-sulfonyl;

R² and R⁴ independently of each other represent hydrogen, an optionally substituted $C_1$-$C_3$ alkyl, an optionally substituted hydroxy group, an optionally substituted amino group, an optionally substituted aminomethyl, a substituted mercapto group;

R³ is hydrogen, an optionally substituted $C_1$-$C_5$ alkyl;

R⁵ is hydrogen, fluoro, trifluoromethyl, carboxyl, alkyloxycarbonyl, a possibly substituted aryl, a heterocyclyl, an optionally substituted aminomethyl, a cyano group;

R⁶ is hydrogen, an optionally substituted $C_1$-$C_5$ alkyl, an acyl.

12. The antiviral agent according to claim 11, wherein said antiviral agent has an antiviral ability against influenza virus.

13. The antiviral agent according to claim 11, wherein said antiviral agent has an antiviral ability against hepatitis C virus (HCV).

14. A pharmaceutical composition with antiviral activity comprising as an active ingredient at least one compound of general formula 1, or a pharmaceutically acceptable salt or hydrate thereof, according to claim 11 and a pharmaceutically acceptable carrier, or an inert excipient, or solvent.

15. The pharmaceutical composition according to claim 14, wherein said pharmaceutical composition has an antiviral ability against influenza virus.

16. The pharmaceutical composition according to claim 14 wherein said pharmaceutical composition has an antiviral ability against hepatitis C virus (HCV).

17. The pharmaceutical composition according to claim 14 in the form of a tablet, a capsule, or an injection placed in a pharmaceutically acceptable packing.

18. A method for treating a viral disease in a subject caused by influenza virus or hepatitis C (HCV) virus comprising administering to a subject an effective amount of the pharmaceutical composition according to claim 14 in need thereof.

19. A therapeutic cocktail for treating a viral disease in a subject caused by influenza virus and hepatitis C (HCV) virus comprising a pharmaceutically effective amount of a compound of general formula 1, or a pharmaceutically acceptable salt or hydrate thereof, according to claim 11.

* * * * *